(12) United States Patent
Walberg et al.

(10) Patent No.: US 7,841,502 B2
(45) Date of Patent: Nov. 30, 2010

(54) MODULAR CLIP APPLIER

(75) Inventors: Erik K. Walberg, Redwood City, CA (US); Timothy C. Reynolds, Sunnyvale, CA (US); Anthony J. Pantages, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 182 days.

(21) Appl. No.: 11/959,334

(22) Filed: Dec. 18, 2007

(65) Prior Publication Data

US 2009/0157103 A1 Jun. 18, 2009

(51) Int. Cl.
*A61B 17/068* (2006.01)

(52) U.S. Cl. .................. 227/175.1; 227/19; 227/175.2; 606/139; 606/219

(58) Field of Classification Search .................. 227/19, 227/176.1, 175.1, 175.2; 606/139, 219
See application file for complete search history.

(56) References Cited

U.S. PATENT DOCUMENTS

| | | | |
|---|---|---|---|
| 287,046 | A | 10/1883 | Norton |
| 438,400 | A | 10/1890 | Brennen |
| 1,088,393 | A | 2/1914 | Backus |
| 1,331,401 | A | 2/1920 | Summers |
| 1,426,111 | A | 8/1922 | Sacker |
| 1,516,990 | A | 11/1924 | Silverman |
| 1,596,004 | A | 8/1926 | De Bengoa |
| 1,647,958 | A | 11/1927 | Ciarlante |
| 1,847,347 | A | 3/1932 | Maisto |
| 1,852,098 | A | 4/1932 | Anderson |
| 1,880,569 | A | 10/1932 | Weis |
| 2,075,508 | A | 3/1937 | Davidson |
| 2,087,074 | A | 7/1937 | Tucker |
| 2,254,620 | A | 9/1941 | Miller |
| 2,316,297 | A | 4/1943 | Southerland et al. |
| 2,371,978 | A | 3/1945 | Perham |
| 2,453,227 | A | 11/1948 | James |
| 2,583,625 | A | 1/1952 | Bergan |

(Continued)

FOREIGN PATENT DOCUMENTS

CA    2 339 060    2/2000

(Continued)

OTHER PUBLICATIONS

U.S. Appl. No. 10/264,306, filed Jan. 27, 2010, Office Action.

(Continued)

*Primary Examiner*—Scott A. Smith
(74) *Attorney, Agent, or Firm*—Workman Nydegger

(57) ABSTRACT

An apparatus for placement into an opening formed in a wall of a body lumen to deploy a closure element. The apparatus comprising a housing having a handle portion formed at a distal end, the handle portion configured to be engaged by a user when advancing the housing to deploy the closure element. A triggering element deploys the closure device and can at least be partially formed in the housing. A throw reducing mechanism can slide relative to the housing and reduce the distance a user must stretch a hand to move a triggering system within the housing. The housing can include, or be connected to, a handle member having one or more expansion members which expand to provide a stable base for manipulating the apparatus.

18 Claims, 24 Drawing Sheets

U.S. PATENT DOCUMENTS

| | | |
|---|---|---|
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,976,079 A | 8/1976 | Samuels et al. |
| 3,985,138 A | 10/1976 | Jarvik |
| 4,014,492 A | 3/1977 | Rothfuss |
| 4,018,228 A | 4/1977 | Goosen |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Vaillancourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,439 A | 3/1991 | Chen |
| 4,997,736 A | 3/1991 | Kawamura et al. |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,147,381 A | 9/1992 | Heimerl et al. |
| 5,156,609 A | 10/1992 | Nakao et al. |
| 5,158,566 A | 10/1992 | Pianetti |

| | | | | | |
|---|---|---|---|---|---|
| 5,160,339 A | 11/1992 | Chen et al. | 5,425,740 A | 6/1995 | Hutchinson, Jr. |
| 5,167,634 A | 12/1992 | Corrigan, Jr. et al. | 5,431,639 A | 7/1995 | Shaw |
| 5,167,643 A | 12/1992 | Lynn | 5,431,667 A | 7/1995 | Thompson et al. |
| 5,171,249 A | 12/1992 | Stefanchik et al. | 5,433,721 A | 7/1995 | Hooven et al. |
| 5,171,250 A | 12/1992 | Yoon | 5,437,631 A | 8/1995 | Janzen |
| 5,171,251 A | 12/1992 | Bregen et al. | 5,439,479 A | 8/1995 | Shichman et al. |
| 5,176,648 A | 1/1993 | Holmes et al. | 5,443,477 A * | 8/1995 | Marin et al. ................ 606/198 |
| 5,176,682 A | 1/1993 | Chow | 5,443,481 A | 8/1995 | Lee |
| 5,192,300 A | 3/1993 | Fowler | 5,449,359 A | 9/1995 | Groiso |
| 5,192,301 A | 3/1993 | Kamiya et al. | 5,456,400 A | 10/1995 | Shichman et al. |
| 5,192,302 A * | 3/1993 | Kensey et al. ................ 606/213 | 5,462,558 A | 10/1995 | Kolesa et al. |
| 5,192,602 A | 3/1993 | Spencer et al. | 5,462,561 A | 10/1995 | Voda |
| 5,203,787 A | 4/1993 | Noblitt et al. | 5,466,241 A | 11/1995 | Leroy et al. |
| 5,209,756 A | 5/1993 | Seedhom et al. | 5,470,010 A | 11/1995 | Rothfuss et al. |
| 5,217,024 A | 6/1993 | Dorsey et al. | 5,474,557 A | 12/1995 | Mai |
| 5,219,359 A | 6/1993 | McQuilkin et al. | 5,474,572 A | 12/1995 | Hayhurst |
| 5,222,974 A * | 6/1993 | Kensey et al. ................ 606/213 | 5,478,352 A | 12/1995 | Fowler |
| 5,226,908 A | 7/1993 | Yoon | 5,478,353 A | 12/1995 | Yoon |
| 5,234,449 A | 8/1993 | Bruker et al. | 5,478,354 A | 12/1995 | Tovey et al. |
| 5,236,435 A | 8/1993 | Sewell, Jr. | 5,486,195 A | 1/1996 | Myers et al. |
| 5,236,445 A | 8/1993 | Hayhurst et al. | 5,497,933 A | 3/1996 | DeFonzo et al. |
| 5,242,457 A | 9/1993 | Akopov et al. | 5,501,698 A | 3/1996 | Roth et al. |
| 5,242,459 A | 9/1993 | Buelna | 5,507,744 A | 4/1996 | Tay et al. |
| 5,243,857 A | 9/1993 | Velez | 5,507,755 A | 4/1996 | Gresl et al. |
| 5,246,156 A | 9/1993 | Rothfuss et al. | 5,514,159 A | 5/1996 | Matula et al. |
| 5,246,443 A | 9/1993 | Mai | 5,521,184 A | 5/1996 | Zimmermann |
| 5,250,058 A | 10/1993 | Miller et al. | 5,522,840 A | 6/1996 | Krajicek |
| 5,254,105 A | 10/1993 | Haaga | 5,527,322 A | 6/1996 | Klein et al. |
| 5,258,015 A | 11/1993 | Li et al. | 5,536,251 A | 7/1996 | Evard et al. |
| 5,269,792 A | 12/1993 | Kovac et al. | 5,540,712 A | 7/1996 | Kleshinski et al. |
| 5,275,616 A | 1/1994 | Fowler | 5,540,716 A | 7/1996 | Hlavacek |
| 5,282,808 A | 2/1994 | Kovac et al. | 5,543,520 A | 8/1996 | Zimmermann |
| 5,282,827 A | 2/1994 | Kensey et al. | 5,544,802 A | 8/1996 | Crainich |
| 5,282,832 A | 2/1994 | Toso et al. | 5,547,474 A | 8/1996 | Kloeckl et al. |
| 5,289,963 A | 3/1994 | McGarry et al. | 5,560,532 A | 10/1996 | DeFonzo et al. |
| 5,290,243 A | 3/1994 | Chodorow et al. | 5,571,120 A | 11/1996 | Yoon |
| 5,290,310 A | 3/1994 | Makower et al. | 5,575,771 A | 11/1996 | Walinsky |
| 5,292,309 A | 3/1994 | Van Tassel et al. | 5,584,879 A | 12/1996 | Reimold et al. |
| 5,292,332 A | 3/1994 | Lee | 5,591,205 A | 1/1997 | Fowler |
| 5,304,184 A | 4/1994 | Hathaway et al. | 5,593,412 A | 1/1997 | Martinez et al. |
| 5,304,204 A | 4/1994 | Bregen | 5,593,422 A | 1/1997 | Muijs Van de Moer et al. |
| 5,306,254 A | 4/1994 | Nash et al. | 5,593,425 A | 1/1997 | Bonutti et al. |
| 5,306,280 A | 4/1994 | Bregen et al. | 5,601,602 A | 2/1997 | Fowler |
| 5,318,542 A | 6/1994 | Hirsch et al. | 5,609,597 A | 3/1997 | Lehrer |
| 5,320,639 A | 6/1994 | Rudnick | 5,611,986 A | 3/1997 | Datta et al. |
| 5,330,442 A | 7/1994 | Green et al. | 5,613,974 A | 3/1997 | Andreas et al. |
| 5,330,445 A | 7/1994 | Haaga | 5,618,291 A | 4/1997 | Thompson et al. |
| 5,334,216 A | 8/1994 | Vidal et al. | 5,618,306 A | 4/1997 | Roth et al. |
| 5,334,217 A | 8/1994 | Das | 5,620,452 A | 4/1997 | Yoon |
| 5,335,680 A | 8/1994 | Moore | 5,620,461 A | 4/1997 | Muijs et al. |
| 5,340,360 A | 8/1994 | Stefanchik | 5,630,824 A | 5/1997 | Hart |
| 5,350,399 A | 9/1994 | Erlebacher et al. | 5,643,318 A | 7/1997 | Tsukernik et al. |
| 5,352,229 A | 10/1994 | Goble et al. | 5,645,553 A | 7/1997 | Kolesa et al. |
| 5,364,406 A | 11/1994 | Sewell, Jr. | 5,645,565 A | 7/1997 | Rudd et al. |
| 5,364,408 A | 11/1994 | Gordon | 5,645,566 A | 7/1997 | Brenneman et al. |
| 5,366,458 A | 11/1994 | Korthoff et al. | 5,645,567 A | 7/1997 | Crainich |
| 5,366,479 A | 11/1994 | McGarry et al. | 5,649,959 A | 7/1997 | Hannam et al. |
| 5,376,101 A | 12/1994 | Green et al. | D383,539 S | 9/1997 | Croley |
| 5,383,896 A | 1/1995 | Gershony et al. | 5,669,917 A | 9/1997 | Sauer et al. |
| 5,383,905 A | 1/1995 | Golds et al. | 5,674,231 A * | 10/1997 | Green et al. ................ 606/142 |
| RE34,866 E | 2/1995 | Kensey et al. | 5,676,689 A * | 10/1997 | Kensey et al. ................ 606/213 |
| 5,391,173 A | 2/1995 | Wilk | 5,676,974 A | 10/1997 | Valdes et al. |
| 5,392,978 A | 2/1995 | Velez et al. | 5,681,334 A | 10/1997 | Evans et al. |
| 5,395,030 A | 3/1995 | Kuramoto et al. | 5,681,351 A | 10/1997 | Jamiolkowski et al. |
| 5,409,499 A | 4/1995 | Yi | 5,683,405 A | 11/1997 | Yacoubian et al. |
| 5,411,520 A | 5/1995 | Nash et al. | 5,690,674 A | 11/1997 | Diaz |
| 5,413,571 A | 5/1995 | Katsaros et al. | 5,695,504 A | 12/1997 | Gifford, III et al. |
| 5,413,584 A | 5/1995 | Schulze | 5,695,505 A | 12/1997 | Yoon |
| 5,416,584 A | 5/1995 | Kay | 5,695,524 A | 12/1997 | Kelley et al. |
| 5,417,699 A | 5/1995 | Klein et al. | 5,700,273 A | 12/1997 | Buelna et al. |
| 5,419,777 A | 5/1995 | Hofling | 5,709,708 A | 1/1998 | Thal |
| 5,423,857 A | 6/1995 | Rosenman et al. | 5,716,375 A | 2/1998 | Fowler |
| 5,425,489 A | 6/1995 | Shichman et al. | 5,720,755 A | 2/1998 | Dakov |

| Patent No. | Date | Name |
|---|---|---|
| 5,720,765 A | 2/1998 | Thal |
| 5,725,498 A | 3/1998 | Janzen et al. |
| 5,725,552 A | 3/1998 | Kotula et al. |
| 5,725,554 A | 3/1998 | Simon et al. |
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,732,872 A | 3/1998 | Bolduc et al. |
| 5,735,873 A | 4/1998 | MacLean |
| 5,735,875 A | 4/1998 | Bonutti et al. |
| 5,735,877 A | 4/1998 | Pagedas |
| 5,749,898 A | 5/1998 | Schulze et al. |
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,862 A | 6/1998 | Kammerer et al. |
| 5,769,870 A | 6/1998 | Salahieh et al. |
| 5,776,150 A | 7/1998 | Nolan et al. |
| 5,779,707 A | 7/1998 | Bertholet et al. |
| 5,782,844 A | 7/1998 | Yoon et al. |
| 5,782,860 A | 7/1998 | Epstein et al. |
| 5,782,861 A | 7/1998 | Cragg et al. |
| 5,782,864 A | 7/1998 | Lizardi |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,810,776 A | 9/1998 | Bacich et al. |
| 5,810,846 A | 9/1998 | Virnich et al. |
| 5,810,851 A | 9/1998 | Yoon |
| 5,810,877 A | 9/1998 | Roth et al. |
| 5,814,069 A | 9/1998 | Schulze et al. |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,833,698 A | 11/1998 | Hinchliffe et al. |
| 5,843,167 A | 12/1998 | Dwyer et al. |
| 5,846,254 A | 12/1998 | Schulze et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,005 A | 1/1999 | Kontos |
| 5,868,755 A | 2/1999 | Kanner et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,873,876 A | 2/1999 | Christy |
| 5,879,366 A | 3/1999 | Shaw et al. |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,919,208 A | 7/1999 | Valenti |
| 5,922,009 A | 7/1999 | Epstein et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,951,518 A | 9/1999 | Licata et al. |
| 5,951,576 A | 9/1999 | Wakabayashi |
| 5,951,589 A | 9/1999 | Epstein et al. |
| 5,957,936 A | 9/1999 | Yoon et al. |
| 5,957,938 A | 9/1999 | Zhu et al. |
| 5,964,782 A | 10/1999 | Lafontaine et al. |
| 5,976,159 A | 11/1999 | Bolduc et al. |
| 5,976,161 A | 11/1999 | Kirsch et al. |
| 5,984,934 A | 11/1999 | Ashby et al. |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,013,084 A | 1/2000 | Ken et al. |
| 6,022,372 A * | 2/2000 | Kontos .................. 606/219 |
| 6,024,750 A | 2/2000 | Mastri |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,063,085 A | 5/2000 | Tay et al. |
| 6,063,114 A | 5/2000 | Nash et al. |
| 6,066,160 A | 5/2000 | Colvin et al. |
| 6,071,300 A | 6/2000 | Brenneman et al. |
| 6,074,409 A | 6/2000 | Goldfarb |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,086,608 A | 7/2000 | Ek et al. |
| 6,090,130 A | 7/2000 | Nash et al. |
| 6,092,561 A | 7/2000 | Schmid |
| 6,099,553 A | 8/2000 | Hart et al. |
| 6,102,271 A | 8/2000 | Longo et al. |
| 6,106,545 A | 8/2000 | Egan |
| 6,110,184 A | 8/2000 | Weadock |
| 6,113,612 A | 9/2000 | Swanson et al. |
| 6,117,125 A | 9/2000 | Rothbarth et al. |
| 6,117,148 A | 9/2000 | Ravo |
| 6,120,524 A | 9/2000 | Taheri |
| 6,126,675 A | 10/2000 | Shchervinsky et al. |
| 6,126,677 A | 10/2000 | Ganaja et al. |
| 6,136,010 A | 10/2000 | Modesitt et al. |
| 6,143,017 A | 11/2000 | Thal |
| 6,149,660 A | 11/2000 | Laufer et al. |
| 6,149,667 A | 11/2000 | Hovland et al. |
| 6,152,144 A | 11/2000 | Lesh et al. |
| 6,152,934 A | 11/2000 | Harper et al. |
| 6,152,936 A | 11/2000 | Christy et al. |
| 6,152,937 A | 11/2000 | Peterson et al. |
| 6,159,234 A | 12/2000 | Bonutti et al. |
| 6,165,204 A | 12/2000 | Levinson et al. |
| 6,174,324 B1 | 1/2001 | Egan et al. |
| 6,193,734 B1 | 2/2001 | Bolduc et al. |
| 6,197,042 B1 | 3/2001 | Ginn et al. |
| 6,200,329 B1 | 3/2001 | Fung et al. |
| 6,203,565 B1 | 3/2001 | Bonutti et al. |
| 6,206,913 B1 | 3/2001 | Yencho et al. |
| 6,220,248 B1 | 4/2001 | Voegele et al. |
| 6,221,102 B1 | 4/2001 | Baker et al. |
| 6,231,592 B1 | 5/2001 | Bonutti et al. |
| 6,248,124 B1 | 6/2001 | Pedros et al. |
| 6,254,615 B1 | 7/2001 | Bolduc et al. |

| | | |
|---|---|---|
| 6,254,617 B1 | 7/2001 | Spence et al. |
| 6,254,642 B1 | 7/2001 | Taylor |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,305,891 B1 | 10/2001 | Burlingame |
| 6,319,258 B1 | 11/2001 | McAllen, III et al. |
| 6,322,580 B1 | 11/2001 | Kanner |
| 6,334,865 B1 | 1/2002 | Redmond et al. |
| 6,348,064 B1 | 2/2002 | Kanner |
| 6,358,258 B1 | 3/2002 | Arcia et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,423,054 B1 | 7/2002 | Ouchi |
| 6,428,472 B1 | 8/2002 | Haas |
| 6,428,548 B1 | 8/2002 | Durgin et al. |
| 6,443,158 B1 | 9/2002 | LaFontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,517,569 B2 | 2/2003 | Mikus et al. |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,599,303 B1 | 7/2003 | Peterson et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,623,509 B2 | 9/2003 | Ginn |
| 6,623,510 B2 | 9/2003 | Belef et al. |
| 6,626,918 B1 | 9/2003 | Ginn et al. |
| 6,632,238 B2 | 10/2003 | Ginn et al. |
| 6,634,537 B2 | 10/2003 | Chen |
| 6,645,205 B2 | 11/2003 | Ginn |
| 6,652,538 B2 | 11/2003 | Kayan et al. |
| 6,652,556 B1 | 11/2003 | VanTassel et al. |
| 6,663,655 B2 | 12/2003 | Ginn et al. |
| 6,669,714 B2 * | 12/2003 | Coleman et al. ............ 606/219 |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,749,621 B2 * | 6/2004 | Pantages et al. ............ 606/213 |
| 6,749,622 B2 | 6/2004 | McGuckin et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,926,723 B1 | 8/2005 | Mulhauser et al. |
| 6,926,731 B2 * | 8/2005 | Coleman et al. ............ 606/213 |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,083,635 B2 | 8/2006 | Ginn |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walburg et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,533,790 B1 * | 5/2009 | Knodel et al. ............ 227/175.1 |
| 7,597,706 B2 | 10/2009 | Kanner et al. |
| D611,144 S | 3/2010 | Reynolds |
| 2001/0007077 A1 | 7/2001 | Ginn et al. |
| 2001/0031972 A1 | 10/2001 | Robertson et al. |
| 2001/0046518 A1 | 11/2001 | Sawhney |
| 2001/0047180 A1 | 11/2001 | Grudem et al. |
| 2002/0026215 A1 | 2/2002 | Redmond et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049472 A1 | 4/2002 | Coleman et al. |
| 2002/0058960 A1 | 5/2002 | Hudson et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0193808 A1 | 12/2002 | Belef et al. |
| 2003/0004543 A1 | 1/2003 | Gleeson et al. |
| 2003/0009180 A1 | 1/2003 | Hinchliffe et al. |
| 2003/0009196 A1 | 1/2003 | Peterson |
| 2003/0032981 A1 | 2/2003 | Kanner et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0097140 A1 | 5/2003 | Kanner |

| | | | | | | |
|---|---|---|---|---|---|---|
| 2003/0109890 A1 | 6/2003 | Kanner et al. | | 2007/0049968 A1 | 3/2007 | Sibbitt, Jr. et al. |
| 2003/0125766 A1 | 7/2003 | Ding | | 2007/0060895 A1 | 3/2007 | Sibbitt, Jr. et al. |
| 2003/0158577 A1 | 8/2003 | Pantages et al. | | 2007/0060950 A1 | 3/2007 | Khosravi et al. |
| 2003/0158578 A1 | 8/2003 | Pantages et al. | | 2007/0123817 A1 | 5/2007 | Khosravi et al. |
| 2003/0195504 A1 | 10/2003 | Tallarida et al. | | 2007/0203506 A1 | 8/2007 | Sibbitt, Jr. et al. |
| 2003/0195561 A1 | 10/2003 | Carley et al. | | 2007/0250080 A1 | 10/2007 | Jones et al. |
| 2004/0009205 A1 | 1/2004 | Sawhney | | 2007/0270904 A1 | 11/2007 | Ginn |
| 2004/0009289 A1 | 1/2004 | Carley et al. | | 2007/0276416 A1 | 11/2007 | Ginn et al. |
| 2004/0010285 A1 | 1/2004 | Carley et al. | | 2007/0282352 A1 | 12/2007 | Carley et al. |
| 2004/0039414 A1 | 2/2004 | Carley et al. | | 2008/0004636 A1 | 1/2008 | Walberg |
| 2004/0073236 A1 | 4/2004 | Carley et al. | | 2008/0009794 A1 | 1/2008 | Bagaoisan et al. |
| 2004/0073255 A1 | 4/2004 | Ginn et al. | | 2008/0065151 A1 | 3/2008 | Ginn |
| 2004/0082906 A1 | 4/2004 | Tallarida et al. | | 2008/0065152 A1 | 3/2008 | Carley |
| 2004/0087985 A1 | 5/2004 | Loshakove et al. | | 2008/0086075 A1 | 4/2008 | Isik et al. |
| 2004/0092964 A1 | 5/2004 | Modesitt et al. | | 2008/0210737 A1 | 9/2008 | Ginn et al. |
| 2004/0092968 A1 | 5/2004 | Caro et al. | | 2008/0221616 A1 | 9/2008 | Ginn et al. |
| 2004/0093027 A1 | 5/2004 | Fabisiak et al. | | 2008/0269801 A1 | 10/2008 | Coleman et al. |
| 2004/0097978 A1 | 5/2004 | Modesitt et al. | | 2008/0269802 A1 | 10/2008 | Coleman et al. |
| 2004/0127940 A1 | 7/2004 | Ginn et al. | | 2008/0272173 A1 | 11/2008 | Coleman et al. |
| 2004/0143290 A1 | 7/2004 | Brightbill | | 2008/0312666 A1 | 12/2008 | Ellingwood et al. |
| 2004/0153122 A1 | 8/2004 | Palermo | | 2008/0312686 A1 | 12/2008 | Ellingwood |
| 2004/0153123 A1 | 8/2004 | Palermo et al. | | 2008/0319475 A1 | 12/2008 | Clark |
| 2004/0158127 A1 | 8/2004 | Okada | | 2009/0157101 A1 | 6/2009 | Reyes et al. |
| 2004/0158287 A1 | 8/2004 | Cragg et al. | | 2009/0157102 A1 | 6/2009 | Reynolds et al. |
| 2004/0167511 A1 | 8/2004 | Buehlmann et al. | | 2009/0177212 A1 | 7/2009 | Carley et al. |
| 2004/0167570 A1 | 8/2004 | Pantages | | 2009/0177213 A1 | 7/2009 | Carley et al. |
| 2004/0191277 A1 | 9/2004 | Sawhney et al. | | 2009/0254119 A1 | 10/2009 | Sibbitt, Jr. et al. |
| 2004/0215232 A1 | 10/2004 | Belhe et al. | | 2010/0130965 A1 | 5/2010 | Sibbitt, Jr. |
| 2004/0254591 A1 | 12/2004 | Kanner et al. | | | | |
| 2004/0267193 A1 | 12/2004 | Bagaoisan et al. | | FOREIGN PATENT DOCUMENTS | | |
| 2004/0267308 A1 | 12/2004 | Bagaoisan et al. | | | | |
| 2004/0267312 A1 | 12/2004 | Kanner et al. | | DE | 197 11 288 | 10/1998 |
| 2005/0059982 A1 | 3/2005 | Zung et al. | | DE | 29723736 U1 | 4/1999 |
| 2005/0075665 A1 | 4/2005 | Brenzel et al. | | DE | 19859952 | 2/2000 |
| 2005/0085851 A1 | 4/2005 | Fiehler et al. | | EP | 0 386 361 | 9/1990 |
| 2005/0085854 A1 | 4/2005 | Ginn | | EP | 0 534 696 | 3/1993 |
| 2005/0085855 A1 | 4/2005 | Forsberg | | EP | 0 756 851 | 2/1997 |
| 2005/0090859 A1 | 4/2005 | Ravlkumar | | EP | 0 774 237 | 5/1997 |
| 2005/0119695 A1 | 6/2005 | Carley et al. | | EP | 0 858 776 | 8/1998 |
| 2005/0121042 A1 | 6/2005 | Belhe et al. | | EP | 0 941 697 | 9/1999 |
| 2005/0149117 A1 | 7/2005 | Khosravi et al. | | FR | 2 443 238 | 7/1980 |
| 2005/0165357 A1 | 7/2005 | McGuckin et al. | | FR | 2 715 290 | 7/1995 |
| 2005/0177189 A1 | 8/2005 | Ginn et al. | | FR | 2 722 975 | 2/1996 |
| 2005/0216057 A1 | 9/2005 | Coleman et al. | | FR | 2 768 324 | 3/1999 |
| 2005/0222614 A1 | 10/2005 | Ginn et al. | | GB | 1 358 466 | 7/1974 |
| 2005/0234508 A1 | 10/2005 | Cummins et al. | | GB | 2 075 144 | 11/1981 |
| 2005/0245876 A1 | 11/2005 | Khosravi et al. | | IE | S2001/0547 | 7/2002 |
| 2005/0267528 A1 | 12/2005 | Ginn et al. | | IE | S2001/0815 | 7/2002 |
| 2005/0267530 A1 | 12/2005 | Cummins et al. | | IE | S2001/0748 | 8/2002 |
| 2005/0273136 A1 | 12/2005 | Belef et al. | | IE | S2001/0749 | 8/2002 |
| 2005/0273137 A1 | 12/2005 | Ginn | | IE | S2002/0452 | 12/2002 |
| 2005/0274768 A1 | 12/2005 | Cummins et al. | | IE | S2002/0664 | 2/2003 |
| 2005/0283188 A1 | 12/2005 | Loshakove et al. | | IE | S2002/0665 | 2/2003 |
| 2006/0020270 A1 | 1/2006 | Jabba et al. | | IE | S2001/0451 | 7/2003 |
| 2006/0034930 A1 | 2/2006 | Khosravi et al. | | IE | S2002/0552 | 7/2003 |
| 2006/0047313 A1 | 3/2006 | Khanna et al. | | IE | S2003/0424 | 12/2003 |
| 2006/0100664 A1 | 5/2006 | Pai et al. | | IE | S2003/0490 | 1/2004 |
| 2006/0135989 A1 | 6/2006 | Carley et al. | | IE | S2000/0722 | 10/2004 |
| 2006/0144479 A1 | 7/2006 | Carley et al. | | IE | S2000/0724 | 10/2004 |
| 2006/0167484 A1 | 7/2006 | Carley et al. | | IE | S2004/0368 | 11/2005 |
| 2006/0190014 A1 | 8/2006 | Ginn et al. | | IE | S2005/0342 | 11/2005 |
| 2006/0190037 A1 | 8/2006 | Carley et al. | | JP | 58-181006 | 12/1983 |
| 2006/0190038 A1 | 8/2006 | Carley et al. | | JP | 1 274750 | 11/1989 |
| 2006/0195123 A1 | 8/2006 | Ginn et al. | | JP | 11500642 | 8/1997 |
| 2006/0195124 A1 | 8/2006 | Ginn et al. | | JP | 2000102546 | 4/2000 |
| 2006/0253037 A1 | 11/2006 | Ginn et al. | | NL | 9302140 | 7/1995 |
| 2006/0253072 A1 | 11/2006 | Pai et al. | | PL | 171425 | 4/1997 |
| 2006/0265012 A1 | 11/2006 | Anderson | | RU | 2086192 | 8/1997 |
| 2006/0287674 A1 | 12/2006 | Ginn et al. | | SU | 197801 | 6/1967 |
| 2007/0010853 A1 | 1/2007 | Ginn et al. | | SU | 495067 | 12/1975 |
| 2007/0010854 A1 | 1/2007 | Cummins et al. | | SU | 1324650 | 7/1978 |
| 2007/0021778 A1 | 1/2007 | Carly | | SU | 912155 | 3/1982 |
| 2007/0049967 A1 | 3/2007 | Sibbitt, Jr. et al. | | SU | 1243708 | 7/1986 |

| | | |
|---|---|---|
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45594 | 6/2002 |
| WO | WO 02/062234 | 8/2002 |
| WO | WO 02/98302 | 12/2002 |
| WO | WO 03/013363 | 2/2003 |
| WO | WO 03/013364 | 2/2003 |
| WO | WO 02/45593 | 6/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/060169 | 7/2004 |
| WO | WO 2004/069054 | 8/2004 |
| WO | WO 2005/000126 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2008/031102 | 3/2008 |
| WO | WO 2009/079091 | 6/2009 |
| WO | WO 2010/031050 | 3/2010 |
| ZA | 200100527 | 1/2001 |
| ZA | 200100528 | 1/2001 |

OTHER PUBLICATIONS

U.S. Appl. No. 10/541,083, Feb. 5, 2010, Notice of Allowance.
U.S. Appl. No. 10/638,115, Dec. 1, 2009, Notice of Allowance.
U.S. Appl. No. 10/787,073, Feb. 17, 2010, Notice of Allowance.
U.S. Appl. No. 10/908,721, Feb. 2, 2010, Office Action.
U.S. Appl. No. 29/296,370, Aug. 18, 2008, Office Action.
U.S. Appl. No. 29/296370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 60/969,069, filed Jul. 1, 2005, Pantages et al.
U.S. Appl. No. 60/693,531, filed Jun. 24, 2005, Carly.
U.S. Appl. No. 60/843,325, filed Sep. 8, 2006, Carly.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 12/113,092, filed Apr. 30, 2008, Ginn et al.
U.S. Appl. No. 12/393,877, filed Feb. 26, 2009, Ellingwood et al.
U.S. Appl. No. 12/403,277, filed Mar. 12, 2009, Coleman et al.
"Hand tool for forming telephone connections - comprises pliers with reciprocably driven ram crimping clip around conductors against anvil", Derwent-ACC-No: 1978-B8090A.
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
Deepak Mital et al, Renal Transplantation Without Sutures Using the Vascular Clipping System for Rental Artery and Vein Anastomosis - A New Technique, Transplantation Issue, Oct 1996, pp. 1171-1173, vol. 62 - No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77 - No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6 - No. 6, Department of Surgery, Uniformed Services University of the Health Sciences, Bethesda, MD.
G Gershony et al, Novel Vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial punture sites, American journal of cardiology, Aug. 1993, pp. 445-449, vol. 72 - No. 5, Department of Cardiology, Academic Hospital Maastricht, the Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5 - No. 2, Division of Obstetrics and Gynecology, University of Chicago, Chicago, IL.
J. Findlay et al, Carotid Arteriotomy Closure Using a Vascular Clip System, Neurosurgery, Mar. 1998, pp. 550-554, vol. 42 - No. 3, Division of Neurosurgery, University of Alberta, Edmonton, Canada.
Jeremy L Gilbert PHD, Wound Closure Biomaterials and Devices, Schock., Mar. 1999, p. 226, vol. 11- No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.

K Narayanan et al, Simultaneous primary closure of four fasciotomy wounds in a single setting using the Sure-Closure device, Injury, Jul. 1996, pp. 449-451, vol. 27 -No. 6, Department of Surgery, Mercy Hospital of Pittsburgh, PA.

Marshall A.C., Lock J.E., Structural and Compliant Anatomy of the Patent Foramen Ovale in Patients Undergoing Transcatheter Closure, Am Heart J Aug. 2000; 140(2); pp. 303-307.

McCarthy, et al., "Tension (Stay) Suture Bridge", J. of International College of Surgeons, 34(5), pp. 613-614 (Nov. 1960). cited by other.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct 1996, pp. 329-332, vol. 6 - No. 5, Orlando Regional Medical Center, FL.

Michael Gianturco, A Play on Catheterization, Forbes, Dec. 1996, p. 146, vol. 158 - No. 15.

Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183 - No. 4.

P M N Werker, et al, Review of facilitated approaches to vascular anastomosis surgery, Conference: Utrecht MICABG Workshop 2, The Annals of thoracic surgery, Apr. 1996, pp. S122-127, vol. 63 - No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45 - No. 6, Institution from the Department of Surgery, Washington Hospital Center, Washington DC, and Uniformed Services University of the Health Sciences, Bethesda, Maryland.

ProstarXL - Percutaneous Vascular Surgical Device, www.Archive. org, Jun. 1998, Original Publisher: http://prostar.com, may also be found at http://web.archive.org/web/19980630040429/www.perclose.com/html/prstrxl.html.

Sa Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19 - No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83 - No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25. - No. 2, Supplement 1.

Stretch Comb by Scunci, retrieved via internet at www.scunci.com/productdetail by examiner on Oct. 9, 2007, publication date unavailable.

Swee Lian Tan, MD, PHD, FACS, Explanation of Infected Hemostatic Puncture Closure Devices - A Case Report, Vascular and Endovascular Surgery, 1999, pp. 507-510, vol. 33 - No. 5, Parkland Medical Center, Derry, New Hampshire.

Sy Nakada et al, Comparison of newer laparoscopic port closure techniques in the porcine model, J Endourol, Oct. 1995, pp. 397-401, vol. 9 - No. 5, Department of Surgery/Urology, University of Wisconsin Medical School, Madison.

Taber's Cyclopedic Medical Dictionary, 18th Ed. 1997, pp. 747 and 1420.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42 - No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5 - No. 3-4.

Ut Aker et al, Immediate arterial hemostasis after cardiac catheterization: initial experience with a new puncture closure device, Cathet Cardiovasc Diagn, Mar. 1994, pp. 228-232, vol. 33 - No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19 - No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25 - No. 7.

U.S. Appl. No. 09/478,179, filed Nov. 6, 2000, Notice of Allowance.
U.S. Appl. No. 09/478,179, filed Feb. 15, 2001, Issue Notification.
U.S. Appl. No. 09/546,998, filed May 6, 2002, Notice of Allowance.
U.S. Appl. No. 09/546,998, filed Sep. 19, 2002, Issue Notification.
U.S. Appl. No. 09/610,238, filed Mar. 26, 2001, Notice of Allowance.
U.S. Appl. No. 09/610,238, filed Sep. 5, 2001, Office Action.
U.S. Appl. No. 09/610,238, filed Feb. 11, 2002, Notice of Allowance.
U.S. Appl. No. 09/610,238, filed May 03, 2002, Issue Notification.
U.S. Appl. No. 09/680,837, filed Jul. 9, 2002, Office Action.
U.S. Appl. No. 09/680,837, filed Nov. 6, 2002, Office Action.
U.S. Appl. No. 09/680,837, filed Mar. 25, 2003, Office Action.
U.S. Appl. No. 09/680,837, filed Jun. 16, 2003, Notice of Allowance.
U.S. Appl. No. 09/680, 837, filed Sep. 11, 2003, Issue Notification.
U.S. Appl. No. 09/732,178, filed Aug. 1, 2002, Office Action.
U.S. Appl. No. 09/732,178, filed Dec. 24, 2002, Office Action.
U.S. Appl. No. 09/732,178, filed Jun. 10, 2003, Advisory Action.
U.S. Appl. No. 09/732,178, filed Jul. 3, 2003, Office Action.
U.S. Appl. No. 09/732,178, filed Nov. 17, 2003, Notice of Allowance.
U.S. Appl. No. 09/732,178, filed Mar. 25, 2004, Issue Notification.
U.S. Appl. No. 09/732,835, filed Sep. 11, 2003, Office Action.
U.S. Appl. No. 09/732,835, filed Feb. 9, 2004, Office Action.
U.S. Appl. No. 09/732,835, filed Mar. 17, 2004, Notice of Allowance.
U.S. Appl. No. 09/764,813, filed Mar. 26, 2001, Office Action.
U.S. Appl. No. 09/764,813, filed Jun. 4, 2001, Notice of Allowance.
U.S. Appl. No. 09/764,813, filed Aug. 6, 2001, Issue Notification.
U.S. Appl. No. 09/933,299, filed Feb. 26, 2003, Office Action.
U.S. Appl. No. 09/933,299, filed Jun. 16, 2003, Notice of Allowance.
U.S. Appl. No. 09/933,299, filed Sep. 25, 2003, Issue Notification.
U.S. Appl. No. 09/948,813, filed Jan. 31, 2003, filed Notice of Allowance.
U.S. Appl. No. 09/948,813, filed Jun. 5, 2003, Issue Notification.
U.S. Appl. No. 09/949,398, filed Mar. 4, 2003, Office Action.
U.S. Appl. No. 09/949,398, filed Jul. 28, 2003, Notice of Allowance.
U.S. Appl. No. 09/949,398, filed Dec. 11, 2003, Issue Notification.
U.S. Appl. No. 09/949,438, filed Dec. 17, 2002, Office Action.
U.S. Appl. No. 09/949,438, filed Apr. 21, 2003, Notice of Allowance.
U.S. Appl. No. 09/949,438, filed Aug. 21, 2003, Issue Notification.
U.S. Appl. No. 10/006,400, filed Aug. 27, 2004, Office Action.
U.S. Appl. No. 10/006,400, filed Feb. 23, 2005, Office Action.
U.S. Appl. No. 10/006,400, filed Apr. 11, 2005, Office Action.
U.S. Appl. No. 10/006,400, filed Jul. 27, 2005, Office Action.
U.S. Appl. No. 10/006,400, filed Mar. 6, 2006, Office Action.
U.S. Appl. No. 10/006,400, filed May 24, 2006, Office Action.
U.S. Appl. No. 10/006,400, filed Oct. 26, 2006, Office Action.
U.S. Appl. No. 10/006,400, filed Apr. 19, 2007, Office Action.
U.S. Appl. No. 10/006,400, filed Apr. 2, 2008, Office Action.
U.S. Appl. No. 10/006,400, filed Jan. 2, 2009, Office Action.
U.S. Appl. No. 10/006,400, filed Jul. 9, 2009, Notice of Allowance.
U.S. Appl. No. 10/006,400, filed Jan. 13, 2010, Notice of Allowance.
U.S. Appl. No. 10/081,717, filed Sep. 29, 2003, Notice of Allowance.
U.S. Appl. No. 10/081,717, filed Feb. 5, 2004, Issue Notification.
U.S. Appl. No. 10/081,723, filed Sep. 29, 2004, Office Action.
U.S. Appl. No. 10/081,723, filed May 13, 2005, Notice of Allowance.

U.S. Appl. No. 10/081,725, filed Feb. 9, 2004, Notice of Allowance.
U.S. Appl. No. 10/081,725, filed Apr. 13, 2004, Office Action.
U.S. Appl. No. 10/081,725, filed May 27, 2004, Issue Notification.
U.S. Appl. No. 10/081,726, filed Apr. 11, 2003, Notice of Allowance.
U.S. Appl. No. 10/081,726, filed Jun. 9, 2003, Examiners Amendment.
U.S. Appl. No. 10/081,726, filed Sep. 4, 2003, Issue Notification.
U.S. Appl. No. 10/147,774, filed Nov. 4, 2004, Office Action.
U.S. Appl. No. 10/147,774, filed May 4, 2005, Office Action.
U.S. Appl. No. 10/147,774, filed Oct. 18, 2005, Office Action.
U.S. Appl. No. 10/147,774, filed Apr. 18, 2007, Notice of Allowance.
U.S. Appl. No. 10/147,774, filed Sep. 27, 2007, Notice of Allowance.
U.S. Appl. No. 10/147,774, filed Feb. 4, 2008, Notice of Allowance.
U.S. Appl. No. 10/147,774, filed Jun. 30, 2008, Office Action.
U.S. Appl. No. 10/147,774, filed Mar. 18, 2009, Office Action.
U.S. Appl. No. 10/147,774, filed Oct. 26, 2009, Office Action.
U.S. Appl. No. 10/240,183, filed Jul. 27, 2004, Office Action.
U.S. Appl. No. 10/240,183, filed Dec. 17, 2004, Office Action.
U.S. Appl. No. 10/240,183, filed Mar. 9, 2005, Notice of Allowance.
U.S. Appl. No. 10/240,183, filed Aug. 11, 2006, Examiners Response to Rule 312.
U.S. Appl. No. 10/264,306, filed Feb. 9, 2005, Office Action.
U.S. Appl. No. 10/264,306, filed May 26, 2005, Office Action.
U.S. Appl. No. 10/264,306, filed Oct. 4, 2005, Office Action.
U.S. Appl. No. 10/264,306, filed May 10, 2006, Notice of Allowance.
U.S. Appl. No. 10/264,306, filed Jul. 2, 2007, Notice of Allowance.
U.S. Appl. No. 10/264,306, filed Feb. 4, 2008, Notice of Allowance.
U.S. Appl. No. 10/264,306, filed Jun. 27, 2008, Office Action.
U.S. Appl. No. 10/264,306, filed Feb. 26, 2009, Office Action.
U.S. Appl. No. 10/264,306, filed Aug. 13, 2009, Office Action.
U.S. Appl. No. 10/305,923, filed Nov. 1, 2004, Office Action.
U.S. Appl. No. 10/305,923, filed Mar. 3, 2005, Notice of Allowance.
U.S. Appl. No. 10/335,075, filed Aug. 10, 2005, Office Action.
U.S. Appl. No. 10/335,075, filed Dec. 19, 2005, Office Action.
U.S. Appl. No. 10/335,075, filed Apr. 21, 2006, Office Action.
U.S. Appl. No. 10/335,075, filed Dec. 27, 2006, Notice of Allowance.
U.S. Appl. No. 10/335,075, filed Apr. 11, 2007, Issue Notification.
U.S. Appl. No. 10/356,214, filed Nov. 30, 2005, Office Action.
U.S. Appl. No. 10/356,214, filed Aug. 23, 2006, Office Action.
U.S. Appl. No. 10/356,214, filed Feb. 13, 2007, Office Action.
U.S. Appl. No. 10/356,214, filed Sep. 12, 2007, Office Action.
U.S. Appl. No. 10/356,214, filed Mar. 6, 2008, Office Action.
U.S. Appl. No. 10/356,214, filed Nov. 4, 2008, Office Action.
U.S. Appl. No. 10/356,214, filed Apr. 29, 2009, Office Action.
U.S. Appl. No. 10/356,214, filed Jan. 13, 2010, Notice of Allowance.
U.S. Appl. No. 10/435,104, filed Jun. 10, 2004, Office Action.
U.S. Appl. No. 10/435,104, filed Sep. 21, 2004, Notice of Allowance.
U.S. Appl. No. 10/435,104, filed Jan. 3, 2006, Examiners Amendment.
U.S. Appl. No. 10/435,104, filed Feb. 15, 2006, Issue Notification.
U.S. Appl. No. 10/435,104, filed May 16, 2006, Office Action.
U.S. Appl. No. 10/435,104, filed Dec. 28, 2006, Notice of Allowance.
U.S. Appl. No. 10/435,104, filed May 23, 2007, Issue Notification.
U.S. Appl. No. 10/435,104, filed Jul. 10, 2007, Notice of Allowance.
U.S. Appl. No. 10/435,104, filed Aug. 2, 2007, Notice of Allowance.
U.S. Appl. No. 10/435,104, filed Oct. 26, 2007, Notice of Allowance.
U.S. Appl. No. 10/435,104, filed Nov. 14, 2007, Supplemental Notice of Allowance.
U.S. Appl. No. 10/435,104, filed Apr. 4, 2008, Notice of Allowance.
U.S. Appl. No. 10/435,104, filed Sep. 26, 2008, Notice of Allowance.
U.S. Appl. No. 10/435,104, filed Dec. 22, 2008, Supplemental Notice of Allowance.
U.S. Appl. No. 10/435,104, filed Jan. 20, 2010, Notice of Allowance.
U.S. Appl. No. 10/455,768, filed Nov. 16, 2004, Office Action.
U.S. Appl. No. 10/455,768, filed Apr. 6, 2005, Notice of Allowance.
U.S. Appl. No. 10/486,067, filed Jan. 10, 2006, Office Action.
U.S. Appl. No. 10/486,067, filed Sep. 20, 2006, Notice of Allowance.
U.S. Appl. No. 10/486,067, filed Dec. 27, 2006, Issue Notification.
U.S. Appl. No. 10/486,070, filed Apr. 20, 2005, Office Action.
U.S. Appl. No. 10/486,070, filed Aug. 10, 2005, Office Action.
U.S. Appl. No. 10/486,070, filed Oct. 18, 2005, Notice of Allowance.
U.S. Appl. No. 10/517,004, filed Aug. 13, 2007, Office Action.
U.S. Appl. No. 10/517,004, filed Jan. 30, 2008, Office Action.
U.S. Appl. No. 10/517,004, filed Aug. 13, 2008, Notice of Allowance.
U.S. Appl. No. 10/517,004, filed Feb. 10, 2009, Notice of Allowance.
U.S. Appl. No. 10/517,004, filed Mar. 24, 2009, Supplemental Notice of Allowance.
U.S. Appl. No. 10/517,004, filed Jun. 26, 2009, Notice of Allowance.
U.S. Appl. No. 10/517,004, filed Jan. 11, 2010, Notice of Allowance.
U.S. Appl. No. 10/519,778, filed Feb. 23, 2006, Office Action.
U.S. Appl. No. 10/519,778, filed May 31, 2006, Notice of Allowance.
U.S. Appl. No. 10/541,083, filed Oct. 16, 2007, Office Action.
U.S. Appl. No. 10/541,083, filed Oct. 31, 2007, Office Action.
U.S. Appl. No. 10/541,083, filed May 5, 2008, Office Action.
U.S. Appl. No. 10/541,083, filed Sep. 19, 2008, Notice of Allowance.
U.S. Appl. No. 10/541,083, filed Dec. 29, 2008, Notice of Allowance.
U.S. Appl. No. 10/541,083, filed Apr. 16, 2009, Notice of Allowance.
U.S. Appl. No. 10/616,832, filed Jun. 30, 2006, Office Action.
U.S. Appl. No. 10/616,832, filed Oct. 20, 2006, Office Action.
U.S. Appl. No. 10/616,832, filed May 29, 2007, Office Action.
U.S. Appl. No. 10/616,832, filed Jan. 22, 2008, Office Action.
U.S. Appl. No. 10/616,832, filed Jan. 11, 2010, Notice of Allowance.
U.S. Appl. No. 10/541,083, filed Sep. 30, 2009, Notice of Allowance.
U.S. Appl. No. 10/616,832, filed Sep. 17, 2008, Office Action.
U.S. Appl. No. 10/616,832, filed Jul. 21, 2009, Office Action.
U.S. Appl. No. 10/617,090, filed Mar. 22, 2005, Office Action.
U.S. Appl. No. 10/617,090, filed Jul. 6, 2005, Notice of Allowance.
U.S. Appl. No. 10/617,090, filed Oct. 5, 2005, Notice of Allowance.
U.S. Appl. No. 10/617,090, filed Feb. 1, 2006, Issue Notification.
U.S. Appl. No. 10/638,115, filed Sep. 22, 2006, Restriction Requirement.
U.S. Appl. No. 10/638,115, filed Jan. 31, 2007, Office Action.
U.S. Appl. No. 10/638,115, filed Sep. 18, 2007, Office Action.
U.S. Appl. No. 10/638,115, filed Feb. 7, 2008, Office Action.
U.S. Appl. No. 10/638,115, filed Oct. 29, 2008, Office Action.
U.S. Appl. No. 10/638,115, filed May 7, 2009, Notice of Allowance.
U.S. Appl. No. 10/667,144, filed Sep. 19, 2006, Office Action.
U.S. Appl. No. 10/667,144, filed May 2, 2007, Office Action.
U.S. Appl. No. 10/667,144, filed Nov. 19, 2007, Office Action.
U.S. Appl. No. 10/667,144, filed Dec. 5, 2007, Office Action.
U.S. Appl. No. 10/667,144, filed May 12, 2008, Office Action.
U.S. Appl. No. 10/667,144, filed Mar. 24, 2009, Office Action.
U.S. Appl. No. 10/667,144, filed Nov. 23, 2009, Office Action.
U.S. Appl. No. 10/669,313, filed Jan. 11, 2006, Notice of Allowance.
U.S. Appl. No. 10/669,313, filed Jun. 28, 2006, Notice of Allowance.
U.S. Appl. No. 10/669,313, filed Nov. 15, 2006, Issue Notification.
U.S. Appl. No. 10/682,459, filed Sep. 15, 2006, Office Action.
U.S. Appl. No. 10/682,459, filed Apr. 18, 2007, Office Action.
U.S. Appl. No. 10/682,459, filed Apr. 2, 2008, Office Action.
U.S. Appl. No. 10/682,459, filed Dec. 4, 2008, Office Action.
U.S. Appl. No. 10/682,459, filed Jun. 10, 2009, Office Action.
U.S. Appl. No. 10/682,459, filed Dec. 23, 2009, Office Action.
U.S. Appl. No. 10/786,444, filed Oct. 30, 2006, Office Action.
U.S. Appl. No. 10/786,444, filed Apr. 17, 2007, Office Action.
U.S. Appl. No. 10/786,444, filed Aug. 31, 2007, Office Action.
U.S. Appl. No. 10/786,444, filed Apr. 24, 2008, Office Action.
U.S. Appl. No. 10/786,444, filed Oct. 17, 2008, Office Action.
U.S. Appl. No. 10/786,444, filed Jun. 18, 2009, Office Action.
U.S. Appl. No. 10/786,444, filed Jan. 14, 2010, Office Action.
U.S. Appl. No. 10/787,073, filed Nov. 30, 2006, Office Action.
U.S. Appl. No. 10/787,073, filed Sep. 5, 2007, Office Action.
U.S. Appl. No. 10/787,073, filed Feb. 22, 2008, Office Action.
U.S. Appl. No. 10/787,073, filed Nov. 12, 2008, Office Action.
U.S. Appl. No. 10/787,073, filed Aug. 13, 2009, Office Action.
U.S. Appl. No. 10/908,721, filed Oct. 19, 2006, Office Action.
U.S. Appl. No. 10/908,721, filed Aug. 10, 2007, Office Action.
U.S. Appl. No. 10/908,721, filed Jan. 25, 2008, Office Action.
U.S. Appl. No. 10/908,721, filed Nov. 25, 2008, Office Action.
U.S. Appl. No. 10/908,721, filed Jun. 23, 2009, Office Action.
U.S. Appl. No. 11/048,503, filed Mar. 13, 2009, Office Action.
U.S. Appl. No. 11/048,503, filed Jun. 26, 2009, Office Action.
U.S. Appl. No. 11/048,503, filed Jan. 11, 2010, Notice of Allowance.
U.S. Appl. No. 11/113,549, filed Feb. 6, 2007, Office Action.
U.S. Appl. No. 11/113,549, filed May 30, 2007, Office Action.
U.S. Appl. No. 11/113,549, filed Nov. 9, 2007, Office Action.
U.S. Appl. No. 11/113,549, filed Apr. 16, 2008, Office Action.

U.S. Appl. No. 11/113,549, filed Jul. 21, 2009, Office Action.
U.S. Appl. No. 11/152,562, filed May 13, 2008, Office Action.
U.S. Appl. No. 11/152,562, filed Feb. 13, 2009, Office Action.
U.S. Appl. No. 11/152,562, filed Jul. 6, 2009, Office Action.
U.S. Appl. No. 11/198,811, filed Aug. 26, 2008, Office Action.
U.S. Appl. No. 11/198,811, filed Apr. 6, 2009, Office Action.
U.S. Appl. No. 11/198,811, filed Sep. 22, 2009, Office Action.
U.S. Appl. No. 11/344,793, filed Jan. 22, 2009, Office Action.
U.S. Appl. No. 11/344,868, filed Mar. 25, 2009, Office Action.
U.S. Appl. No. 11/344,891, filed Apr. 29, 2008, Office Action.
U.S. Appl. No. 11/344,891, filed Dec. 8, 2008, Office Action.
U.S. Appl. No. 11/344,891, filed Feb. 26, 2009, Office Action.
U.S. Appl. No. 11/344,891, filed Oct. 7, 2009, Office Action.
U.S. Appl. No. 11/390,586, filed Jun. 24, 2009, Office Action.
U.S. Appl. No. 11/396,141, filed May 22, 2009, Restriction Requirement.
U.S. Appl. No. 11/396,141, filed Aug. 26, 2009, Office Action.
U.S. Appl. No. 11/396,731, filed Feb. 13, 2009, Office Action.
U.S. Appl. No. 11/396,731, filed May 22, 2009, Office Action.
U.S. Appl. No. 11/406,203, filed May 14, 2007, Office Action.
U.S. Appl. No. 11/406,203, filed Jan. 29, 2008, Notice of Allowance.
U.S. Appl. No. 11/406,203, filed May 23, 2008, Notice of Allowance.
U.S. Appl. No. 11/406,203, filed Sep. 22, 2008, Notice of Allowance.
U.S. Appl. No. 11/406,203, filed Mar. 3, 2009, Office Action.
U.S. Appl. No. 11/406,203, filed Sep. 16, 2009, Office Action.
U.S. Appl. No. 11/411,925, filed Jun. 6, 2007, Office Action.
U.S. Appl. No. 11/411,925, filed Feb. 5, 2008, Office Action.
U.S. Appl. No. 11/411,925, filed Jan. 12, 2009, Office Action.
U.S. Appl. No. 11/411,925, filed Sep. 10, 2009, Office Action.
U.S. Appl. No. 11/427,297, filed Jan. 30, 2009, Office Action.
U.S. Appl. No. 11/427,297, filed Sep. 15, 2009, Office Action.
U.S. Appl. No. 11/455,993, filed Feb. 17, 2009, Office Action.
U.S. Appl. No. 11/455,993, filed Dec. 16, 2009, Office Action.
U.S. Appl. No. 11/461,323, filed May 2, 2007, Office Action.
U.S. Appl. No. 11/461,323, filed Oct. 29, 2007, Office Action.
U.S. Appl. No. 11/461,323, filed Apr. 25, 2008, Office Action.
U.S. Appl. No. 11/461,323, filed Nov. 6, 2008, Office Action.
U.S. Appl. No. 11/461,323, filed Jul. 27, 2009, Office Action.
U.S. Appl. No. 11/532,325, filed Feb. 23, 2009, Office Action.
U.S. Appl. No. 11/532,325, filed Jun. 17, 2009, Office Action.
U.S. Appl. No. 11/532,325, filed Jan. 5, 2010, Office Action.
U.S. Appl. No. 11/675,462, filed Dec. 10, 2009, Office Action.
U.S. Appl. No. 11/744,089, filed Nov. 26, 2008, Office Action.
U.S. Appl. No. 11/744,089, filed Aug. 14, 2009, Office Action.
U.S. Appl. No. 11/958,295, filed Aug. 27, 2009, Office Action.
U.S. Appl. No. 12/106,937, filed Mar. 30, 2009, Office Action.
U.S. Appl. No. 12/106,937, filed Nov. 18, 2009, Office Action.
U.S. Appl. No. 12/106,928, filed Jan. 23, 2009, Office Action.
U.S. Appl. No. 12/106,928, filed Oct. 5, 2009, Office Action.
U.S. Appl. No. 12/403,256, filed Dec. 16, 2009, Restriction Requirement.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.
U.S. Appl. No. 60/793,444, filed Apr. 20, 2006, Jones et al.
U.S. Appl. No. 61/097,072, filed Sep. 15, 2008, Sibbett, Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 10/006,400, filed Apr. 27, 2010, Notice of Allowance.
U.S. Appl. No. 10/147,774, filed Jun. 8, 2010, Office Action.
U.S. Appl. No. 10/264,306, filed Jun. 15, 2010, Office Action.
U.S. Appl. No. 10/356,214, filed May 13, 2010, Notice of Allowance.
U.S. Appl. No. 10/435,104, filed Jun. 2, 2010, Office Action.
U.S. Appl. No. 10/517,004, filed Apr. 23, 2010, Notice of Allowance.
U.S. Appl. No. 10/541,083, filed May 10, 2010, Notice of Allowance.
U.S. Appl. No. 10/616,832, filed May 12, 2010, Notice of Allowance.
U.S. Appl. No. 10/638,115, filed Apr. 2, 2010, Notice of Allowance.
U.S. Appl. No. 10/667,144, filed Jun. 22, 2010, Office Action.
U.S. Appl. No. 10/682,459, filed Apr. 28, 2010, Office Action.
U.S. Appl. No. 11/048,503, filed Apr. 26, 2010, Notice of Allowance.
U.S. Appl. No. 11/152,562, filed Mar. 31, 2010, Office Action.
U.S. Appl. No. 11/198,811, filed Jun. 29, 2010, Notice of Allowance.
U.S. Appl. No. 11/316,775, filed Apr. 16, 2008, Office Action.
U.S. Appl. No. 11/316,775, filed Aug. 6, 2008, Office Action.
U.S. Appl. No. 11/344,891, filed May 7, 2010, Office Action.
U.S. Appl. No. 11/390,586, filed Jul. 6, 2010, Office Action.
U.S. Appl. No. 11/396,141, filed May 4, 2010, Office Action.
U.S. Appl. No. 11/396,731, filed Jun. 29, 2010, Office Action.
U.S. Appl. No. 11/406,203, filed Jun. 18, 2010, Notice of Allowance.
U.S. Appl. No. 11/508,656, filed Dec. 9, 2009, Office Action.
U.S. Appl. No. 11/508,656, filed Mar. 25, 2010, Office Action.
U.S. Appl. No. 11/508,662, filed Dec. 28, 2009, Office Action.
U.S. Appl. No. 11/508,662, filed Apr. 14, 2010, Office Action.
U.S. Appl. No. 11/508,715, filed Jan. 6, 2010, Office Action.
U.S. Appl. No. 11/508,715, filed Apr. 26, 2010, Office Action.
U.S. Appl. No. 11/532,576, filed Mar. 1, 2010, Office Action.
U.S. Appl. No. 11/532,576, filed Apr. 23, 2010, Office Action.
U.S. Appl. No. 11/674,930, filed Jan. 8, 2009, Office Action.
U.S. Appl. No. 11/674,930, filed Jun. 4, 2009, Office Action.
U.S. Appl. No. 11/674,930, filed Jan. 8, 2010, Office Action.
U.S. Appl. No. 11/767,818, filed Dec. 24, 2009, Office Action.
U.S. Appl. No. 11/767,818, filed Mar. 22, 2010, Office Action.
U.S. Appl. No. 11/852,190, filed Jun. 24, 2010, Office Action.
U.S. Appl. No. 11/958,295, filed May 25, 2010, Office Action.
U.S. Appl. No. 12/106,928, filed May 10, 2010, Office Action.
U.S. Appl. No. 12/113,851, filed Apr. 27, 2010, Office Action.
U.S. Appl. No. 12/113,851, filed Jun. 24, 2010, Office Action.
U.S. Appl. No. 12/402,398, filed Mar. 9, 2010, Office Action.
U.S. Appl. No. 12/402,398, filed May 20, 2010, Office Action.
U.S. Appl. No. 12/403,256, filed Mar. 30, 2010, Office Action.

* cited by examiner

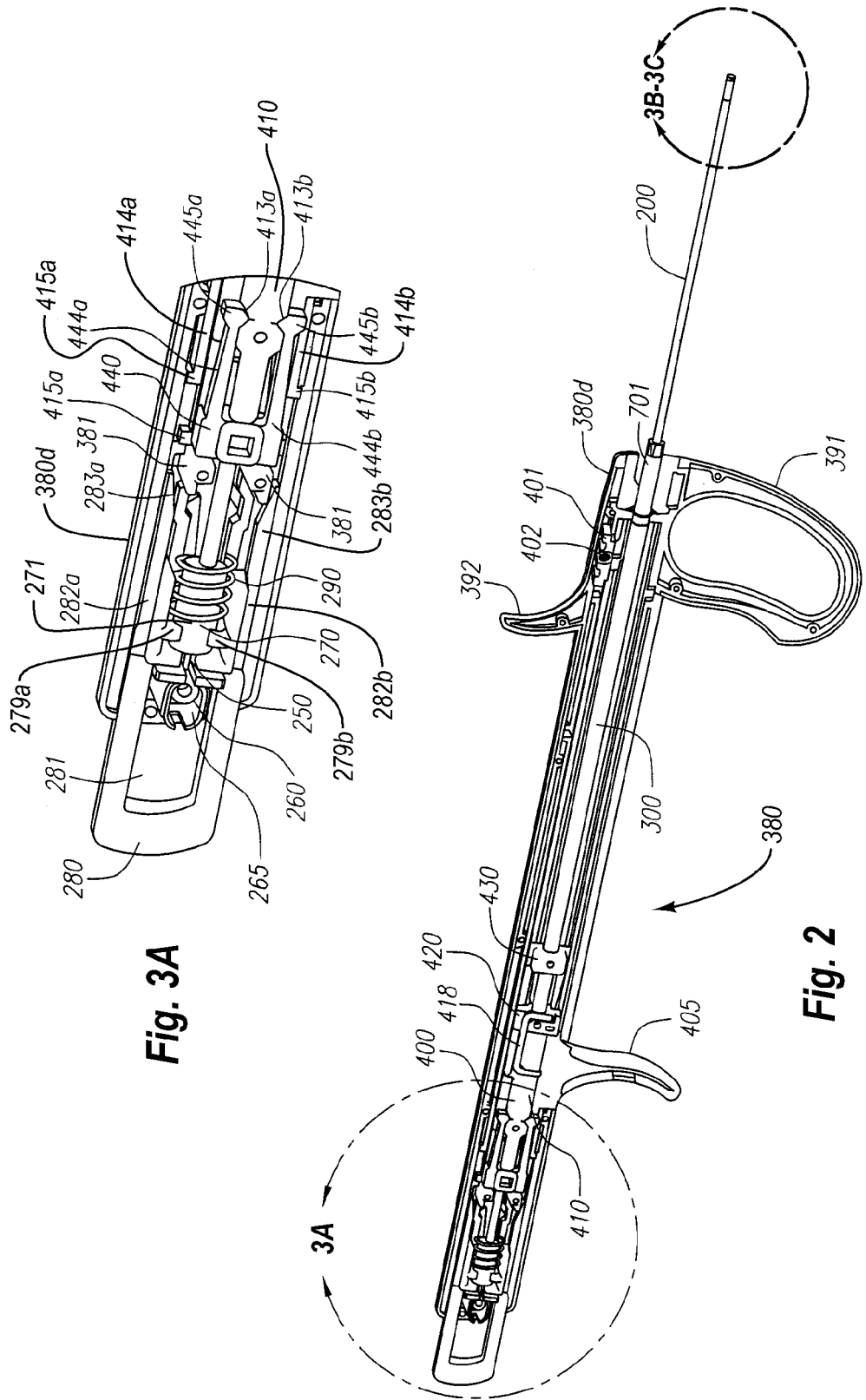

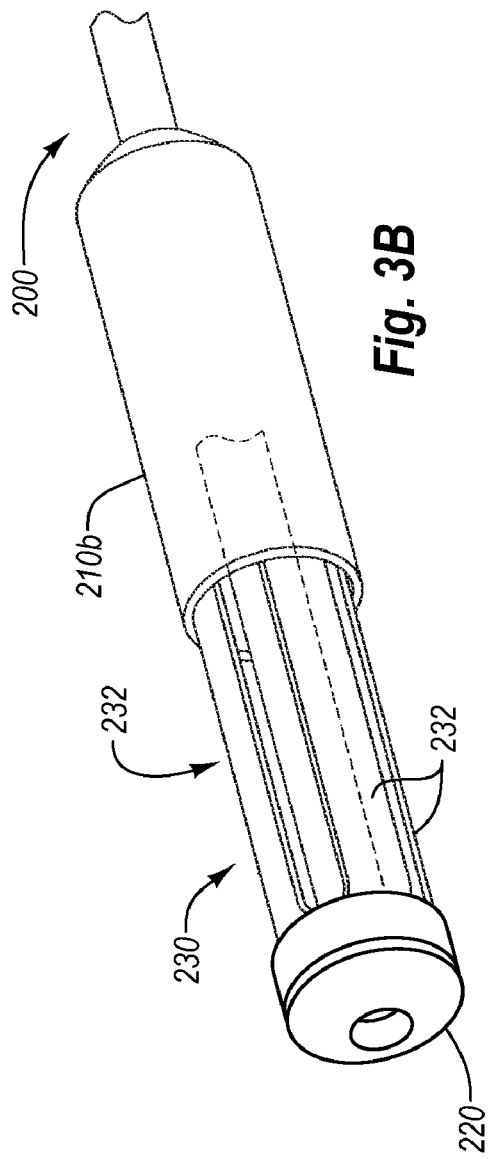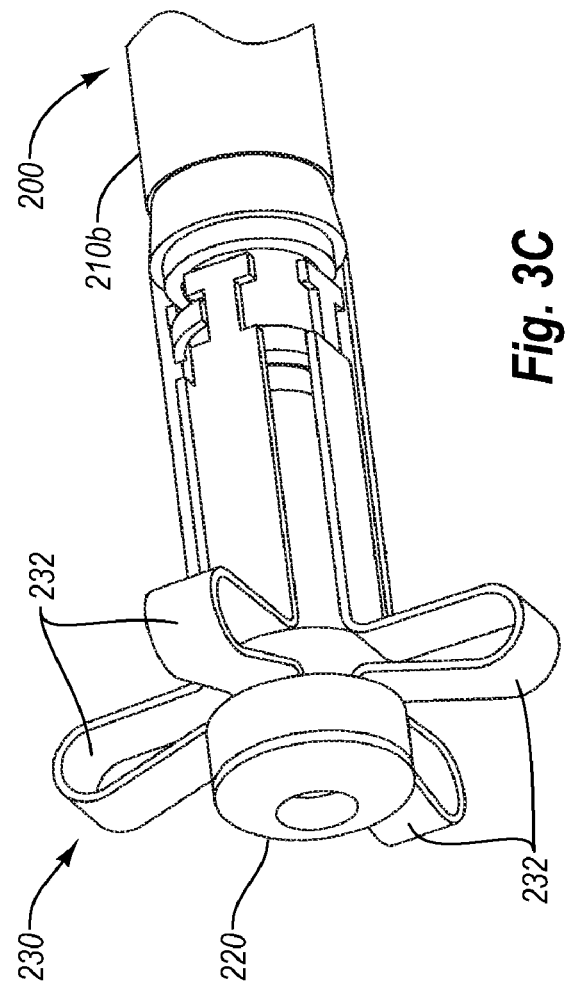

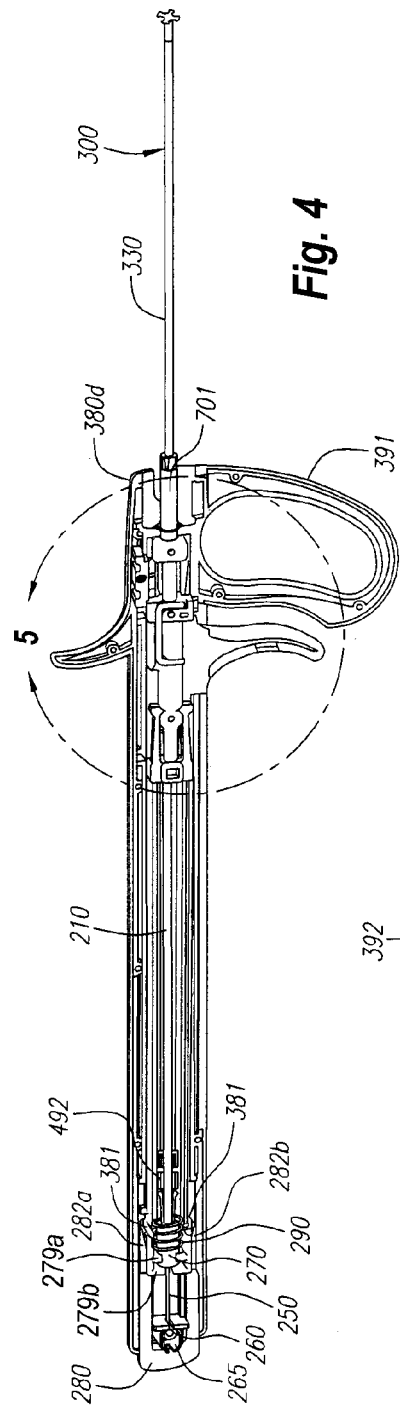
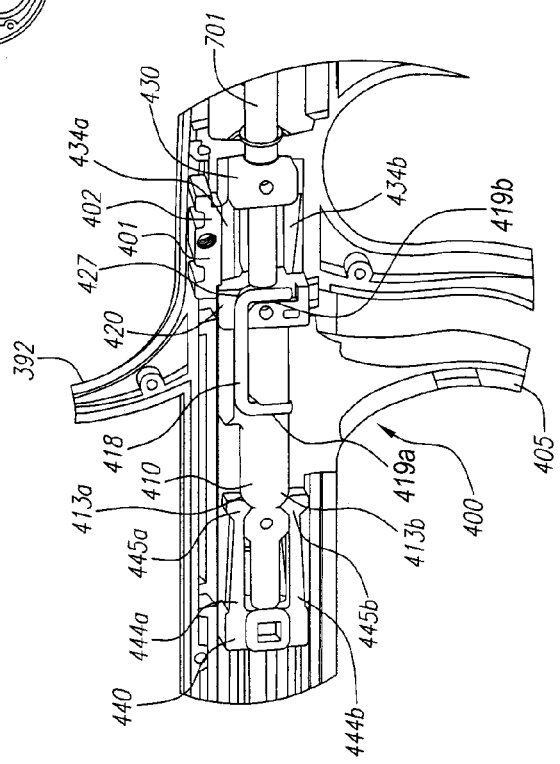

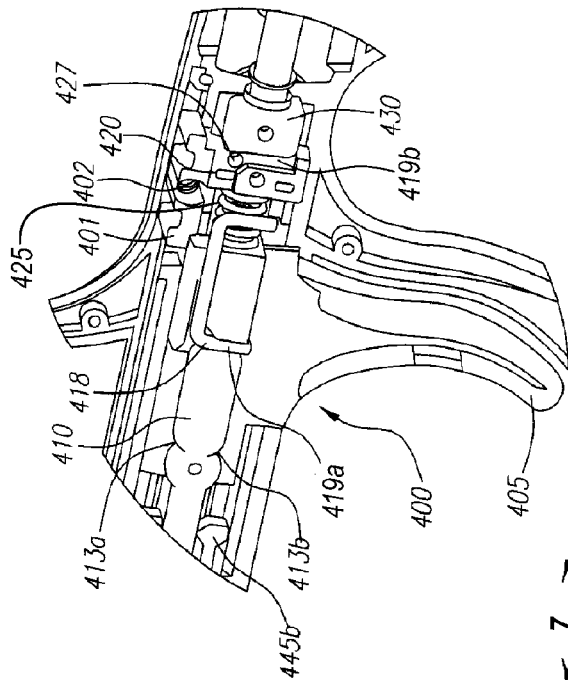
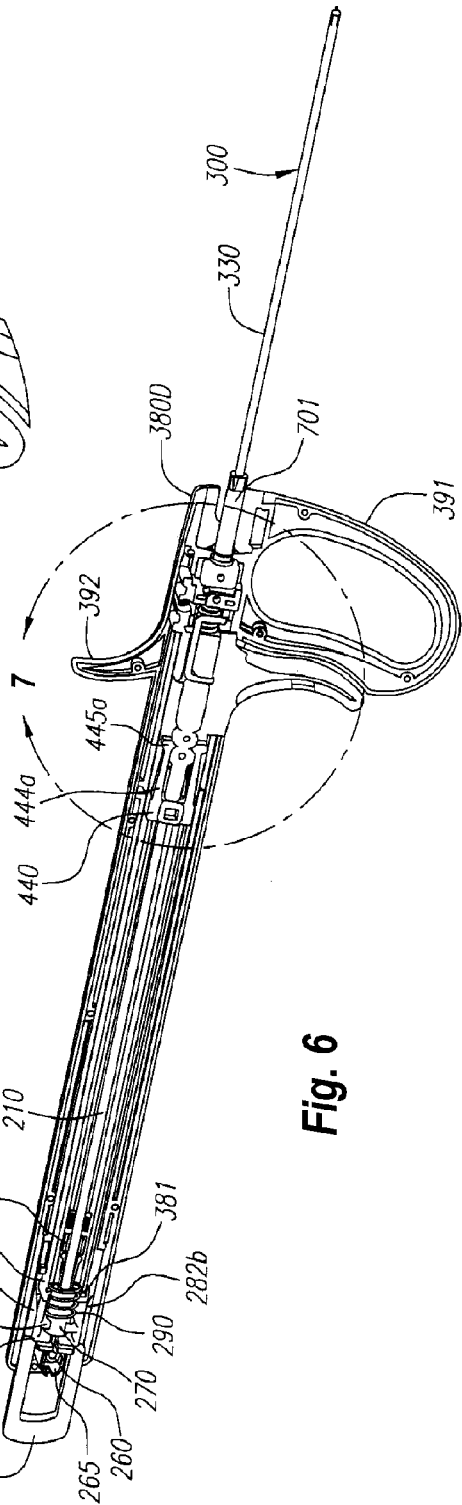
Fig. 7
Fig. 6

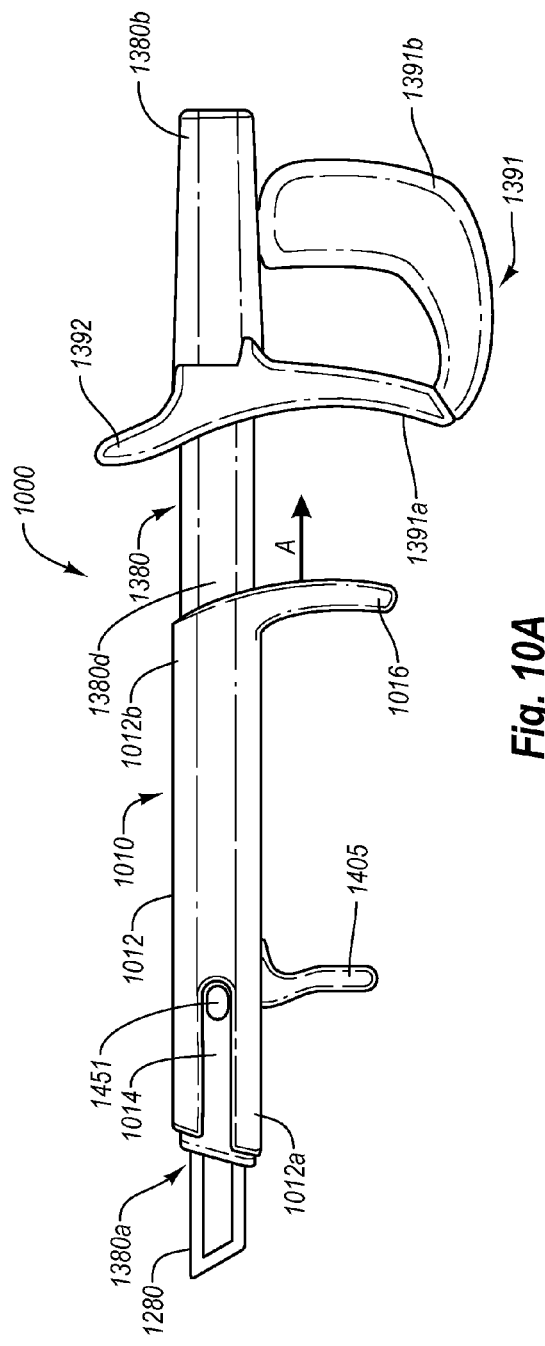
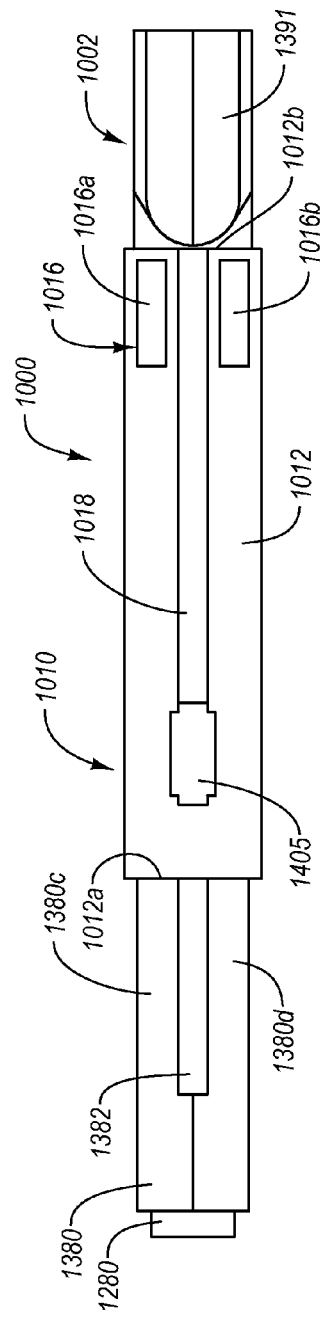
Fig. 10A
Fig. 10B

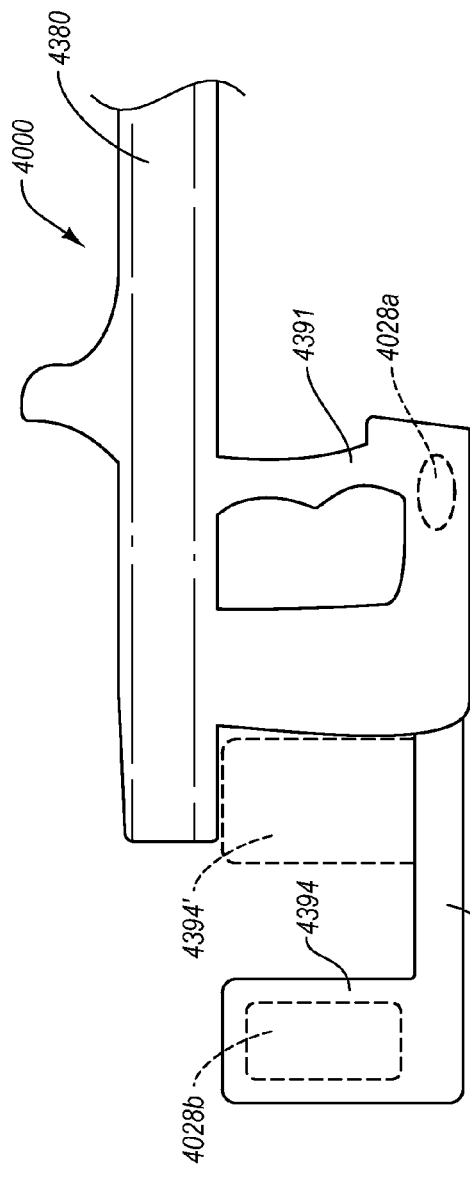
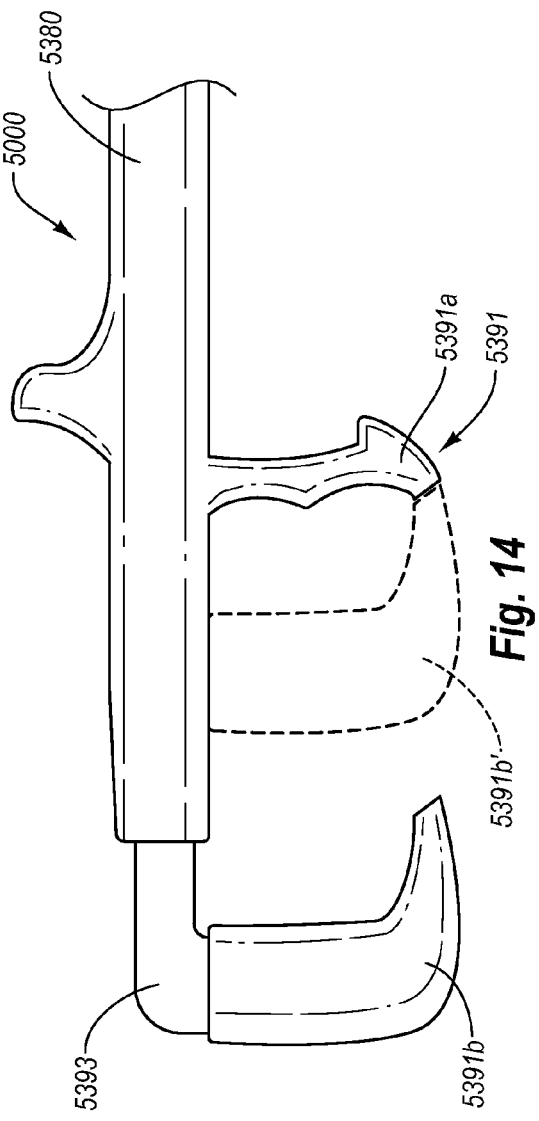

MODULAR CLIP APPLIER

BACKGROUND OF THE INVENTION

1. Field of the Invention

The present invention relates generally to apparatus and methods for closing and/or sealing openings through tissue, and more particularly to apparatus and methods for delivering a closure element for closing a puncture in a blood vessel or other body lumen formed during a diagnostic or therapeutic procedure.

2. The Relevant Technology

Catheterization and interventional procedures, such as angioplasty or stenting, generally are performed by inserting a hollow needle through a patient's skin and tissue into the vascular system. A guide wire may be advanced through the needle and into the patients blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath would be removed, leaving a puncture site in the vessel wall. Traditionally, external pressure would be applied to the puncture site until clotting and wound sealing occur, however, the patient must remain bedridden for a substantial period of time after clotting to ensure closure of the wound. This procedure, however, may be time consuming and expensive, requiring as much as an hour of a physicians or nurses time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

To facilitate positioning devices that are percutaneously inserted into a blood vessel, "bleed back" indicators have been suggested. For example, U.S. Pat. No. 5,676,689, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel.

Accordingly, apparatus and methods for delivering a device for closing a vascular puncture site or other opening through tissue would be useful.

BRIEF SUMMARY

The present invention is directed toward an apparatus and method for delivering a closure element through tissue and into an opening formed in, or adjacent to, a wall of a blood vessel or other body lumen of any size. The apparatus can be configured to receive and retain the closure element so that the closure element can be disposed substantially within the apparatus. The apparatus can also be configured to engage the blood vessel wall adjacent to the opening and to position the closure element substantially adjacent to an outer surface of the blood vessel wall adjacent to the opening.

When properly positioned, the apparatus can be activated to distally deploy the closure element. During deployment, the apparatus can be configured to substantially uniformly expand the closure element beyond a natural cross-section of the closure element such that the closure element, when deployed, can be configured to engage the blood vessel wall and/or tissue. Engaging the blood vessel wall and/or tissue, the closure element can be further configured to return to the natural cross-section. Thereby, the engaged blood vessel wall and/or tissue are drawn substantially closed and/or sealed, such that, for example, hemostasis within the opening can be enhanced.

The present invention can also accommodate various configurations of an apparatus for deploying a closure element. The apparatus can include, for example, any of a variety of different trigger mechanisms. For instance, an exemplary apparatus may include a locator assembly that extends into a puncture site. A carrier assembly may be coupled with the locator assembly and can retain the closure element. A triggering system coupled to the carrier assembly can advance the carrier assembly toward the distal end of the locator assembly, and can include a trigger element that deploys the closure element. A body or housing may receive the locator assembly, carrier assembly, and triggering system, and can include a trigger element integrally formed with, or separate from, the housing. For instance, the trigger element may be a trigger button formed in the housing. The button may include a flexible tab that is elevated with respect to, or substantially flush with, the exterior surface of the housing. An envelope may also be integral with the housing and the trigger button formed in the housing.

The present invention can also accommodate for variations in the size of the physicians hand and grip by selectively reducing the distance between the devices handle portion and a portion of a triggering system usable to deploy the closure element. The triggering system of the apparatus can at least partially move a trigger extension graspable by a physician or clinician as a locator assembly locates the blood vessel wall prior to deploying the closure element. This partial movement reduces the gap between the trigger extension and the handle portion. In this manner, a physician or clinician does not need to stretch uncomfortably to position a thumb or finger on the trigger extension, grasping the handle portion, and maintaining the device in the desired orientation relative to the tissue and/or the puncture site.

An apparatus of the present invention usable to deliver a closure element to an opening formed in a wall of a body lumen and accommodate for variations in size of a user's hands can include a housing and a locator assembly having a distal end region configured to extend into the opening and selectably contact the wall of the body lumen. A carrier assembly can be coupled with the locator assembly, the carrier assembly retaining the closure element. A triggering system can also cooperate with the locator assembly and advance towards the distal end region of the locator assembly. A throw reducing mechanism can be slideably disposed relative to the housing and linked to the triggering system, such that as the throw reducing mechanism slides relative to the housing, the triggering system also moves relative to the housing. Optionally, movement of the throw reducing mechanism engages a plunger. The throw reducing mechanism may also be modular and removable from the housing.

According to another aspect of the present invention, an apparatus usable for delivery a closure element accommodates different lengths of the arm and/or provides a stable base upon which the physician or clinician can move the device or apparatus as the closure element is positioned and deployed. In one configuration, the stable base is integral with, or selectively connectable to, a housing and can be extended as desired by the user. The stable base may be extendable and can lock in one or more positions as it moves from an unexpanded position to an expanded position. The stable base optionally forms a portion of a handle portion coupled with the housing. The expandable base fits comfortably within a user's hand while the hand is rested on a patient during the procedure to provide stability during use of the device and function as a base or pivot point for moving the remainder of the device or apparatus.

Other aspects and features of the present invention will become apparent from consideration of the following description in conjunction with the accompanying drawings.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

FIG. 2 illustrates the assembled carrier assembly and triggering assembly of the apparatus shown in FIGS. 1A and 1B;

FIG. 3A illustrates a close-up view of the proximal end of the apparatus shown in FIG. 2;

FIG. 3B illustrates a close-up view of the distal end of the apparatus shown in FIG. 2 in an unexpanded state;

FIG. 3C illustrates a close-up view of the distal end of the apparatus shown in FIG. 2 in an expanded state;

FIG. 4 illustrates the apparatus of FIG. 2 after distal advancement of the locator assembly, the triggering system and the carrier assembly;

FIG. 5 illustrates a close-up view of the triggering system and carrier assembly of the apparatus shown in FIG. 4;

FIG. 6 illustrates the apparatus of FIGS. 1A and 1B after the clip has been released to close the opening in the tissue;

FIG. 7 illustrates a close-up view of the triggering system and carrier assembly of the apparatus of FIGS. 1A-1B after the clip has been released to close the opening in the tissue;

FIGS. 10A-11 illustrate various exemplary embodiments of closure element delivery devices which partially advance a triggering system;

FIGS. 12-14 illustrate various embodiments of delivery devices having extendable stabilizers for handling the respective delivery devices;

Figure 1A:
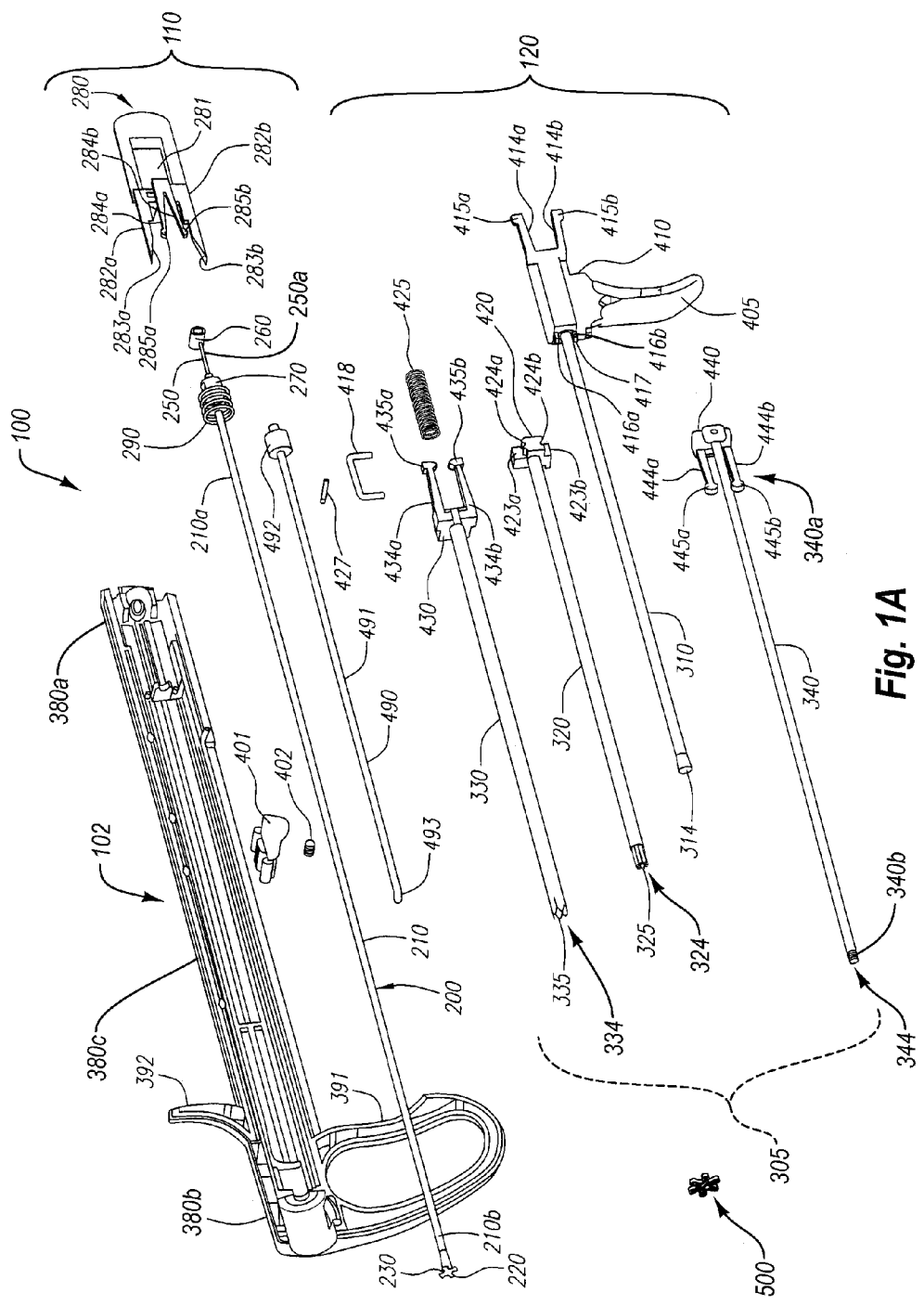
FIG. 1A illustrates an assembly view of the components of one embodiment according to the present invention for closing openings in blood vessel walls.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

The embodiments described herein extend to methods, systems, assemblies, and apparatus for closing and/or sealing openings in a blood vessel or other body lumen formed during a diagnostic or therapeutic procedure. The apparatuses of the present invention are configured to deliver a closure element through tissue and into an opening formed in and/or adjacent to a wall of a blood vessel or other body lumen.

Since conventional apparatuses for sealing openings formed in blood vessel walls can snag tissue adjacent to the openings during positioning and may not provide an adequate seal, an apparatus that is configured to prevent inadvertent tissue contact during positioning and to engage tissue adjacent to the opening can prove much more desirable and provide a basis for a wide range of medical applications, such as diagnostic and/or therapeutic procedures involving blood vessels or other body lumens of any size. Further, since conventional apparatuses for sealing openings formed in blood vessel walls are typically one-size and do not provide a mechanism to accommodate for variations in the size or configuration of the physician or clinicians hands, an apparatus that varies its operational configuration to accommodate for physician or clinician hand sizes can prove much more desirable and beneficial to the medical arts. These results, whether individually or collectively, can be achieved, according to one embodiment of the present invention, by employing an apparatus as shown in the figures and described in detail below.

As will be discussed in more detail below, the apparatuses of the present invention are configured to deliver a closure element through tissue and into an opening formed in and/or adjacent to a wall of a blood vessel or other body lumen. The apparatus can be configured to receive and retain a closure element such that the closure element can be disposed substantially within the apparatus. The apparatuses in accordance with the present invention generally include a housing having a proximal end and a distal end, and which receives a locator and clip delivery assembly extending from the distal end of the housing. A triggering system is also at least partially received by the housing and generally located at the proximal end of the housing. The housing may further include a handle portion at the distal end, and the triggering system may include a trigger extension extending from the housing, so as to facilitate use of the apparatus to deploy a closure element and thereby close an opening formed in and/or adjacent to a wall of a blood vessel or other body lumen.

Referring now to FIG. 1, an exploded assembly view of one closure apparatus is shown in accordance with the present invention. As shown in FIG. 1, the apparatus can include a housing that receives or retains a plurality of tubular members. The tubular members can be concentrically disposed within the housing of the device, with each tubular member having an associated block member fixedly attached to the proximal end thereof. The block members can be configured to interact with each other as well as with features of the housing, such as through movement of a triggering system. The interaction of the tubular members, the blocks, and the triggering system will be described in greater detail below. Also described below will be additional details regarding the handle portion of the housing and the manner by which the movement of the tubular members and the triggering system results in variation of the devices operational configuration to accommodate for physician or clinician hand sizes.

Figure 1B:
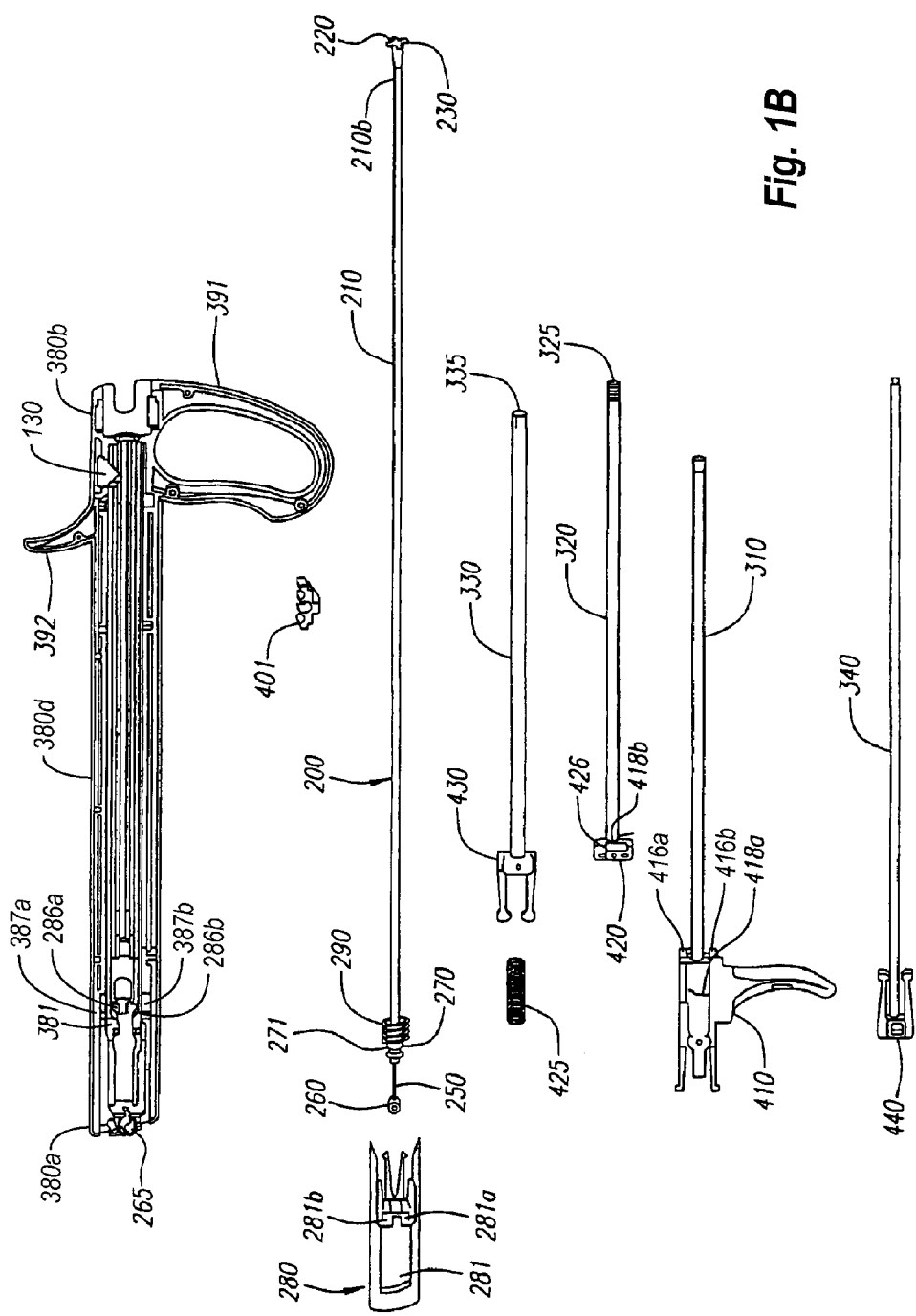
FIG. 1B illustrates another assembly view of the components of one embodiment according to the present invention for closing openings in blood vessel walls.

With continued reference to FIGS. 1A and 1B, apparatus 100 can be provided as one or more integrated components and/or discrete components that may be retained within a housing 102, having a housing top half 380c and a housing bottom half 380d. For example, apparatus 100 can include a locator assembly 110 and a carrier assembly 120. For purposes of illustration, locator assembly 110 and carrier assembly 120 are shown in FIG. 1A as comprising substantially separate assemblies. As desired, however, locator assembly 110 and carrier assembly 120 each can be provided, in whole or in part, as one or more integrated assemblies.

Turning to FIGS. 1A-2, 4, and 6, the assembly 110 can include a locator assembly 200. This locator assembly 200 can include flexible or semi-rigid tubular body 210 (such as an elongate rail) with a longitudinal axis. Tubular body 210 can have a proximal end region 210a and a distal end region 210b and can include a predetermined length and a predetermined outer cross-section, both of which can be of any suitable dimension. Distal end region 210b of locator assembly 200, as shown in more detail in FIGS. 3B and 3C, can include a substantially rounded, soft, and/or flexible distal end or tip 220 to facilitate advancement and/or retraction of distal end region 210b into a blood vessel or other opening in tissue. As desired, a pigtail (not shown) may be provided on tip 220 to further aid atraumatic advancement of distal end region 210b.

Distal end region 210b of locator assembly 200 is selectably controllable between an unexpanded state, as shown in FIG. 3B, and an expanded state, as shown in FIG. 3C. As shown in FIG. 3B, when an expansion end 230 is in an unexpanded state, substantially flexible members 232 are substantially axially aligned with locator assembly 200. Alternatively, when expansion end 230 is in an expanded state, substantially flexible members 232 are flexed outward.

Returning to FIG. 1B, a control member 250, such as a rod, wire, or other elongate member, may be moveably disposed within a lumen (not shown) formed by tubular body 210 and extending substantially between the proximal end region 210a and distal end region 210b. Control member 250 may have proximal end region 250a coupled with a control block 260, and a distal end region 250b coupled with distal end region 210b of locator assembly 200, expansion end 230, and/or the movable end regions of substantially flexible members 232. Control block 260 may be formed of a metal or rigid plastic in a tubular shape, and may be adapted to be retained in control block cavity 265 formed on the internal surface of housing bottom half 380d, to thereby maintain control block 260 in a substantially fixed position relative to the housing 380. By moving tubular body 210 axially relative to control member 250, the distal end region 210b, expansion end 230, and/or the substantially flexible members 232 (FIG. 3B), are selectively transitioned between the unexpanded and expanded states.

With reference to FIG. 3A, a tubular body block 270 having proximal groove 271 may be formed on proximal end 210a of tubular body 210. Tubular body block 270 may be formed of metal, rigid plastic, or other substantially rigid material and may be formed integrally with or attached securely to tubular body 210. Proximal groove 271 and the proximal end of tubular body block 270 may have a shape adapted to cooperate with a pair of tabs 279a, 279b formed on a locator assembly block 280, whereby tubular body block 270 may be maintained in a fixed axial relationship with the locator assembly block 280. In this way, tubular body block 270 and tubular body 210 (FIG. 1B) may advance distally by distal advancement of locator assembly block 280.

A locator assembly spring 290 may be located coaxially with and may substantially surround a portion of tubular body block 270. Locator assembly spring 290 may be located between and in contact with the distal side of two of tabs 279a, 279b formed on locator assembly block 280 and the proximal side of locator assembly spring stop 381 formed on the inner surface of housing bottom half 380d. The locator assembly spring 290 so located may provide a force biasing to locator assembly block 280 in the proximal direction relative to housing 380.

Locator assembly block 280 may be formed of metal, plastic, or other rigid material. A function of locator assembly block 280 may be to allow a user to apply a force causing distal movement of tubular body 210 (FIG. 1) relative to control member 250 causing locator assembly 200 (FIG. 2) to transition from the unexpanded state to the expanded state. Slot 281 may be formed in the proximal end of locator assembly block 280. Slot 281 may have a size sufficient to accommodate control block 260 and control block cavity 265, and to allow locator assembly block 280 to travel axially relative to housing 380. As shown in FIG. 1, the distal end of locator assembly block 280 may include a pair of distally extending legs 282a-b, with each of legs 282a-b having a ramp 283a-b on its inward facing surface. Finally, the locator assembly block 280 may have a pair of distally extending release tabs 284a-b, each of release tabs 284a-b having a detent 285a-b.

As shown in FIGS. 2-3A, locator assembly block 280 may be slidably received and retained within grooves formed in the proximal end of housing 380, with the proximal end of locator assembly block 280 extending from the proximal end of housing 380. Control block 260 and control block cavity 265 may be located in slot 281 formed in the proximal end of locator assembly block 280.

To release locator assembly 200, and enable it to slidably move within the grooves formed in the proximal end of the housing 380 and allow locator assembly 200 to transition from its expanded state to its unexpanded state, the apparatus 100 can include a locator release system 490 (FIG. 1A). Turning to FIG. 1A, locator release system 490 of the apparatus 100 may include locator release rod 491 having release tab spacer block 492 formed on its proximal end. Locator release rod 491 and release tab spacer block 492 may be received and retained in a groove formed on the interior surface of housing bottom half 380d. Release tab spacer block 492 may be integrally formed with or attached to the proximal end of locator release rod 491 and may be formed of metal, plastic, or other rigid material. Release tab spacer block 492 may have a shape and size adapted to fit between release tabs 284a-b formed on locator assembly block 280, thereby biasing release tabs 284a-b outward and causing outward facing detents 285a-b to engage retaining grooves 286a-b (FIG. 1B) formed on the interior of housing 380. As long as detents 285a-b are thus engaged with retaining grooves 286a-b in housing 380, locator assembly block 280 is held in an axial position against the spring force imparted in the proximal direction by locator assembly spring 290.

With continued reference to FIG. 1A, the distal end of locator release rod 491 may have an engagement member 493 that comprises an inward bend on the distal end of locator release rod 491. As described more fully below, engagement member 493 on locator release rod 491 may be positioned within the apparatus 100 such that when closure element 500 is delivered, engagement member 493 is engaged and caused to move axially in the distal direction, thereby disengaging release tab spacer block 492 from locator assembly block 280 and causing locator assembly 200 simultaneously to transition from an expanded state to an unexpanded state.

Returning to FIG. 1A, the carrier assembly 120 may be coupled with, and slidable relative to, locator assembly 200. Carrier assembly 120 may be configured to receive and retain closure element 500, which may be disposed substantially within carrier assembly 120. Carrier assembly 120 may be further configured to position closure element 500 substantially adjacent to an opening to be closed, and to deploy closure element 500. Upon being deployed, closure element 500 can maintain a reduced cross-section but may also temporarily and substantially uniformly expand beyond the natural cross-section of closure element 500. In either case, closure element 500, when deployed, can engage an amount of the blood vessel wall and/or tissue adjacent to the opening. Thereafter, closure element 500 may be configured to return to the natural cross-section, optionally substantially uniformly, such that the blood vessel wall and/or tissue are drawn substantially closed and/or sealed.

As shown in FIG. 1A, carrier assembly 120 may include a tube set 305 of at least one tubular member. For instance, the illustrated tube set can include carrier member 310, pusher member 320, cover member 330, and support member 340, also shown in FIG. 8. Carrier member 310, pusher member 320, cover member 330, and support member 340 may be provided as a plurality of nested, telescoping members with a common longitudinal axis. Carrier member 310 may be configured to receive and support closure element 500. While being disposed on carrier member 310, closure element 500 may be deformed from the natural, planar configuration to form a substantially tubular closure element 500", as shown in FIGS. 10A-10G, and as described herein.

Returning to FIG. 1A, carrier member 310 may include proximal end region 310a and distal end region 310b. Carrier member 310 may also define lumen 314, which may extend substantially between proximal end region 310a and distal end region 310b and configured to slidably receive at least a portion of tubular body 210 of locator assembly 200 and/or support member 340. Although the exterior cross-section of the carrier member 310 may be substantially uniform, the distal end region 310b of carrier member 310 may have a cross-section that increases distally, as illustrated in FIG. 1A, for substantially uniformly expanding substantially tubular closure element 500 (FIG. 9G) beyond natural cross-section 530 (FIG. 9A) of closure element 500" when substantially tubular closure element 500" is deployed. Alternatively, distal end region 310b may be formed with a uniform cross-section to deploy closure element 500 without cross-sectional expansion.

Pusher member 320 may have proximal end region 320a and distal end region 320b. Pusher member 320 may be coupled with, and slidable relative to, carrier member 310. Pusher member 320 may include a predetermined length and a predetermined cross-section, both of which can be of any suitable dimension and can be configured to slidably receive carrier member 310 such that distal end region 320b of pusher member 320 may be offset proximally from distal end region 310b of carrier member 310. As desired, the predetermined length of pusher member 320 may be substantially equal to a predetermined length of carrier member 310. A predetermined length of pusher member 320 may be less than a predetermined length of carrier member 310 such that carrier member 310 and pusher member 320 may at least partially define a space 360 (FIG. 8) distal to distal end region 320b of pusher member 320 and along the periphery of carrier member 310.

Pusher member 320 may be substantially tubular and can define a lumen 324 that may extend substantially between proximal end region 320a and distal end region 320b and configured to slidably receive at least a portion of the carrier member 310. The cross-section of pusher member 320 may be substantially uniform and distal end region 320b of pusher member 320 can comprise one or more longitudinal extensions 325, which may extend distally from pusher member 320 and along the periphery of carrier member 310. Longitudinal extensions 325 may be biased such that longitudinal extensions 325 extend generally in parallel with the common longitudinal axis of carrier assembly 120. Longitudinal extensions 325 may be sufficiently flexible to expand radially, and yet sufficiently rigid to inhibit buckling as distal end region 320b is directed distally along carrier member 310 and engages the distally-increasing cross-section of distal end region 310b of carrier member 310 to deploy closure element 500

Cover member 330 may be configured to retain closure element 500, in its generally tubular configuration, substantially within the carrier assembly 120 prior to deployment. Being coupled with, and slidable relative to, pusher member 320, cover member 330 has proximal end region 330a and distal end region 330b, a predetermined length and a predetermined cross-section, both of which can be of any suitable dimension. Cover member 330 may be formed as a substantially rigid, semi-rigid, or flexible tubular member with an inner periphery and an outer periphery, and may define a lumen 334. Lumen 334 may extends substantially between proximal and distal end regions 330a, 330b of cover member 330 and may be configured to slidably receive at least a portion of pusher member 320. When cover member 330 is properly positioned within carrier assembly 120, as schematically illustrated in FIG. 11A, distal end region 330b may be configured to extend over the space 360, thereby defining annular cavity 370 for receiving and retaining substantially tubular closure element 500".

Figure 8:
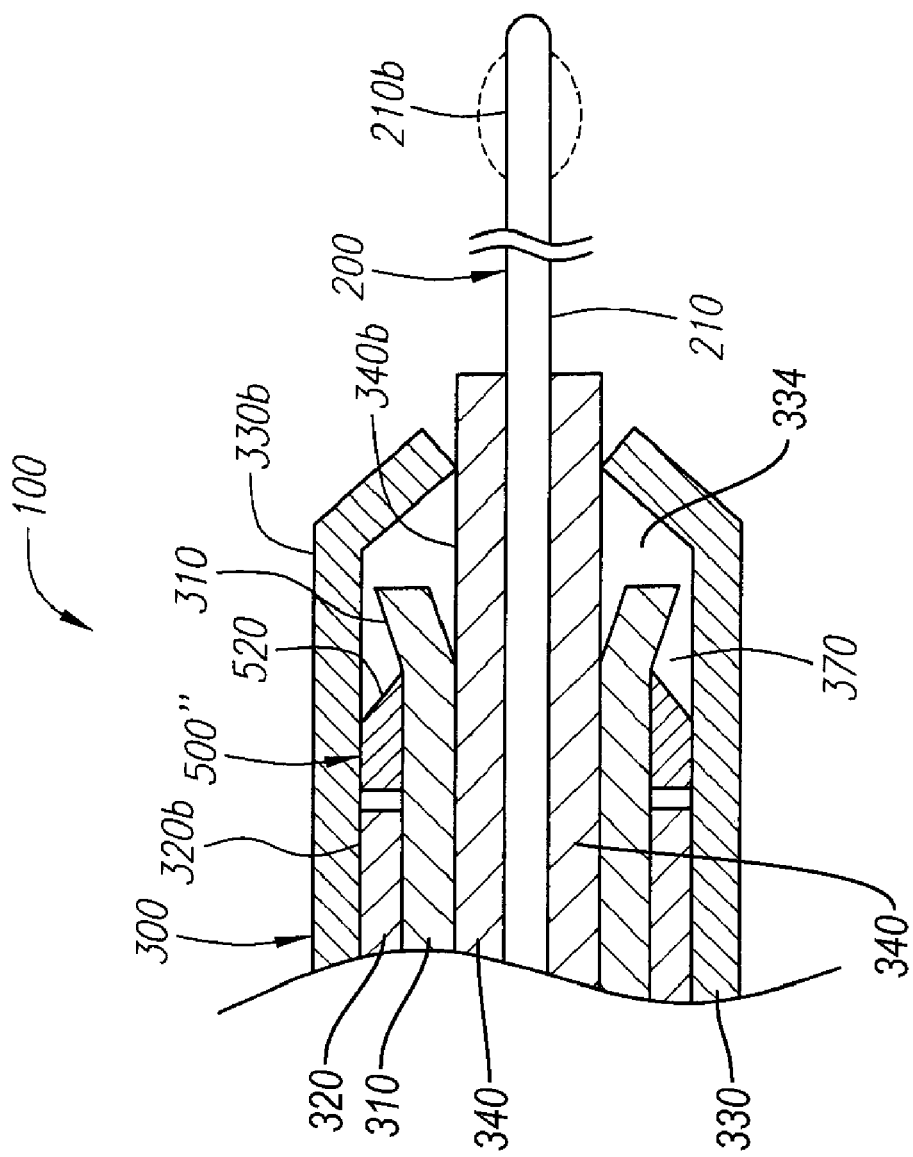
FIG. 8 illustrates a cross-sectional schematic view of the distal end of the apparatus shown in FIG. 4 as assembled for deployment.

The cross-section of cover member 330 may be substantially uniform, and distal end region 330b of cover member 330 may comprise one or more longitudinal extensions 335, which extend distally from cover member 330 and along an outer periphery of pusher member 320, as shown in FIG. 8. Although longitudinal extensions 335 can extend generally in parallel with the longitudinal axis of the tube set 305, longitudinal extensions 335 may be biased such that the plurality of longitudinal extensions 335 extend substantially radially inward. Thereby, longitudinal extensions 335 may at least partially close lumen 334 substantially adjacent to distal end region 330b of cover member 330.

With reference to FIGS. 1B and 15A, to permit closure element 500 to be deployed from annular cavity 370, longitudinal extensions 335 may be sufficiently flexible to expand radially to permit distal end region 310b of carrier member 310 to move distally past cover member 330 to open annular cavity 370 such that distal end region 330b no longer extends over the space 360.

When carrier assembly 120 is assembled as a plurality of nested, telescoping members, as shown in FIGS. 2 and 8, carrier member 310 is at least partially disposed within, and slidable relative to, a lumen of pusher member 320, and support member 340 is slidably relative to pusher member 310. Pusher member 320, in turn, is at least partially disposed within, and slidable relative to, lumen 334 of cover member 330. To couple carrier assembly 120 with locator assembly 200, tubular body 210 of locator assembly 200 may be at least partially disposed within, and slidable relative to, lumen 314. The longitudinal axis of locator assembly 200 may be substantially in axial alignment with the common longitudinal axis of carrier member 310, pusher member 320, and cover member 330.

The apparatus 100 may also include support member 340 as shown in FIG. 1A. Support member 340 may be configured to slidably receive tubular body 210 of locator assembly 200 and provide radial support for distal end region 210b of tubular body 210 when locator assembly 200 is coupled with the carrier assembly 120. Carrier assembly 120 can advantageously include support member 340, for example, if tubular body 210 is not sufficiently rigid or under other circumstances in which support for tubular body 210 might be desirable. It also will be appreciated that support member 340 may also be configured to inhibit longitudinal extensions 335, which extend from distal end region 330b of cover member 330, from expanding prematurely when closure element 500 is deployed. If longitudinal extensions 335 were to expand prematurely, they may become hung up on an introducer sheath or other delivery member (if an introducer sheath or delivery member is used), the tissue, or the wall of the blood vessel. This may interfere with the proper advancement or other movement of cover member 330 and carrier assembly 120.

Support member 340 may be formed as a substantially rigid, semi-rigid, or flexible tubular member, and may include proximal end region 340a and distal end region 340b. Having an outer periphery, support member 340 may define lumen 344, extending substantially between proximal end region 340a and distal end region 340b and configured to slidably receive and support at least a portion of tubular body 210 of locator assembly 200. Support member 340, in turn, can be at least partially slidably disposed within lumen 314 of carrier member 310 such that tubular body 210 of locator assembly 200 is coupled with, and slidable relative to, carrier member 310 in the manner described in more detail above.

Support member 340 may have a predetermined length and a predetermined cross-section, both of which can be of any suitable dimension, and may have a substantially uniform cross-section. Although shown and described as being substantially separate for purposes of illustration, it will be appreciated that carrier member 310, pusher member 320, cover member 330, and/or support member 340 may be provided, in whole or in part, as one or more integrated assemblies.

With reference to FIG. 8, support member 340 may also include a distal end that is blunt, rounded and/or includes a radius or curved portion that may prevent and/or eliminate damage to tubular body 200 as tubular body is moved with respect to support member 340. In some cases during deployment, as discussed in more detail below, tubular body 200 may be inserted into a lumen of an introducer at such an angle as to require tubular body 200 to flex with respect to tube set 305 as much as between about 0 degrees and 90 degrees, preferably between about 10 degrees and 90 degrees and more preferably between 30 degrees and 60 degrees, for example when used in conjunction with a femoral artery. The above-described distal end of the distal end region 340b prevents and/or eliminates damage to tubular body 200 that may result from a sharp edge pressed along tubular body 200 during advancement of tube set 305, and more particularly, support member 340 and the distal end of the distal end region 340b.

Illustratively, the radii of the distal end of the support member 340 can have various sizes and configurations. In one configuration, the distal end radii can be about 0.002 inches. In still another configuration, the distal end radii can be about 0.004 inches. In still another configuration, the distal end radii can be about 0.002 inches or greater. Increasing the radii of the distal end of support member 340 to about 0.004 inches, for instance, can decrease the amount of force required to overcome a bend in locator assembly 200 over those devices having a distal end radii of about 0.002 inches. This is because a gap formed between the interior diameter of support member 340 and the locator assembly 200 is larger for the 0.004 inch radii than for the 0.002 inch radii.

In addition to the above, with the distal end having a radii greater than 0.002 inches, such as but not limited to 0.004 inches, there is a decrease in the possibility that the support member 340 cuts or otherwise damages the locator assembly 200 during positioning of the distal end of the apparatus 100 and subsequent deployment of the closure element 500. Further, a radii greater than 0.002 inches, such as but not limited to 0.004 inches, may not increase the forces used to split an introducer sheath and may not elongate the introducer sheath during positioning and deploying of the closure element 500.

With reference to FIGS. 1A and 1B, carrier assembly 120 may also include a portion of housing 380. For instance, the carrier assembly 120 can optionally include the top half 380c of housing 380, illustrated in FIG. 1A, and the bottom half 380d is shown in FIG. 1B. It will be understood, however, that housing 380 may be separate from the carrier assembly 120, while retaining and/or receiving all or a portion of the carrier assembly 120.

Housing 380 may be formed as an elongate member with a longitudinal axis, a periphery and may include proximal end region 380a and distal end region 380b. Thereby, when apparatus 100 is assembled, tubular body 210 of locator assembly 200 may be at least partially disposed within, and slidable relative to, tube set 305 such that distal end region 210b of tubular body 210 extends beyond distal end regions 310b, 320b, 330b, and/or 340b. Tubular body 210, carrier member 310, pusher member 320, cover member 330, and, if provided, support member 340 may be at least partially disposed within, and slidable relative to, housing 380. Proximal end region 210a of tubular body 210 and proximal end regions 310a, 320a, 330a, and/or 340a of tube set 305 can be at least partially disposed within, and slidable relative to, housing 380. Distal end regions 210b, 310b, 320b, 330b, and 340b may extend from distal end region 380b of housing 380 such that common longitudinal axis 350 of tube set 305 may be substantially axially aligned with longitudinal axis 386 of housing 380. When configured to slidably retain respective proximal end regions 210a, 310a, 320a, 330a, and 340a, housing 380 supports tube set 305 and can have one or more handles 391, 392 to facilitate use of apparatus 100. Handles 391, 392 may extend, optionally substantially radially, from the outer periphery of housing 380 and can be provided as illustrated or in any manner known in the art.

To facilitate deployment of the closure element 500, the apparatus 100 can include a triggering system 400, shown in FIG. 2, which cooperates with a portion the locator assembly 200. For instance, a portion of locator assembly 200 and a portion of triggering system 400 may cooperate and be accessible externally to housing 380, as shown in FIGS. 1A and 1B. As shown in FIGS. 1A, 1B, 4-7, triggering system 400 of apparatus 100 may be disposed substantially within housing 380. Triggering system 400 may be configured to control the relative axial movement and/or positioning of distal end regions 310b, 320b, 330b, and 340b and/or locator assembly distal end region 210b. Axial motion of one or more of carrier member 310, pusher member 320, cover member 330, and support member 340 and/or tubular body 210 may be attained, for example, by applying an axial force to triggering extension 405.

Triggering system 400 may include a set of block members including carrier block 410, pusher block 420, cover block 430, and support block 440, each of which may be formed integrally with or securely attached to its respective member of carrier assembly 120. The block members may be adapted to selectably couple and decouple carrier member 310, pusher member 320, cover member 330, and support member 340 relative to one another in order to provide axial movement of those components in a predetermined manner intended to deliver closure element 500 in the manner described herein. For example, when carrier assembly 120 reaches a first predetermined distal position, support member 340 may be decoupled from carrier member 310, pusher member 320, and cover member 330, and may be thereafter substantially inhibited from further axial movement. Thereby, carrier member 310, pusher member 320, and cover member 330 may be directed distally as support member 340 remains substantially stationary. Subsequently, carrier member 310 and cover member 330 can be decoupled from pusher member 320 and thereby inhibited from further axial movement. Pusher member 320 may be directed distally as support member 340, carrier member 310, and cover member 330 remain substantially stationary, as described more fully herein.

Carrier block 410 may be disposed on proximal end region 310a of carrier member 310 and may include trigger extension 405, which extends through a slot in housing 380 to the exterior of housing 380, accessible by a user. This carrier block 410, as shown in FIG. 3A, may include a pair of grooves 413a-b formed on a peripheral surface of carrier block 410. Grooves 413a-b may be adapted to receive and retain a pair of tabs 445a-b formed on a pair of legs 444a-b extending distally from support block 440, thereby selectably coupling support block 440 to carrier block 410. Carrier block 410, as illustrated in FIG. 1A, may also include a pair of distal tabs 416a-b extending from the distal end of carrier block 410, and adapted to engage a pair of slots 423a-b formed on the proximal end of pusher block 420.

As shown in FIGS. 1A and 3A, carrier block 410 may also include a pair of arms 414a-b extending in the proximal direction from the proximal end of carrier block 410, each of arm 414a-b having an outward directed tab 415a-b at its proximal end. Tabs 415a-b may be adapted to selectably engage a pair of slots 387a-b (FIG. 1B) formed on the interior surface of housing 380 near its proximal end and, when so engaged, to fix the axial position of carrier block 410 and, with it, carrier assembly 120 relative to housing 380. Tabs 415a-b may be disengaged from slots 387a-b FIG. 1B) in housing 380 when locator assembly block 280 is moved axially in the distal direction in the following manner. As locator assembly block 280 is advanced distally, the interior surfaces of the ramps 283a-b on locator assembly block legs 282a-b engage the exterior surfaces of tabs 415a-b and cause carrier block arms 414a-b to flex inward, releasing tabs 415a-b from the slots 387a-b in the housing, thereby freeing carrier block 410 and carrier assembly 120 to move axially. Thus, axial movement of carrier block 410 within apparatus 100 is inhibited until locator assembly block 280 is advanced to transition locator assembly 200 to the expanded condition, simultaneously releasing tabs 415a-b on carrier block 410.

Pusher block 420 may be disposed on proximal end region 320a of pusher member 320. As described above, pusher block 420 may include a pair of slots 423a-b formed on its proximal end, and adapted to selectably engage distal tabs 416a-b extending from the distal end of carrier block 410. Pusher block 420 may also include a pair of grooves 424a-b formed on its peripheral surface, the grooves 424a-b being adapted to engage a pair of tabs 435a-b formed on a pair of forks 434a-b extending from the proximal side of cover block 430 to selectably couple cover block 430 to pusher block 420.

Cover block 430 may be disposed on proximal end region 330a of cover member 330. As described above, cover block 430 may include a pair of forks 434a-b extending from the proximal end of the cover block 430, each of forks 434a-b having an inward directed tab 435a-b adapted to engage grooves 424a-b on the peripheral surface of pusher block 420 to selectably couple cover block 430 to pusher block 420.

Support block 440 may be disposed on proximal end region 340a of support member 340. As described above, support block 440 may include a pair of legs 444a-b extending from the distal end of the support block 440, each of legs 444a-b having an inward directed tab 445a-b adapted to engage grooves 413a-b formed on the surface of carrier block 410 to selectably couple support block 440 to carrier block 410.

Carrier block 410, pusher block 420, cover block 430, and support block 440 are shown in FIGS. 2, 3A, 4, and 5 in their fully coupled state, with support block 440 coupled to carrier block 410, pusher block 420 coupled to carrier block 410, and cover block 430 coupled to pusher block 420. In this arrangement, carrier assembly 120 comprises a coaxial set of tubes as shown in FIG. 8, with support member 340 slidably retained substantially within carrier member 310, which is in turn slidably retained substantially within pusher member 320, which is in turn slidably retained substantially within cover member 330.

Triggering system 400 of apparatus 100 may include an energy storing element that is used in the final stage of closure element 500 delivery processes. The energy storing element, such as, but not limited to, a spring, such as pusher spring 425 shown in FIGS. 1A, 1B, 6 and 7, may be substantially retained in a spring cavity 417 formed in carrier block 410 and coaxially surrounds a proximal end region 310a of carrier member 310. Pusher spring 425 is capable of expanding and contracting, storing potential energy as it is contracted and releasing energy as it expands. In its fully expanded state, the pusher spring 425 has a length that is greater than the length of spring cavity 417. The cross-sectional dimension of pusher spring 425 may be such that it backs up against and contacts the proximal end of pusher block 420. Thus, when pusher spring 425 is in place between carrier block 410 and pusher block 420, pusher spring 425 is capable of imparting a force biasing carrier block 410 away from pusher block 420.

Prior to delivery of closure element 500, the distal end of carrier block 410 is in physical contact with the proximal end of pusher block 420. In this pre-delivery condition, pusher spring 425 is in a contracted state and is maintained fully within spring cavity 417. A catch member 418 serves the function of maintaining the carrier block 410 and pusher block 420 in the pre-delivery condition against the spring force of pusher spring 425, the force of which would otherwise force apart carrier block 410 from pusher block 420. Catch member 418 may be a U-shaped piece of metal, plastic, or other rigid material that engages first groove 419a formed on the surface of carrier block 410 and second groove 419b formed on the surface of pusher block 420. With reference to FIGS. 1A and 1B, pusher block 420 includes hole 426 extending through a portion thereof, with one end of hole 426 opening into groove 419b. Hole 426 is adapted to receive trip pin 427. During the closure element deployment process, trip pin 427 is advanced through hole 426, where it encounters catch member 418 retained in the groove 419b. Further advancement of trip pin 427 causes catch member 418 to become disengaged from groove 419b, thereby releasing the force of pusher spring 425.

The operation of the triggering system 400 of the apparatus 100 is illustrated in FIGS. 2-9 with the closure element 500 disposed substantially within the apparatus 100. As shown in FIGS. 2-3B, apparatus 100 has an initial position in which locator assembly block 280 is extended proximally and triggering system 400 is in its most proximal position. Accordingly, the locator assembly 200 is in its unexpanded state, as shown in FIG. 3B. At a point in time that the distal end region 210b of the locator assembly 200 has been positioned as desired (for example, within the blood vessel), locator assembly block 280 is depressed distally, as shown in FIG. 4, thereby transitioning locator assembly 200 to the expanded state, as shown in FIG. 3C, and, simultaneously, releasing triggering system 400 from the initial position (in the manner described above) such that triggering system 400 can be advanced distally within the housing 380.

Triggering system 400 can then be advanced distally within housing 380, thereby advancing tube set 305 into position adjacent the blood vessel. At a first predetermined position, shown in FIGS. 4 and 5, support block 440 encounters a support stop (not shown) on the interior surface of housing bottom half 380d that inhibits support block 440 from advancing further distally. As a result, an application of additional distal force to triggering system 400 causes support block 440 to decouple from carrier block 410. More specifically, tabs 445a-b on legs 444a-b of support block 440 disengage from grooves 413a-b on carrier block 410. Thus, support block 440 remains in the position shown in FIGS. 4 and 5, while carrier block 410 is able to advance further distally upon application of force to triggering system 400.

Turning to FIGS. 6-8, as the triggering system 400 is advanced further distally; cover block 430 engages a cover stop on the interior surface near the distal end region 380b of housing 380, thereby inhibiting additional distal advancement of cover block 430. In addition, trigger extension 405 engages handle 391 of the apparatus, thereby inhibiting additional distal advancement of carrier block 410.

Closure element 500 is next deployed by releasing pusher spring 425, which causes pusher block 420 (and, thus, pusher member 320 (FIG. 1A)) to advance distally, deploying closure element 500 in the manner described above. As previously described, pusher spring 425 is released by disengaging catch member 418 from groove 419b on pusher block 420, thereby releasing pusher spring 425 to force pusher block 420 and, thus, pusher member 320 distally relative to carrier block 410. This action causes pusher member 320 to deploy closure element 500 from within tube set 305. The catch member 418 is disengaged from groove 419b by applying a force to a trigger 401, which, in the deployment position, is aligned with trip pin 427 retained in pusher block 420. A trigger spring 402 biases trigger 401 outward relative to housing 380, with a portion of the trigger 401 extending through a hole 130 (FIG. 1B) in housing 380. A user applies an inward directed force to trigger 401 to counteract the biasing force of trigger spring 402 and force trigger 401 against the trip pin 427.

Trigger 401 may have any suitable shape corresponding to the shape of hole 130, such that it can be inserted therein for assembly of 100. Trigger 401 can be made of any suitable material, and may include a metal, plastic, or other rigid or semi-rigid material which may be inserted into hole 130 and used to counteract the biasing force of trigger spring 402 and to force trip pin 427 to release the energy stored in pusher spring 425 (FIG. 7). In the example embodiment illustrated in FIG. 1B, trigger 401 includes a trigger button formed separately from housing halves 380c, d. It will be appreciated, however, that this embodiment is exemplary only and that trigger button may have any other suitable configuration or construction.

Figure 9A:
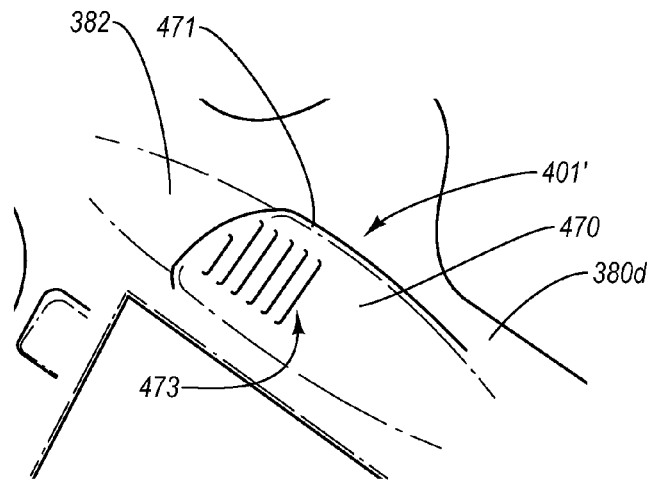
FIGS. 9A-9C illustrate a close-up view of exemplary trigger elements usable with the triggering system of the apparatus of FIGS. 1-7 to cause deployment of a closure element.
Figure 9B:
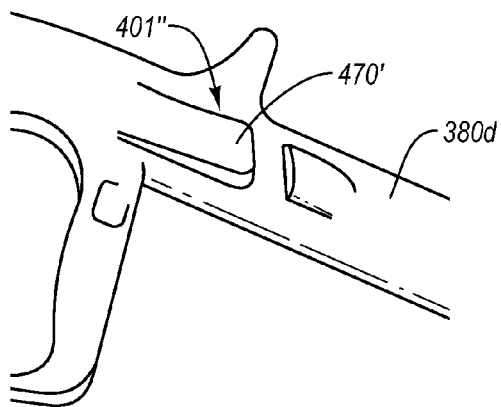
Figure 9C:
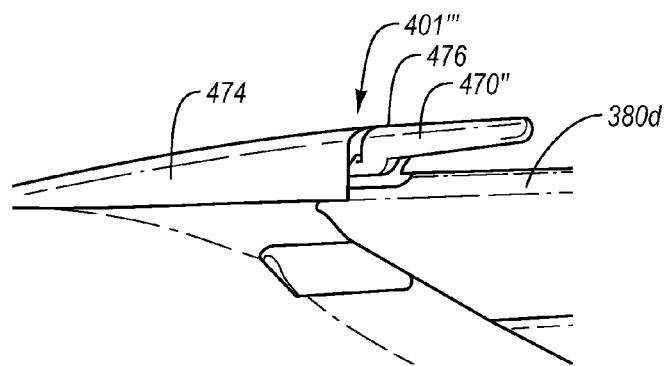

As illustrated in FIGS. 9A-9C, for example, a trigger may be formed at least partially as an integral component with housing bottom half 380d. For example, FIG. 9A illustrates an exemplary trigger 401' which includes a flexible trigger button 470 adapted to be depressed by a user to release a triggering mechanism and deploy a closure device as described herein. For example, similar to the manner described herein with respect to FIGS. 1A and 7, by applying a force to flexible button 470 sufficient to overcome the biasing force of trigger spring 402 (FIG. 7), flexible button 470 may be pressed against the trip pin 427 (FIG. 7), thereby causing trip pin 427 to disengage catch member 418 (FIG. 7). When catch member 418 is disengaged, this, in turn, allows pusher spring 425 (FIG. 1A) to expand, thereby causing pusher member 320 (FIG. 1A) to deploy closure element 500 (FIG. 1A) from within tube set 305.

As will be appreciated in view of the disclosure herein, flexible trigger button 470 can be formed in any of a variety of shapes and configurations. For instance, FIG. 9A illustrates an elongate trigger button 470 which is integrally formed in housing bottom half 380d. To allow trigger button 470 to flex, a slit 471 is formed around distal end of trigger button 470, and terminates at interface 472 at the proximal end of trigger button 470. In this embodiment, slit 471 surrounds approximately 70-80% of the perimeter of trigger button 470, although slit 470 may be of any size suitable to allow the distal end of trigger button 470 to be depressed sufficiently to counteract the biasing force of trigger spring 402. Indeed, in some embodiments, slit 471 may be eliminated entirely, such as where trigger button 471 is formed of a material having material properties allowing trigger button 470 to flex sufficiently inward when pressed. In other embodiments, slit 471 may be replaced with a groove which does not extend fully through the material forming housing bottom half 380d, but which enhances the flexibility of trigger button 470.

As will be appreciated in view of the disclosure herein, trigger 401' may further be adapted to facilitate use by a clinician or physician. For example, in the illustrated embodiment, trigger 401' optionally includes a gripping portion 473 on the flexible portion of trigger button 470, thereby allowing a user to find and depress trigger 401' with little effort, and with little risk that the clinician or physician's finger will inadvertently slip from trigger 401'. Gripping portion 473 may include, for example, a depression in which a finger can be positioned. Additionally, or alternatively, gripping portion 473 can include one or more ridges, bumps, depressions, or other contours or elements which allow a user to more effectively grip the trigger button. Optionally, gripping portion 473 or trigger button 470 may provide a visual indicator to the user of the location to press on housing bottom half 380*d* so as to deploy closure element 500 (FIG. 1A). For instance, trigger button 470 may have a different color relative to housing bottom half 380*d*. Additionally, or alternatively, gripping portion 473 may provide contours sufficient to easily determine the location of trigger button 470.

Trigger button 470, as described above, is but one example embodiment of a suitable trigger button, and trigger button 470 may any number of other suitable configurations. For example, trigger button 470 have any of a variety of shapes and may be, for example, generally circular. Similarly, while trigger button 470 is configured such that its distal end may be depressed to deploy a closure element, trigger button 470 may alternatively be configured such that its proximal end can be depressed to deploy closure element 500 (FIG. 1A).

As also illustrated in FIG. 9A, housing bottom half 380*d* can include a surface 382 in which trigger button 470 is formed. In the illustrated embodiment, trigger button 470 is substantially in-line with surface 382, such that it is only marginally elevated or depressed relative to surface 382. Surface 382 may be substantially planar or may have a rounded configuration, or may be elevated or depressed relative to the principal surface of housing bottom half 380*d*. In some cases, such as where trigger button 470 is generally in-line with surface 382, trigger button 470 may also have a generally planar or rounded configuration which generally corresponds to the shape and configuration of surface 382.

As illustrated in FIG. 9B, it will be seen that it is not necessary that an integral trigger button be formed in-line with a planar surface of housing bottom half 380*d*. For instance, in the illustrated embodiment, a trigger 401" includes a trigger button 470' that is integral with housing bottom half 380*d*, but is elevated therefrom. Similar to trigger button 470 of FIG. 9A, trigger button 470' may also be flexible so as to allow a user to press trigger button 470', thereby causing deployment of closure element 500 (FIG. 1A).

Now turning to FIG. 9C, still another example embodiment of a trigger 401''' is illustrated. Trigger 401''' operates in a manner similar to that of trigger 401, 401' and/or 401" in that when pressed by a user, it can cause deployment of a closure element. In the illustrated embodiment, trigger 401''' includes a trigger button 470" and an envelope 474. In particular, in this embodiment, envelope 474 is elevated relative to the outer surface of housing bottom half 380*c* and includes an opening 475 therein. Trigger button 470" can include an interior portion (not shown) contained within envelope 474, and which is coupled with trigger spring 402 (FIG. 7). Additionally trigger button 470" can include an exterior portion 476 which can be manipulated by a user. In one embodiment, trigger button 470" can be cantilevered within envelope 474 such that when exterior portion 476 of trigger button 470" is pressed, the interior portion of trigger button 470''' counteracts the biasing force of trigger spring 402 to cause deployment of closure element 500 in the manner described above.

Referring now to FIGS. 1A and 6, in addition to deploying closure element 500, the distal advancement of pusher block 420 also causes locator release system 490 to activate, thereby transitioning locator assembly 200 from the expanded state to the unexpanded state. As pusher block 420 advances distally to deploy closure element 500 in the manner described above, pusher block 420 also engages engagement member 493 of locator release system 490 and advances locator release rod 491 distally. This action causes release tab spacer block 492 to disengage from release tabs 284*a-b* on locator assembly block 280 (see FIG. 1A), thereby releasing locator assembly block 280, which returns to its proximal position, causing locator assembly 200 to return to the unexpanded state. An indicator window (not shown) may be formed in housing 380 to give a visual indication that tab spacer block 492 has disengaged and that locator assembly 200 has returned to the unexpanded state. The deployment of closure element 500 and locator release actions occur nearly simultaneously.

Figure 11:
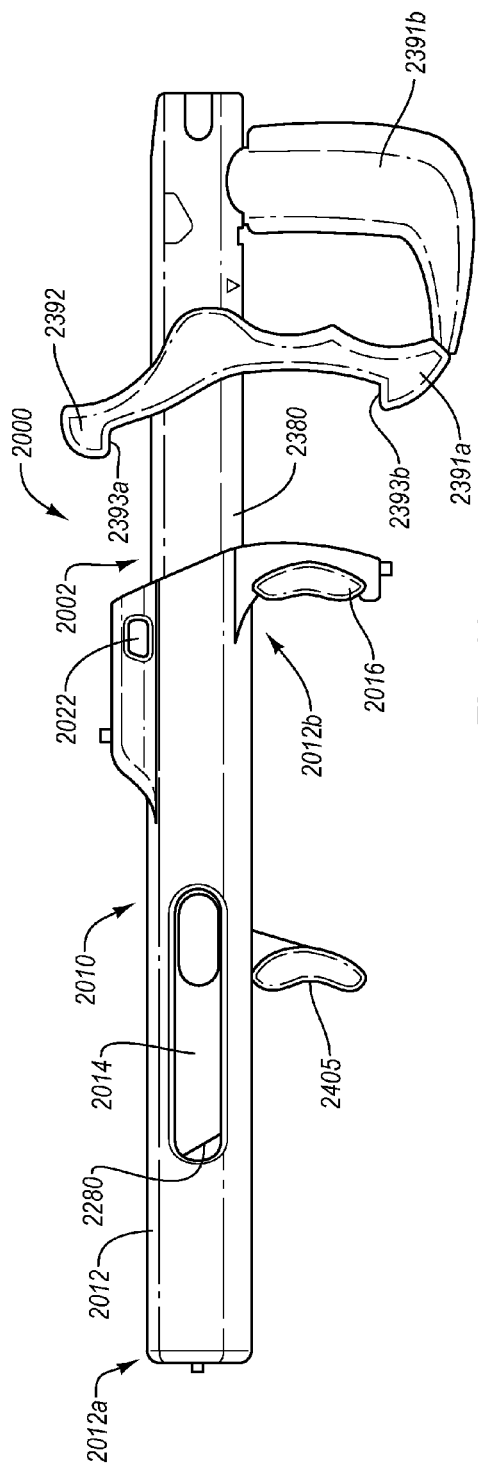

Generally, apparatus 1000 and 2000 illustrated in FIGS. 10A-11 can accommodate for variations in the size of the physician's hand and grip by selectively reducing the distance between the device's handle portion and a portion of the triggering system usable to deploy the closure element and/or move a carrier assembly. Advancement of a slider can at least partially advance a portion of the triggering system of the apparatus, including a trigger extension graspable by a physician or clinician. The partial movement reduces the gap or throw between the trigger extension and one or more handle portions. In this manner, a physician or clinician does not need to stretch uncomfortably to position a thumb or a finger on the trigger extension while grasping the handle portion and maintaining the device in the desired orientation relative to the tissue and/or puncture site of the patient. In this manner, a physician or clinician does not need to stretch uncomfortably to position a thumb or other finger on the trigger extension while grasping the handle portion and maintaining the apparatus in a desired position relative to the patient, tissue and/or puncture site.

In addition, the apparatus 1000 can include handle, hand grip, or finger portion disposed on the distal end of housing 1380 configured to be engaged by a user when advancing housing 1380 to deploy closure element 500 (FIG. 1A). This handle or handle portion or hand grip portion can include a shaped grasping portion 1391*a* and an elongate grasping portion 1391*b* spaced apart from the shaped grasping portion 1391*a*. Each of the portions 1391*a* and 1391*b* may be contoured to be received by a user's hand and/or fit against a user's fingers. For instance, the grasping portion 1391*a* can provide a stable base upon which the physician or clinician can move apparatus 1000 as the closure element is positioned and deployed. This grasping portion 1391*a* can include a curved profile that can receive a thumb and/or one or more fingers of the physician as the physician holds apparatus 1000. The curved profile allows the physician to grasp the handle or handle grip portion while resting his or her hand, wrist or forearm upon a patient during the procedure—including a procedure for deploying the closure element—thereby providing stability during use of the device.

It will be understood that although reference is made to one particular configuration of the handle, hand grip, or finger portions, one skilled in the art will appreciate and can identify various other configurations of handle portion that can perform the function of providing a stable base for manipulation of the apparatus 1000. For instance, and not by way of limitation, the handle portion can be planar rather than curved. Further, the handle portion can include one or more finger receiving holes. In addition, the handle may be comprised of a single component or, as illustrated in FIG. 10A, may include discrete handle components 1391*a* to be gripped by one hand of a physician, and a separate handle component 1391*b* to be gripped by, or pressed against, the physician's other hand. Furthermore, the handle components need not be integrally formed with housing 1380. Indeed, in other embodiments, handle 1391 is a discrete component which is selectively removable from housing 1380. In this manner, apparatus 1000 has a modular configuration in which a physician can select between any of a variety of different handle portions so as to customize the handle for his or her needs or comfort. In some embodiments, the entire handle portion is selectively removable, while in other embodiments less than all of the handle is selectively removable. For instance, stabilizing portion 1391b may be removable while handle portion 1391a is integral with or otherwise substantially permanently fixed to housing 1380.

With continued reference to FIGS. 10A and 10B, apparatus 1000 can be provided with one or more additional integrated and/or discrete components. For instance, and not by way of limitation, apparatus 1000 may include a throw reducer 1010 which is coupled with housing 1380 of apparatus 1000, and which is configured to reduce the gap between trigger extension 1405 and handle portion 1391 of apparatus 1000, thereby increasing the comfort to the physician using apparatus 1000. In this embodiment, throw reducer 1010 includes a sleeve 1012 which is mounted around the exterior surface of housing 1380 and configured to slide relative to housing 1380, although any other suitable throw reducing component, system or assembly may be used.

In particular, in the embodiment illustrated in FIGS. 10A and 10B, a slider 1012, which may be a sleeve fitted around the proximal portion 1380a of housing 1380 and/or around trigger extension 1405 of the triggering system, may further be configured to slide relative to housing 1380 in a manner that also causes the triggering system to at least partially advance within housing 1380.

For instance, FIG. 10B illustrates an alternative view of apparatus 1000 and sleeve 1012 in which the underside of slider 1012 is exposed. As shown in FIG. 10B, slider 1012 can include a slot 1018 on its underside. Slot 1018 may be fitted around and thereby receive trigger extension 1405. According to one embodiment, slot 1018 extends longitudinally along slider 1012, but only partially along the length of slider 1012. In the illustrated embodiment, slot 1018 has a length less than the total length of slider 1012, and does not fully extend to proximal end 1012a of slider 1012.

In the illustrated embodiment, inasmuch as slot 1018 does not extend fully through slider 1012, when slider 1012 is moved relative to housing 1380, slider 1012 can also engage trigger extension 1405, and thereby cause trigger extension 1405 to move in a corresponding direction. For instance, trigger extension 1405 may be located at a proximal-most position within housing 1380 and slider 1012 can be positioned at proximal portion 1380a of housing 1380. When slider 1012 initially engages trigger extension 1405, trigger extension 1405 can also be positioned at a proximal-most position within slot 1018. Slider 1012 may then be advanced distally relative to housing 1380 by using, for example, a finger extension 1016, which can be permanently or selectively attached to slider 1012.

As slider 1012 is advanced distally in direction the direction of arrow A, and from the proximal position illustrated in FIG. 10A to the distal position illustrated in FIG. 10B, trigger extension 1405 is continually engaged against slider 1012 at the proximal end of slot 1018, and slider 1012 can thereby cause trigger extension 1405 to move at least a portion of the length of housing 1380, while also remaining a constant distance from finger extension 1016. Thus, the axial and distally-directed movement of slider 1012 can also move trigger extension 1014 in a corresponding direction. When slider 1012 is advanced to its distal-most position, as shown in FIG. 10B, the gap or throw between trigger extension 1405 and grasping portion 1391 has thus been reduced for the physician or clinician using apparatus 1000. Thus, when the physician or clinician then desires to further advance trigger extension 1405 so as to prepare apparatus 1000 to deploy a closure element in the manner disclosed herein, the extent to which the physician or clinician must extend his or her hand to grip trigger extension 1405 has been reduced, thereby also improving the comfort to the physician or clinician. The two-stage movement of trigger extension 1405 can thus allow the user to more comfortably grasp and use trigger extension 1405, such that throw reducer 1010 may thus increase the ease and comfort involved in using apparatus 1000. Throw reducer 1010 can further allow for a greater variation in user strength as well as a greater variation in the physical size of a user's hand to fit better with apparatus 1000, as illustrated.

Once slider 1012 has partially moved trigger extension 1405, a carrier assembly can be further advanced by exerting a force on trigger extension 1405 to continue to move trigger extension distally in the manner described with reference to other embodiments above. After the locator has been deployed and the carrier assembly initially advanced, device 1000 functions in the manner described above with regard to other embodiments of the present invention and thus will not be described in detail with regard to this embodiment.

As discussed above, in some embodiments of the present invention, the housing 1380 may include an indicator window 1451 which is used to give a visual indication of the status of apparatus 1000. For instance, indicator window 1451 may, in some embodiments, visually indicate whether a tab spacer block 492 (FIG. 1A) is engaged with a locator assembly. Such an indication can indicate whether a closure element has been deployed, is armed for deployment, or whether the user needs to take further actions to prepare apparatus 1000 to deploy a closure element.

In some embodiments, throw reducer 1010 may further include a slider 1012 which fits over the exterior of housing 1380 in a manner that covers indicator window 1451. Accordingly, slider 1012 may optionally have a slot 1014 formed therein that allows the physician or clinician to use view indicator window 1451. For example, in the illustrated embodiment, slot 1380 has an elongated configuration that allows window 1451 to remain visible to the user of apparatus 1000 regardless of the position of slider 1012 on housing 1380. It will also be appreciated that other configurations of slot 1380 are possible, and that in some embodiments, slot 1380 may not be necessary inasmuch as window 1451 may not be covered by slider 1012, or slot 1380 may allow window 1451 to be covered at least at some positions of slider 1012.

As discussed above, slider 1012 may have a finger extension 1016 formed thereon, or connected thereto, to allow a physician or clinician to easily slide slider 1012 relative to housing 1380. Finger extension 1016 is optionally contoured to be received by a physician's hand and/or finger and may also be formed of one or more components so as to allow the physician or clinician to grip or hold the slider 1012. As illustrated in FIG. 10B, finger extension 1016 can include a first portion 1016a and a second portion 1016b on either side of slot 1018. In this configuration, after slider 1012 has been advanced to the distal position illustrated in FIG. 10B and when trigger extension 1405 is then distally advanced with respect to housing 1380 and slider 1012, trigger extension 1405 can be aligned with finger extension 1016 and may be nested within finger extension portions 1016a and 1016b, thereby allowing trigger extension 1405 to be fully advanced in the distal direction along housing 1380.

While two finger extension portions 1016a and 1016b are illustrated in FIG. 10B, it will be appreciated that this is exemplary only. In other embodiments, for example, a single finger extension may be formed on only one side of slot 1018. In other embodiments, a finger extension may be a single, integral component which is molded or shaped to include a gap therein for receiving and nesting with trigger extension 1405. In other embodiments, the finger extension 1016 may be aligned with slot 1018 and does not nest with trigger extension 1405. In still other embodiments, finger extension 1016 is eliminated and one or more contours or ridges are instead formed on the surface of slider 1012 to allow a user to grip the exterior of slider 1012 and advance it distally. In another embodiment, a ratchet mechanism can be linked to slider 1012, such that by rolling the ratchet controller, slider 1012 is advanced relative to housing 1380. In still other embodiments, no other gripping component may be included in connection with slider 1012.

As will be appreciated in view of the disclosure herein, throw reducer 1010 may be configured to be permanently coupled with housing 1380, or may be selectively detachable therefrom. In one embodiment, for example, apparatus 1000 is modular and slider 1012 is a selectively attachable and/or removable component which can be selected and optionally installed for use by the physician or clinician. For example, slider 1012 may comprise two or more discrete components that can be selectively removed from housing 1380. For instance, a first portion may include one or more flexible arms having detents which mate with one or more corresponding gaps formed in a second portion. A button or release mechanism may then be employed to allow the user to selectively release such lock-fitting portions.

Additionally, while slider 1010 is disclosed as including a slider 1012 which fits around, and slides relative to, housing 1380, it will be appreciated that this embodiment is exemplary only and that in other embodiments, other configurations are possible. For example, slider 1012 may, in some embodiments, not include an outer sleeve. For instance, a slider 1012 may instead be integrated within housing 1380 and connected to trigger extension 1405 so as to advance trigger extension 1405. For instance, an internal slider 1012 may have a finger grip 1016 which slides within slot 1382 of housing 1380 and which is internally linked to trigger extension 1405.

In another embodiment of a modular apparatus 1000, slider 1012 may be hinged such that it can be selectively folded around housing 1380. The halves may thereafter be secured together by using a lock-fit mechanism, screws, clasps, or other suitable mechanical fasteners. In an embodiment in which slider 1012 is permanently coupled with housing 1380, separate portions of slider 1012 may be molded around housing 1380 and heated to permanently attach the portions together. In other embodiments, separate portions of slider 1012 may be fitted around housing 1380 and secured using an adhesive, rivet, or other non-removable fastener. It will also be appreciated that a lock-fit feature which does not include a release mechanism may also substantially permanently attach separate portions of slider 1012 around housing 1380.

In view of the disclosure herein, it will be appreciated that any variety of different throw reducers may be used in accordance with the principals of the present invention, such that throw reducer 1010 is therefore exemplary only and therefore not limiting of a throw reducing mechanism which may be used in connection with the principals of embodiments of the present invention. Indeed, an alternative throw reducer 2000 is illustrated in FIG. 11 which may also be used in connection with some embodiments of the present invention.

As discussed above, in some embodiments, a closure element delivery apparatus may include a locator assembly block, plunger or other device configured to cause the distal end of a locator assembly to transition from an unexpended state to an expanded state. As illustrated in FIG. 1A and as described above, for example, a locator assembly block 280 may be located at a proximal end of the delivery apparatus and configured to allow a user to apply a force causing distal movement of locator assembly block 280. This movement may move a distal body 290 relative to a control member 250, thereby causing the distal end of the locator device to change to an expanded state. Optionally, the locator assembly block 280 may include locking elements 284a-b and 285a-b which lock the locator device in its expanded state. Thereafter, a trigger extension may be distally advanced relative to the apparatus housing to prepare the apparatus for deployment of the closure element.

In the embodiment of FIG. 1A, a user may use both hands to properly position the delivery apparatus relative to the tissue and/or puncture site to be closed, and may thereafter be required to remove at least one hand to apply a force sufficient to move the locator assembly block distally. In FIG. 11, however, apparatus 2000 may allow a physician or other user of apparatus 2000 to more efficiently expand the locator assembly. For instance, a physician can expand the locator device without removing a hand or using a second hand to apply a separate force to a locator assembly block or other similar device. Instead, movement of a throw reducer 2010 may be configured to expand the distal tip or other portion of the locator assembly.

Referring now to FIG. 11, an alternative embodiment of the apparatus is shown in accordance with another exemplary embodiment of the present invention. The apparatus of the alternative embodiment is functionally similar to that of the device previously described above and shown in FIGS. 10A and 10B. Accordingly, certain features will not be described in relation to the alternative embodiment wherein those components function in the manner as described above and are hereby incorporated into the alternative embodiment described below.

In the embodiment illustrated in FIG. 11, a throw reducer 2010 is coupled with a housing 2380 of the delivery apparatus 2000. In the illustrated embodiment, throw reducer 2010 includes a slider 2012 which fits like a sleeve around the exterior of housing 2380, and is configured to move relative thereto. In this embodiment, slider 2012 also includes a gripping member 2016 which is, in this embodiment, a finger extension contoured and/or padded to comfortably accept the finger or hand of a user. In this manner, the user can use gripping member 2016 to grip and manipulate slider 2012.

A locator assembly block (not shown) may also extend in a proximal direction from the proximal end of housing 2380. The locator assembly block, which may be functionally and/or structurally similar to locator assembly block 280 of FIG. 1A, or the plunger 1280 of FIG. 10A, may be adapted to expand the distal tip of a locator assembly, and may optionally lock the distal tip in the expanded state. As illustrated in FIG. 11, slider 2012 can also extends proximally from the proximal end of housing 2380 and can substantially encompasses the locator assembly block, which is hidden within slider 2012. Slider 2012 may substantially enclose the lateral sides of the locator assembly block and, in this embodiment, can also include a closed proximal end 2112a to envelop the proximal end of the locator assembly block.

As described above with reference to throw reducer 1000 of FIGS. 10A and 10B, throw reducer 2000 may be advanced distally along housing 2380. In some configurations, when throw reducer 2000 is advanced distally, slider 2012 also engages trigger extension 1405 and causes it to move distally. As slider 2012 thus moves distally, trigger extension 2405 can remain a substantially fixed distance from gripping member 2016, and thus move closer to handle 2391 of apparatus 2000.

In addition, in the illustrated embodiment in which proximal end 2012a of slider 2012 can enclose locator assembly block 2380, distal advancement of slider 2012 can also cause the closed proximal end 2012a of slider 2012 to engage the proximal end of the locator assembly block. As slider 2012 continues to move distally, it can thus apply a distally-directed force to locator assembly block 2380 which moves locator assembly block 2380 distally, thereby causing the distal tip of a locator assembly to transition from an unexpanded state to an expanded state. In the expanded state, the distal tip can then be selectively pressed against tissue surrounding a puncture site so as to properly locate apparatus 2000 for deployment of a closure element. Accordingly, a user can expand the distal tip of a locator assembly by moving slider 2012, without applying a separate force to the proximal end of locator assembly block 2380.

As described herein, a locator assembly block may include a locking mechanism that locks the locator assembly block in a predetermined position that causes the distal tip of the locator assembly to remain in an expanded state. It will be appreciated that in the illustrated embodiment, the locking mechanism in the locator assembly block can optionally be removed. For instance, as the user continues to apply a distally directed force to gripping member 2016 of slider 2012, the locator assembly block is substantially prevented from moving in a proximal direction and from causing the distal tip of the locator device to transition back to an unexpanded state. Thus, while using slider 2012, a locking mechanism on the locator assembly block may be unnecessary.

In other embodiments, after moving slider 2012 to its distal position on housing 2380, the physician or clinician may desire to release slider 2012. For example, a physician may release gripping member 2016 of slider 2012 to grasp a stabilizer portion 2391b of handle 2391. In such a case, it may be desirable for a locking mechanism to prevent the locator assembly block from inadvertently moving proximally. Accordingly, a locking mechanism in the locator assembly block may be desirable.

The locking mechanism may, however, also be displaced from the locator assembly block. For instance, in the illustrated embodiment, housing 2380 includes a handle 2391a that includes a first handle portion 2391a contoured to be gripped by a user. Apparatus 2000 of the illustrated embodiment also includes a second handle 2392. Handle portion 2391 and handle 2392 may be contoured or otherwise configured to mate with the distal end of slider 2012 and may optionally be configured to lock with respect thereto.

Specifically, in the illustrated embodiment, slider 2012 includes a first locking portion 2020a which extends vertically from slider 2012. Handle 2392 of housing 2380 includes a mating locking portion 2393a. As slider 2012 moves toward and engages handle 2392, first locking portion 2020a mates with locking portion 2393a, thereby at least temporarily and selectively locking slider 2012 relative to housing 2380. By locking slider 2012 in place, the locator assembly block can also be locked in place and be substantially prevented from moving proximally.

First locking portion 2020a and locking portion 2939a may interlock in any suitable manner. For instance, interlocking detents and slots may be used to lock slider 2012 to handle 2392. Alternatively, an interference fit may interlock the components, or a clasp, buckle, pin-and-hole, or other interlocking mechanism may be used. Additionally, or in the alternative, a second locking portion 2020b may be formed on gripping member 2016 and can have a mating locking portion 2393b on first handle portion 2391b.

As noted above, in embodiments in which slider 2012 mates with or is otherwise secured in place relative to housing 2380, the securement of slider 2012 may be permanent or temporary. For instance, in the illustrated embodiment, first locking member 2020a includes a release button 2022 which may be used to release slider 2012 from housing 2392. In other embodiments, however, such as where apparatus 2000 is a single use device, when slider 2012 is secured in place relative to housing 2380, it may be permanently secured thereto.

While the foregoing description describes handles 2391 and 2392 as components of housing 2380, it will be appreciated that this is exemplary only and that in other embodiments handles 2391 and 2392 may be discrete components separable from housing 2380. For example, in one embodiment, handle 2392 is integrally formed with housing 2380 while handle 2391a is a modular component which is selectively attachable and/or detachable from housing 2380. In other embodiments, handle 2392 may alternatively or additionally be selectively removable. In still other embodiments, handle 2391 and handle 2392 form a single integral component which can be selectively detached or attached to housing 2380. In yet another embodiment, first handle portion 2391a and second handle portion 2391b are also separate components which may be selectively coupled with housing 2380 or may be integrally formed therewith.

Figure 12:
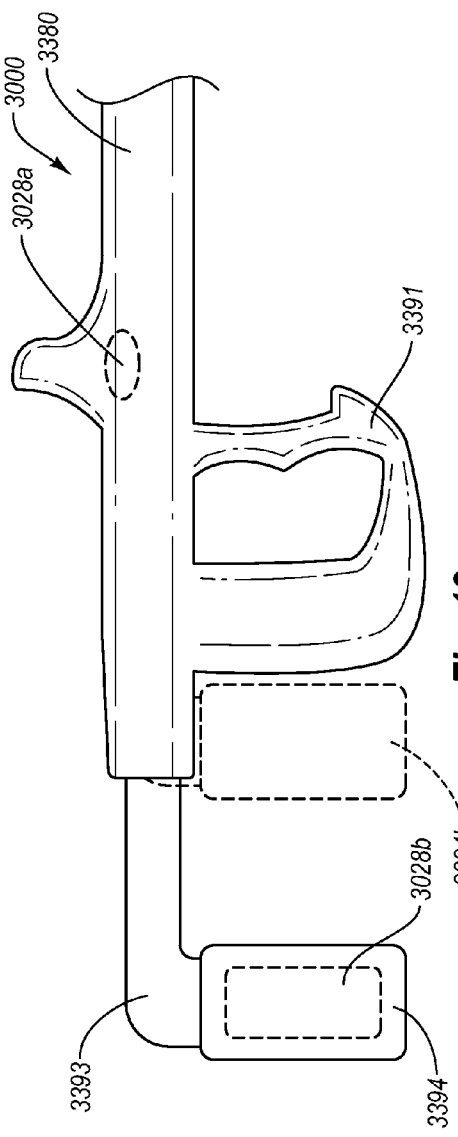

Now turning to FIGS. 12-14 still other alternative embodiments of a delivery apparatus are shown in accordance with other exemplary embodiments of the present invention. The apparatus of the alternative embodiments are functionally similar to that of the devices previously described above and shown in FIGS. 1-11 in most respects. Accordingly, certain features will not be described in relation to the alternative embodiment wherein those components function in the manner as described above and are hereby incorporated into the alternative embodiment described below.

For instance, as described above and not by way of limitation, apparatus may include a housing, locator assembly, carrier assembly, and/or triggering system. As desired, however, the locator assembly, carrier assembly and triggering system may each be provided, in whole or in part, as one or more integrated assemblies. Portions of the locator assembly, triggering system and/or carrier assembly can also be used as part of a suitable apparatus. Alternatively, modified versions of the locator assembly, triggering system and/or carrier assembly can be used, including the use of modular components which may be selectively added to one or more of the locator assembly, carrier assembly, triggering system, or the housing.

As illustrated in FIG. 12, a delivery apparatus 3000 according to the present invention can include a housing 3380, which includes a grasping portion 3391, which may be a handle. Grasping portion 3391 may optionally be gripped by a user to facilitate handling of apparatus 3000 and positioning of apparatus 3000 for deployment of a closure element into the tissue or puncture site of a patient. As disclosed herein, grasping portion 3391 may be integrally formed in housing 3380, or may be modular such that it can be selectively attached to, or detached from, housing 3380.

To further facilitate handling, manipulation and positioning of the delivery apparatus 3000, one or more stabilizers 3394 may be coupled with housing 3380. Stabilizer 3394 may be, for example, positioned at a distal end of housing 3380. As a physician or clinician positions apparatus 3000 for use, the physician or clinician may grasp grasping portion 3391 with one hand. The physician or clinician's other hand may then grip or be placed against stabilizer 3394 which is located more proximate the patient. In this manner, the physician can gain additional leverage when using apparatus 3380, thereby increasing control of apparatus 3380 at or near the patient.

As shown in FIG. 12, an exemplary stabilizer 3394 may extend from the distal end of housing 3380. In the illustrated embodiment, a linkage 3393 couples stabilizer 3394 to housing 3380, although any suitable connecting mechanism may be employed. In this embodiment, for example, linkage 3393 may be an elongate member which is positioned within housing 3380 and slides relative thereto. In other embodiments, linkage 3393 may be a telescoping member which expands and contracts, and/or a sliding member which slides around the exterior of housing 3380.

In this example embodiment, linkage 3393 connects stabilizer 3394 to housing 3380. Linkage 3393 may further be retractable within housing 3394, thereby allowing a user to selectively determine whether to use stabilizer 3394, and/or the manner in which stabilizer 3394 is used. For instance, when apparatus 3000 is being used by a physician or clinician to deploy a closure element, stabilizer 3394 may be in an extended position such as that illustrated in FIG. 12. If the physician elects not to utilize stabilizer 3394 or requires a reduced distal extension for use of apparatus 3000, or while apparatus 3000 is being packaged, shipped or stored, linkage 3393 may be retracted inside housing 3380, thereby drawing stabilizer 3394 to a location adjacent handle 3391. For example, stabilizer 3394 may be drawn to the position 3394' illustrated in phantom lines in FIG. 12. In other cases, stabilizer 3394 may be removed entirely from housing 3380.

In some embodiments, stabilizer 3394 can be selectively positioned at either of the discrete positions illustrated in FIG. 12. In other embodiments, however, a physician or other user can selectively locate stabilizer 3394 at any of numerous possible positions. For instance, stabilizer 3394 may be positioned in any of a variety of different discrete or non-discrete positions between positions 3394 and 3394'.

An extendable stabilizer, such as that illustrated in FIG. 12, can be implemented in any of a variety of manners. For example, according to one embodiment, linkage 3393 comprises an elongate shaft which slideably engages a corresponding channel (not shown) in housing 3380. Thus, to reposition stabilizer 3394, a user may grasp stabilizer 3394 and apply a force to move it in the distal or proximal direction, as desired. Such a force can cause the elongate shaft of linkage 3393 to slide within the channel in housing 3380 to the desired position.

In some embodiments, stabilizer 3394 may also be temporarily or permanently locked in any of a variety of different positions. For instance, stabilizer 3394 may lock at a distalmost position (e.g., at position 3394), at a proximal-most position (e.g., at position 3394'), and/or at any desired location between. Further, any suitable locking mechanism may be used in connection with telescoping stabilizer 3391. For instance, according to one embodiment, linkage 3393 may employ a ratchet mechanism such that as linkage 3393 moves relative to housing 3380, it locks in place in relatively small, discrete increments. In other embodiments, linkage 3393 may include one or more flexible detents and the channel (not shown) within housing 3380 may include corresponding grooves. As linkage 3393 is then moved within the channel, the flexible detents may engage the corresponding grooves to lock linkage 3393 and stabilizer 3394 at a predetermined location. Optionally, such grooves may be spaced along the length of the channel to provide multiple locations at which stabilizer 3394 can be secured in place.

In still other embodiments, a rotating locking mechanism may be employed, as is known in the art. For instance, a physician may rotate stabilizer 3394 around an axis passing through the center of the extendable, elongate shaft of linkage 3393, and which is generally parallel to the longitudinal axis of elongate housing 3393. When at position 3394', rotation of stabilizer 3394 may release stabilizer 3394 from a locked state so as to allow linkage 3393 to slide through a respective channel. When stabilizer 3394 reaches a desired position, the physician can rotate stabilizer 3394 around the same axis to again lock stabilizer 3394 relative to housing 3380. According to one embodiment, stabilizer 3394 rotates in a first direction (e.g., clockwise) to release it from a locked state, and rotates in an opposite direction (e.g., counter-clockwise) to place it into a locked state. As will also be appreciated, the locking mechanism can require rotation of any number of degrees to change between a locked and unlocked state. For instance, stabilizer 3394 may be rotated 90°, 180°, 360° or any other number of degrees, as desired, to release or engage a locking mechanism of stabilizer 3394.

Any suitable release mechanism may also be used in connection with any corresponding locking mechanism employed with respect to stabilizer 3394. Such a release mechanism may also have any other suitable configuration or position. For example, in the illustrated embodiment, the release mechanism may include button 3028a and/or 3028b to release the locking mechanism. For instance, while pressing one of buttons 3028a or 3028b, a ratchet mechanism may be disengaged so as to allow linkage 3393 to freely slide relative to housing 3380. As illustrated, a release mechanism such as buttons 3028a and 3028b may be located in any suitable location. For instance, as illustrated in phantom lines, a release mechanism may be positioned on the housing 3380 (e.g., button 3028a) or may be positioned on stabilizer 3394 (e.g., button 3028b).

It will also be appreciated in view of the disclosure herein that stabilizer 3394 is an optional component and may further be a modular, in that it can be selectively attached or detached from housing 3380, as desired. For instance, in one embodiment, by releasing an optional locking mechanism, stabilizer 3394 may be extended from housing 3380 and entirely removed therefrom. In another embodiment, each of release buttons 3028a and 3028b may be used. For example, by pressing button 3028a, a physician or other user may be able to remove stabilizer 3394 and linkage 3393 from housing 3380, while button 3028b may be used merely to selectively lock stabilizer 3394 when stabilizer 3394 is coupled with housing 3380.

Referring now to FIGS. 13 and 14, alternative embodiments of an apparatus employing a movable stabilizer are shown in accordance with additional exemplary embodiments of the present invention. The apparatus of the alternative embodiments are functionally similar to that of the device previously described above and shown in FIG. 12 in most respects. Accordingly, certain features will not be described in relation to the alternative embodiment wherein those components function in the manner as described above and are hereby incorporated into the alternative embodiment described below.

As illustrated in FIG. 13, a closure element delivery apparatus 4000 is illustrated which includes an extendable stabilizer 4394. As illustrated in this embodiment, stabilizer 4394 can be coupled with a handle 4391 of apparatus 4000, and may optionally extend therefrom to a position desired by a physician, clinician or other user.

In particular, and as illustrated in FIG. 13, a linkage 4393 may connect stabilizer 4394 to handle 4391. Although linkage 4393 can include any suitable connection mechanism, in the illustrated embodiment, linkage 4393 includes a shaft which extends from handle 4391 to stabilizer 4028b. Linkage 4393 may also be extendable in any suitable manner. For example, linkage 4393 may be of a fixed size and slide within or around handle 4391. In another embodiment, and as disclosed above, linkage 4393 may be configured to expand or stretch, as necessary.

To facilitate use and/or control of apparatus 4000, stabilizer 4394 may be positioned by a clinician in any of a variety of different locations. For example, stabilizer 4394 may be positioned in an extended position such as that illustrated in FIG. 13. In such a position, the clinician may grip handle 4391 with one hand, and may place the other hand on extended stabilizer 4394 to obtain greater control of apparatus 4000 at or near the patient in whom a closure element is being deployed. Other positions may include, for example, a retracted position 4394', as illustrated in phantom lines. As further disclosed herein, stabilizer 4394 may further be positioned at any other suitable location between positions 4394 and 4394', or may be removed entirely, as desired by the user.

As further disclosed above, particularly with respect to FIG. 12, it will also be appreciated that stabilizer 4394 can be configured to lock in a suitable location, although this feature is optional. For example, a clamp or clasp may be included on linkage 4393 which, when engaged, locks linkage 4393 relative to housing 4380 of apparatus 4000, at any discrete or non-discrete position. Other locking mechanisms may alternatively be utilized, and a non-exclusive list of various suitable locking mechanisms is disclosed herein. Such locking mechanisms are, however, merely optional. For example, in one embodiment, apparatus 4000 may not include any locking mechanism for selectively or permanently locking stabilizer 4394 at any particular location. For example, in one embodiment, the application of pressure to stabilizer 4394, by the clinician using apparatus 4000, may be sufficient to maintain stabilizer 4394 at a desired position.

Where a locking mechanism is employed, various systems for releasing the mechanism and/or for allowing for selective attachment or detachment of stabilizer 4394 can also be employed. For instance, one or more release buttons, such as buttons 4028a, 4028b, may optionally be included on stabilizer 4394, handle 4391, housing 4380, or even linkage 4393.

FIG. 14 illustrates another example embodiment of a closure element delivery apparatus 5000, and is similar in many regards to the delivery apparatuses illustrated in FIGS. 12 and 13. In FIGS. 12 and 13, however, an enclosed gripping element or handle can be coupled with the respective housing, and a separate stabilizer may be used. In contrast, apparatus 5000 may include a stabilizer which is integrated with the handle.

In particular, in the illustrated embodiment, a handle 5391 is coupled with housing 5380. As disclosed herein, handle 5391 can be coupled to housing 5380 in any suitable manner. For instance, handle 5391 may be at least partially formed as an integral component of housing 5380. In other embodiments, however, handle 5391 may be modular and can be entirely or partially removable from housing 5391. In this manner, a user can select what style of handle and/or what features to use in connection with delivery apparatus 5000.

As shown in FIG. 14, a handle 5391 can be coupled to housing 5380, and can include two or more separate components. For example, handle 5391 can include a first grasping portion 5391a which may be adapted to be grasped by one hand of the user. As disclosed herein, the same hand that grasps grasping portion 5391a may also be used to advance a triggering assembly, such as with a trigger extension. To facilitate the comfort of apparatus 5000, first grasping portion 5391a may optionally be contoured to receive the fingers of the user in a comfortable manner, and/or can include padding or another yielding material designed to provide a comfortable grip for the user.

In the illustrated embodiment, first grasping portion 5391a can be open on its distal side. Optionally, a second grasping portion 5391b can be coupled to housing 5380. Second grasping portion 5391b can mate with first grasping portion 5391a and close, or substantially close, handle 5391. As further illustrated in FIG. 14, second grasping portion 5391b can further be adapted to act as a stabilizer, as also described herein. For example, second grasping portion 5391b can be extendable and retractable relative to housing 5380. In the illustrated position of second grasping portion 5391b, for example, a user of apparatus 5000 can grasp first grasping portion 5391a with one hand and then grasp, or rest a second hand on, second grasping portion 5391b to improve the user's control of apparatus 5000. A linkage 5393 as disclosed herein can extend from housing 5380 and/or first grasping portion 5391a to allow extension and retraction of second grasping portion 5391b. For instance, when second grasping portion 5191b is in a retracted position, such as position 5391b' illustrated in phantom lines, second grasping portion 5391b can be adjacent first grasping portion 5391a, thereby giving handle 5391 a closed appearance. It will be appreciated that a user of apparatus 5000 can use second grasping portion 5391b as a stabilizer in either the extended or retracted position, or at any position therebetween.

Figure 15:
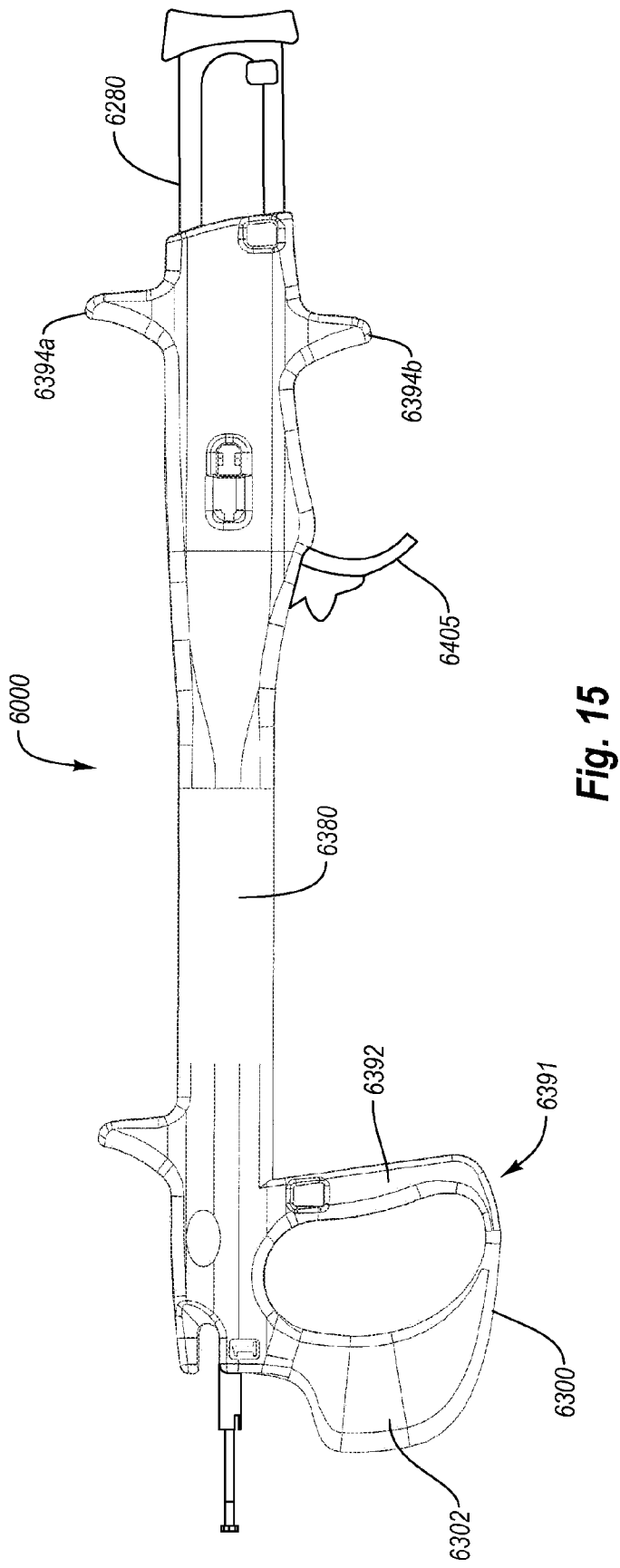
FIG. 15 illustrates an example of a delivery device having various finger and hand grips for effectively handling the delivery device.
Figure 16A:
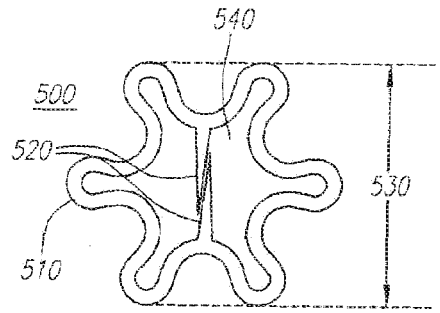
FIGS. 16A-16G illustrate various embodiments of closure elements that can be utilized with the apparatus of the present invention.
Figure 16B:
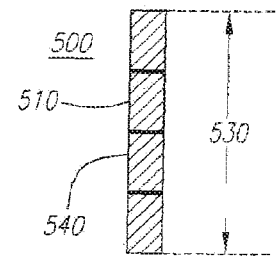
Figure 16C:
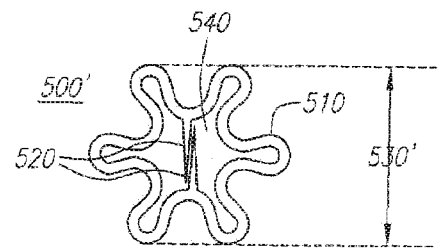
Figure 16D:
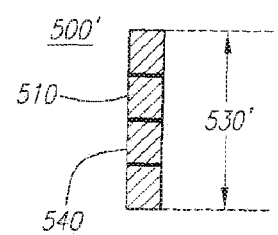
Figure 16E:
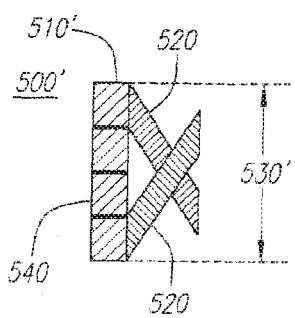
Figure 16F:
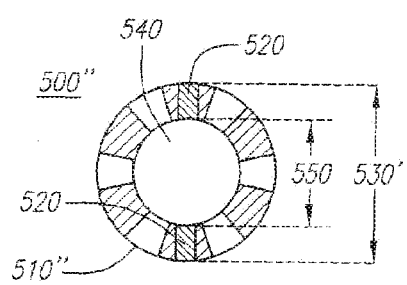
Figure 16G:
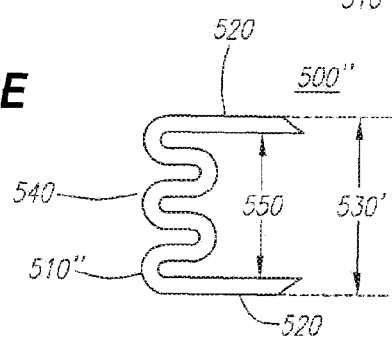

Now turning to FIG. 15, another example embodiment of a delivery apparatus 6000 is illustrated. Apparatus 6000 can include a housing 6380 which may be a single, integral piece, or can comprise discrete halves, as disclosed herein. Housing 6380, either as a single integral piece, or collectively by multiple, discrete pieces, can form one or more handle, hand grip, or finger portions which a physician or clinician can grip or hold to manipulate the apparatus 6000. As illustrated, for example, the apparatus 6000 can include a grasping portion 6391 at a distal end, and finger grips 6394a and 6394b on the proximal end of housing 6380 to facilitate use of a locator assembly, and specifically a plunger 6280 (FIGS. 10A and 10B).

In addition, the apparatus 6000 can include handle, hand grip, or finger portions disposed on the distal end of housing 6380 configured to be engaged by a user when advancing a trigger assembly, including trigger extension 6405 to deploy closure element 500 (FIG. 1A). This handle or handle portion or hand grip portion can include a shaped grasping portion 6300 and an elongate grasping portion 6392 spaced apart from the shaped grasping portion 6300. Each of the portions 6392 and 6300 may be contoured to be received by a user's hand. For instance, the grasping portion 6300 can provide a stable base upon which the physician or clinician can move the device or apparatus as the closure element is positioned and deployed. This grasping portion 6300 can have a shaped portion 6302 having a curved configuration that can receive at least a thumb or finger of the physician as the physician or clinician holds the apparatus 6000. The curved configuration or profile allows the physician to grasp the handle or handle grip portion 6300 while resting their hand, wrist or forearm upon a patient during the procedure, such as during deployment of the closure element, thereby providing stability during use of the device.

It will be understood that although reference is made to one particular configuration of the handle, hand grip, or finger portions, one skilled in the art will appreciate and can identify various other configurations of handle portion that can perform the function of providing a stable base for manipulation of the apparatus 6000. For instance, and not by way of limitation, the handle portion can be planar rather than curved. Further, the handle portion can include one or more finger receiving holes. In addition, the handle portion can include a material to provide cushioning or comfort to the physician and/or clinician. For example, flexible, yielding, or elastic materials can be formed or applied to all or a portion of the handle portion.

Additionally, handle portion 6300 can be wholly, or partially, molded with, or otherwise integral with housing 6380. Alternatively, one more components of handle portion 6300 may be selectively removable and/or extendable, as described herein. Furthermore, finger grips 6394a, 6394b can also have any suitable configuration and can be, for example, curved or planar. Additionally, finger grips 6394a, 6394b can be integral with housing 6380. Alternatively, one or both of finger grips 6394a, 6394b can be selectively removable and/or attachable to housing 6380. In this manner, finger grips 6394a, 6394b can be modular components which can be selectively used by a physician or clinician, if desired.

Referring now to FIGS. 16A-16G illustrating embodiments of a closure element that can be used as part of or with the apparatus 100. The closure element, generally identified with reference numeral 500, may have a generally annular-shaped body defining a channel and one or more barbs and/or tines for receiving and engaging the blood vessel wall and/or the tissue around the opening. Although the closure element has a natural shape and size, the closure element can be deformed into other shapes and sizes, as desired, and can be configured to return to the natural shape and size when released. For example, closure element 500 can have a natural, planar configuration with opposing tines and a natural cross-section. The closure element can be formed from any suitable material, including any biodegradable material, any shape memory material, such as alloys of nickel-titanium, or any combination thereof. Additionally, it is contemplated that the closure element may be coated with a beneficial agent or be constructed as a composite, wherein one component of the composite would be a beneficial agent. As desired, the closure element may further include radiopaque markers (not shown) or may be wholly or partially formed from a radiopaque material to facilitate observation of the closure element using fluoroscopy or other imaging systems. Exemplary embodiments of a closure element are disclosed in U.S. Pat. Nos. 6,197,042, 6,623,510, 6,461,364, 6,391,048, and 6,623,510. The disclosures of these references and any others cited therein are expressly incorporated herein by reference.

Figure 17A:
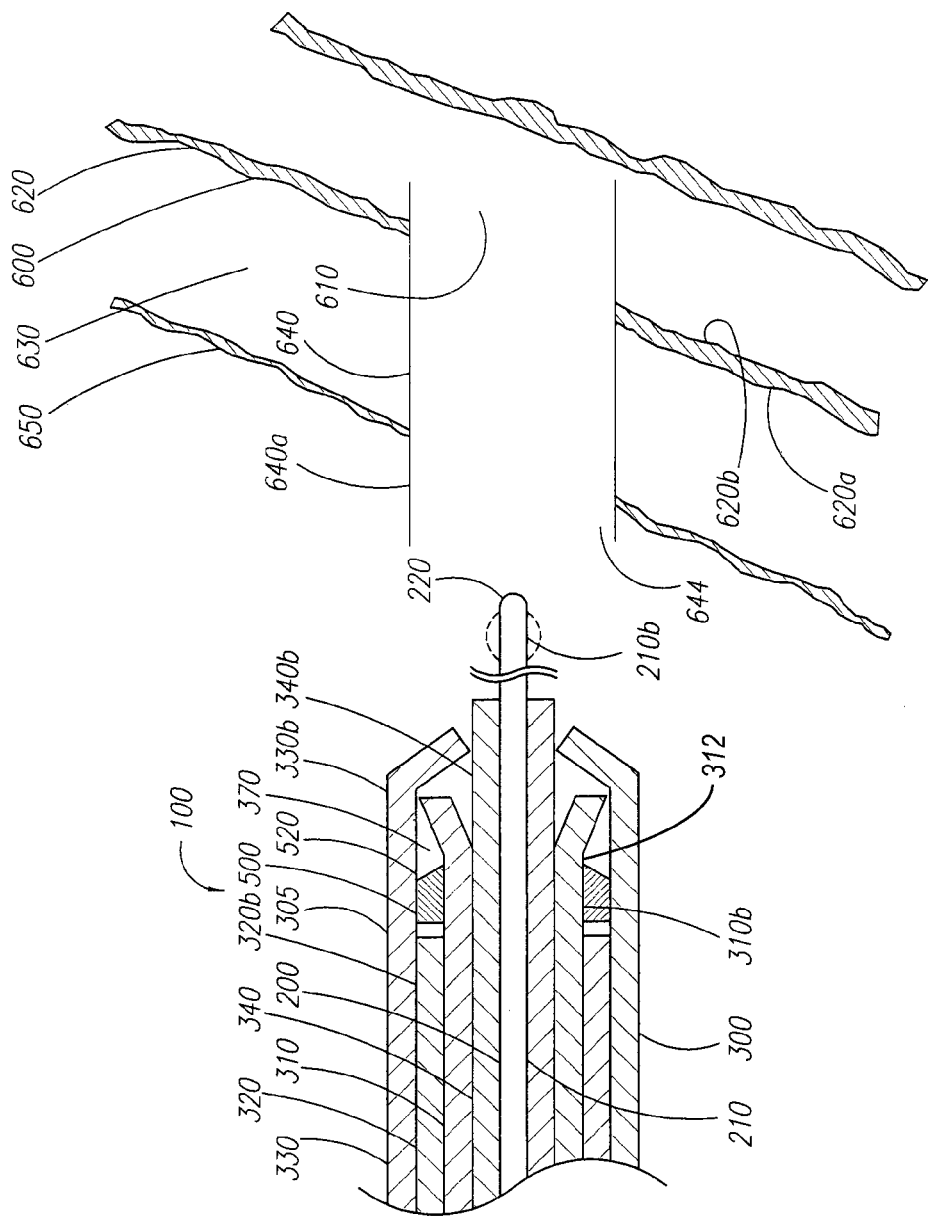
FIGS. 17A-17K illustrate various steps in the deployment of embodiments of the present invention.

As described previously, and with reference to FIG. 17A, closure element 500 can be disposed within the carrier assembly and adjacent to the distal end of pusher tube 320. As shown in FIG. 17A, for example, the reduced closure element 500 may be slidably received over distally-increasing cross-section 318b of distal end region 310b of carrier member 310 and disposed about periphery 312 of carrier member 310 adjacent to space 360. Since reduced cross-section 530 of reduced closure element 500 is less than cross-section 318b of distally-increasing cross-section 318b, reduced closure element 500 must be temporarily radially deformed to be received over distal end region 310b. Also, as reduced closure element 500' (FIG. 16C) is received over distal end region 310b, opposing tines 520 of reduced closure element 500' (FIG. 16C) engage distal end region 310b. Reduced closure element 500' (FIG. 16C) thereby forms substantially tubular closure element 500", illustrated in FIG. 16G, with the ends of the barbs and/or tines extending towards the distal end of the apparatus 100 (FIG. 1A).

The apparatuses of the present invention may be configured to be utilized with a sheath, wherein the sheath is inserted or otherwise positioned into an opening in a body comprising a lumen. The sheath generally comprises a substantially flexible or semi-rigid tubular member having a proximal end region and a distal end region and includes a predetermined length and a predetermined cross-section, both of which can be of any suitable dimension. The sheath forms a lumen that extends along a longitudinal axis or the sheath and substantially between the proximal and distal end regions. The lumen can have any suitable internal cross-section and is suitable for receiving one or more devices (not shown), such as a catheter, a guide wire, or the like. The lumen is configured to slidably receive the tubular body of the locator assembly and/or the tube set of the carrier assembly of the devices in accordance with the present invention.

Since the internal cross-section of the sheath may be less than or substantially equal to the predetermined cross-section of the cover member, the sheath may be configured to radially expand, such as by stretching, to receive the tube set. Alternatively, or in addition, the sheath may be advantageously configured to split as the tube set is received by, and advances within the lumen of the sheath, thereby permitting the apparatuses to access the blood vessel wall. To facilitate the splitting, the sheath can include one or more splits, such as longitudinal splits, each split being provided in a manner known in the art. Each split is configured to split the sheath in accordance with a predetermined pattern, such as in a spiral pattern. It will be appreciated that, when the internal cross-section of the sheath is greater than the predetermined cross-section of the cover member, it may not be necessary for the sheath to be configured to radially expand and/or split. In addition to, or as an alternative to, the apparatus may include a cutting means that initiates a tear line or split in the sheath when the sheath is engaged with the distal end of the apparatus.

The sheath may be advanced over a guide wire or other rail (not shown), which has been positioned through the opening and into the blood vessel using conventional procedures such as those described above. Preferably, the blood vessel is a peripheral blood vessel, such as a femoral or carotid artery, although other body lumens may be accessed using the sheath as will be appreciated by those skilled in the art. The opening, and consequently the sheath, may be oriented with respect to the blood vessel such as to facilitate the introduction of devices through the lumen of the sheath and into the blood vessel with minimal risk of damage to the blood vessel. One or more devices (not shown), such as a catheter, a guide wire, or the like, may be inserted through the sheath and advanced to a preselected location within the patients body. For example, the devices may be used to perform a therapeutic or diagnostic procedure, such as angioplasty, atherectomy, stent implantation, and the like, within the patents vasculature.

FIGS. 17A-17K illustrate one exemplary manner to deploy closure element 500 by apparatuses according to the present invention. For purposes of continuity, reference numbers to the first discussed embodiment are used, but it will be evident that other embodiments discussed above may be used in a similar fashion.

A sheath 640 may be inserted or otherwise positioned through a patient's skin 650 and tissue 630 and within the blood vessel 600 or other body lumen via the opening 610. This provides access to the blood vessel 600 through the blood vessel wall 620 for performance of a therapeutic or diagnostic procedure.

Figure 17B:
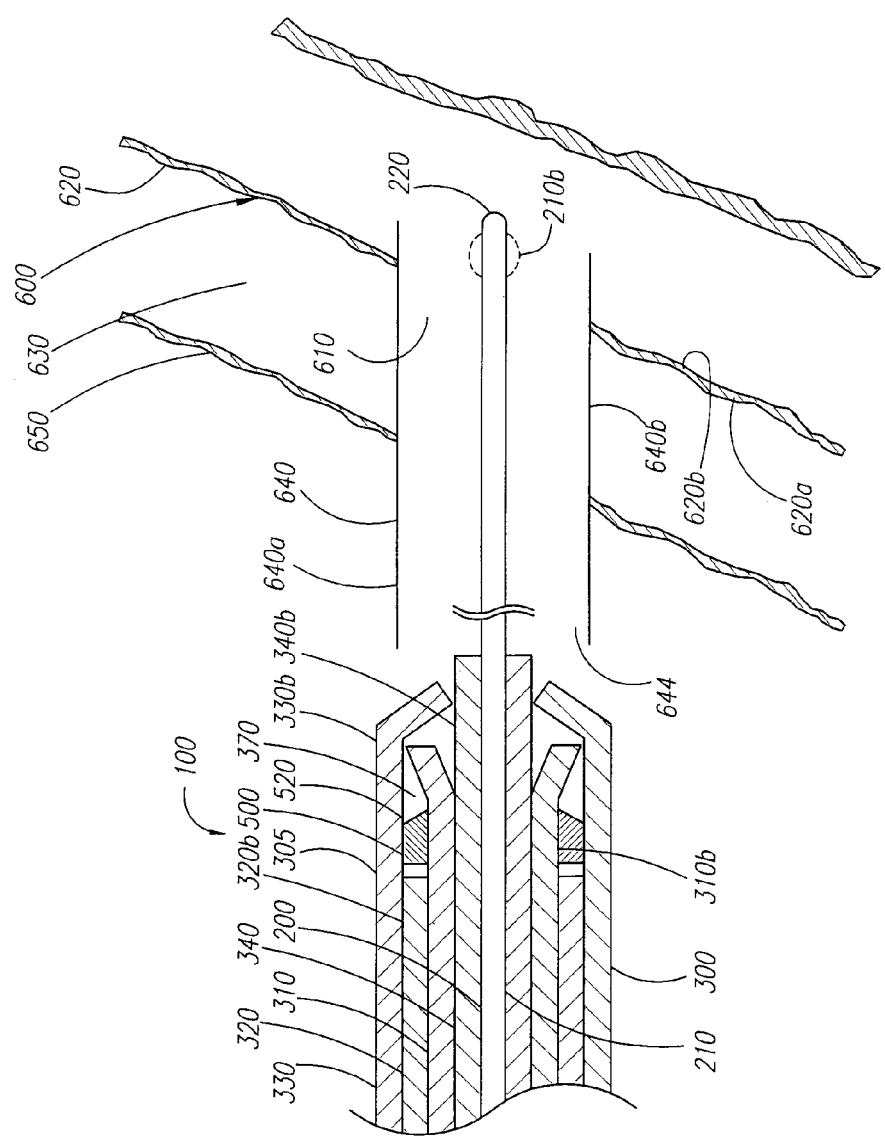
Figure 17C:
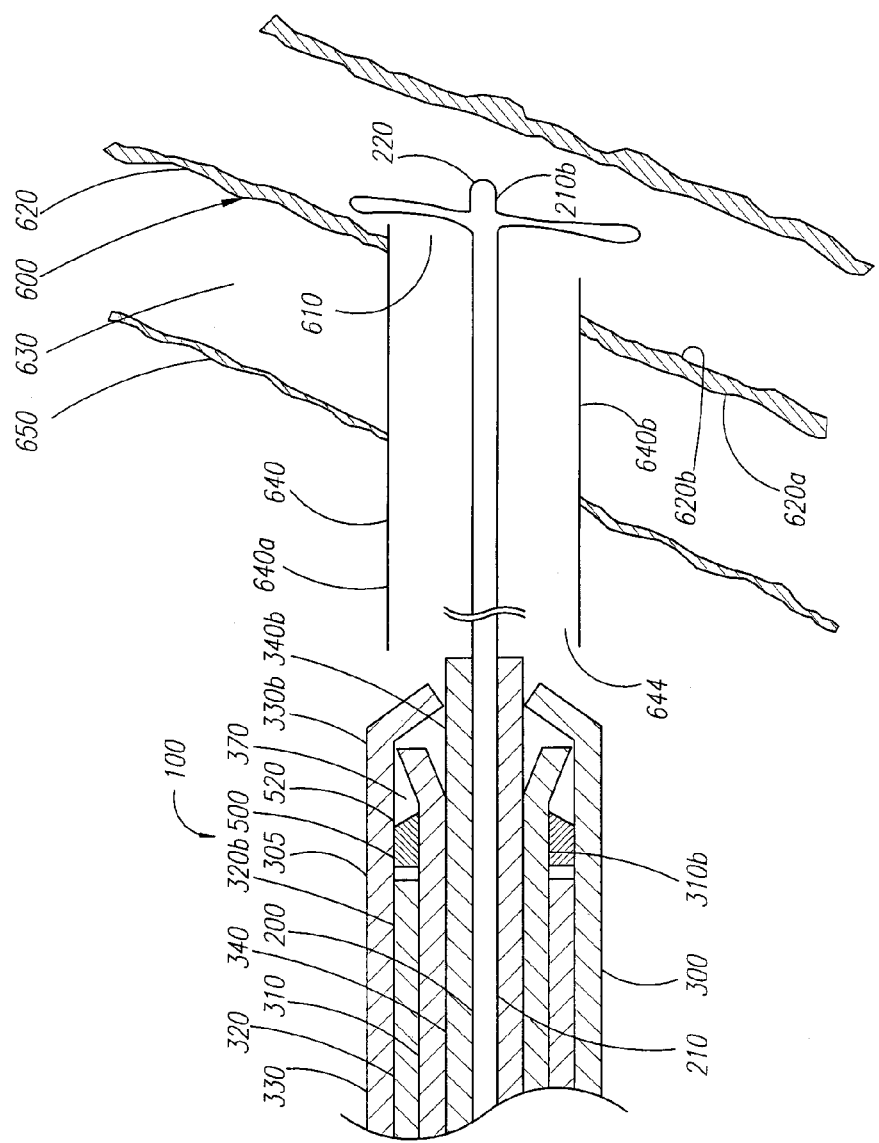

After the procedure is completed, the devices associated with the therapeutic or diagnostic procedure are removed from sheath 640, and apparatus 100 can be prepared to be received by lumen 644 of the sheath. Being in the unexpanded state, the distal end region 210b of tubular body 210 of the locator assembly 200 an be slidably received by the lumen and atraumatically advanced distally into the blood vessel 600, as illustrated in FIG. 17B. Once the distal end region 210b extends into blood vessel 600, distal end region 210b can transition from the unexpanded state to the expanded state by activating the switching system of locator assembly 200, and as illustrated in FIG. 17C. As discussed herein, particularly with reference to the embodiments described relative to FIGS. 10A-11, the carrier assembly may be partially advanced by using an external sleeve and/or when the locator assembly is transitioned from the unexpanded to the expanded state by pressing the locator assembly block distally with respect to the housing.

Figure 17D:
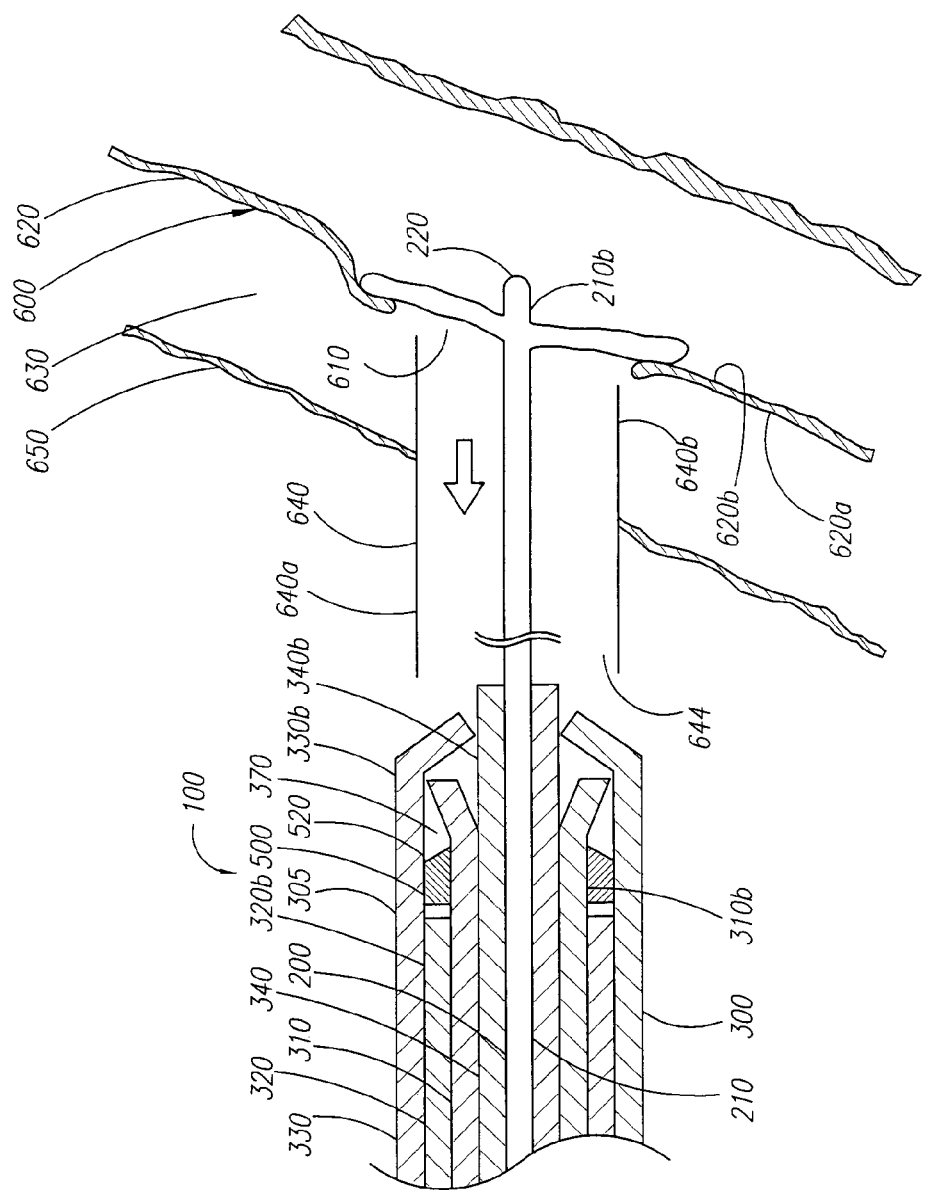
Figure 17E:
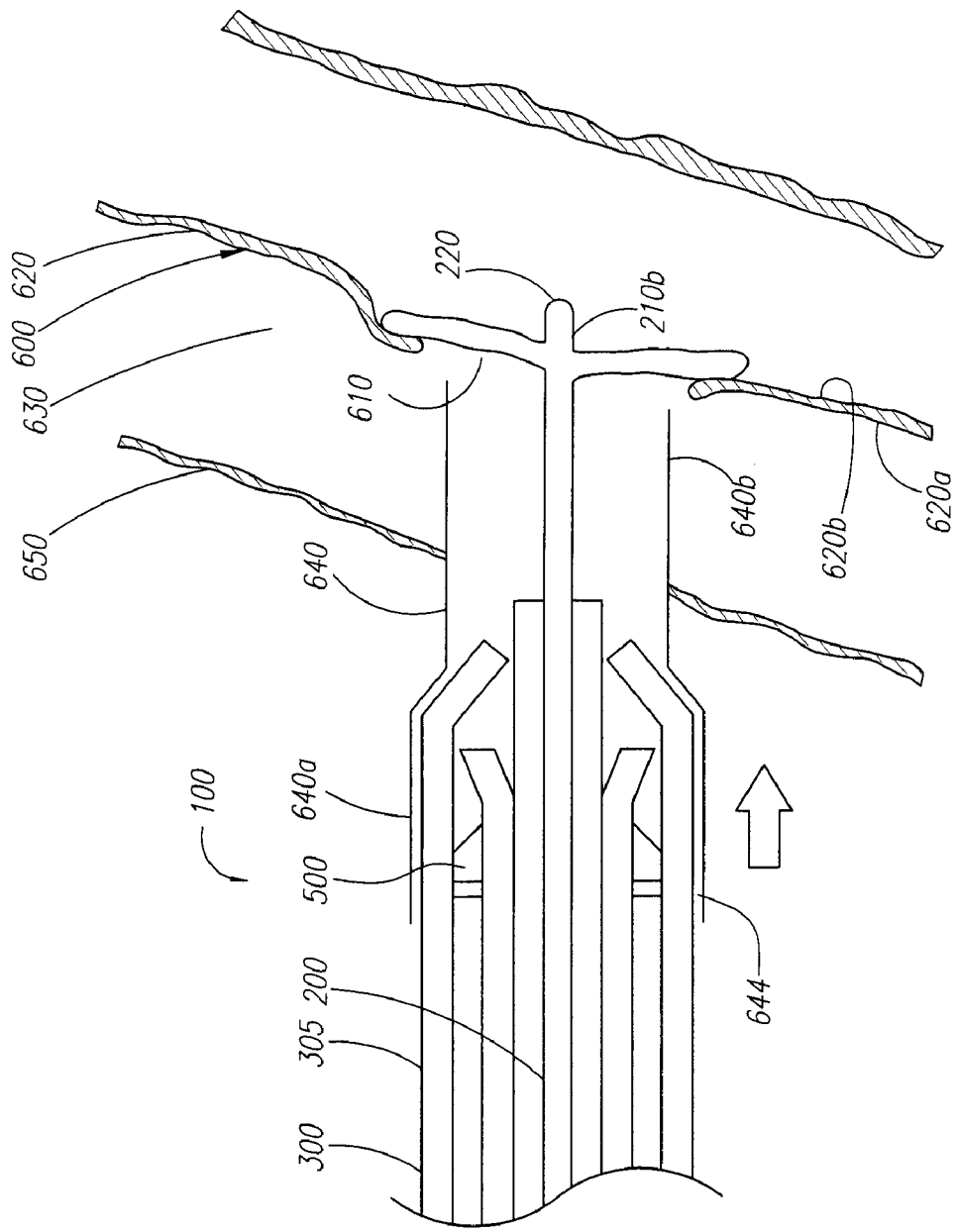

Turning to FIG. 17D, apparatus 100 and/or sheath 640 can then be retracted proximally until distal end region 210b is substantially adjacent to an outer surface 620b of blood vessel wall 620. Distal end region 210b thereby draws blood vessel wall 620 taut and maintains the proper position of apparatus 100 as blood vessel 600 pulsates. Since the expanded cross-section of distal end region 210b is greater than or substantially equal to the cross-section of opening 610 and/or the cross-section of lumen 644, distal end region 210b remains in blood vessel 600 and engages inner surface 620b of blood vessel wall 620. Distal end region 210b can frictionally engage inner surface 620b of blood vessel wall 620, thereby securing apparatus 100 to blood vessel 600. Sheath 640 can be retracted proximally such that distal end region 640b of sheath 640 is substantially withdrawn from blood vessel 600, permitting apparatus 100 to access blood vessel wall 620.

Figure 17F:
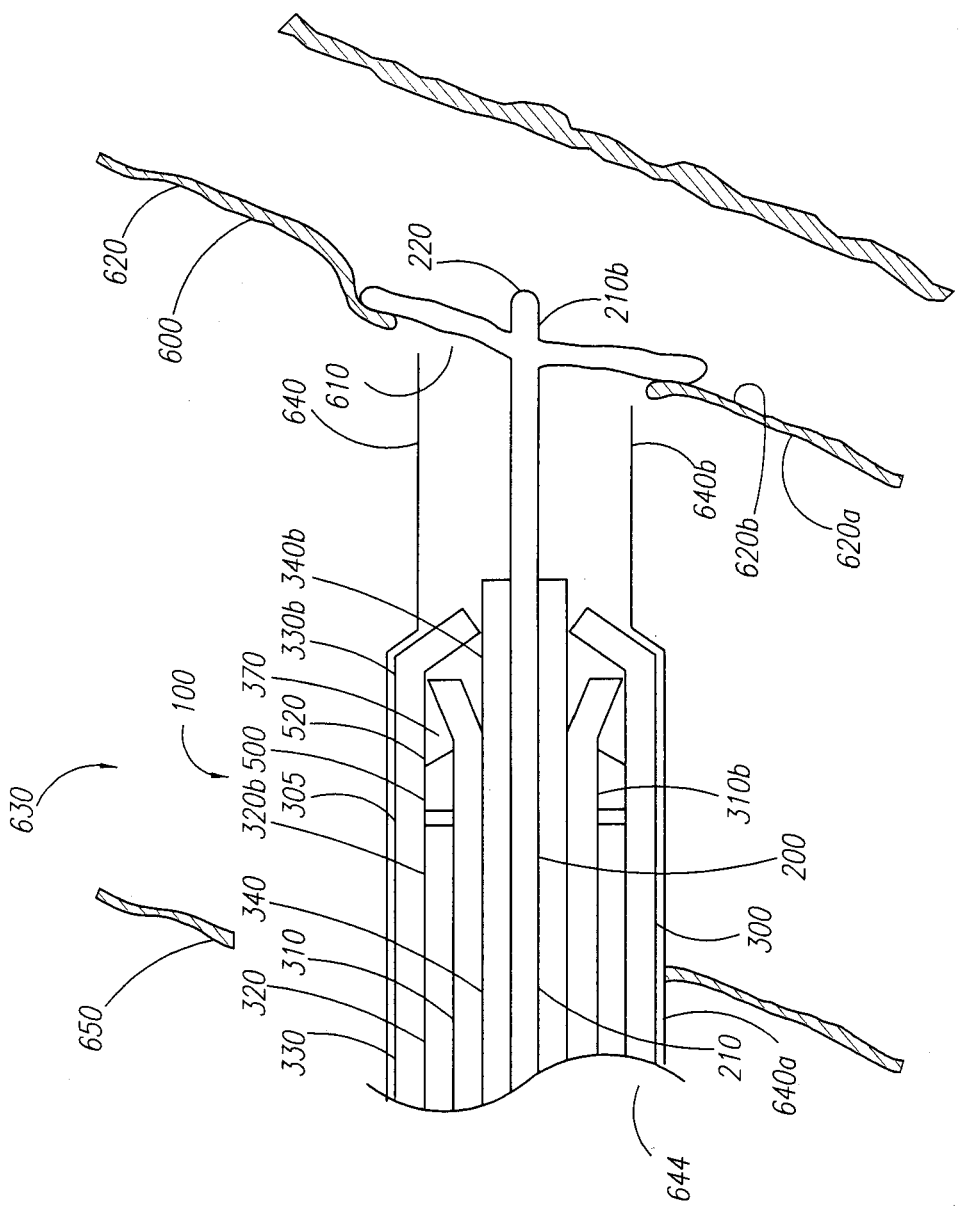

Once distal end region 210b of locator assembly 200 contacts inner surface 620b of blood vessel wall 620, tube set 305 can then be advanced distally and received within lumen 644 of sheath 640. In the manner described above, sheath 640 can radially expand and/or split in accordance with the predetermined pattern as tube set 305 advances because the internal cross-section of sheath 640 is less than or substantially equal to pre-determined cross-section 338b of cover member 330. Being coupled, carrier member 310, pusher member 320, cover member 330, and support member 340 each advance distally and approach the first predetermined position, as illustrated in FIG. 17F. As discussed with reference to the embodiments described in reference to FIGS. 12-15, a stable base can be provided by a handle portion that can receive at least a thumb or finger of the physician. The handle portion can gripped, and optionally extended, by the physician while the physician's hand is rested upon a patient during the procedure and provide stability during use of the device. Additionally, the combined deployment of a locator assembly and the partial advancement of the carrier assembly in a single step allows for a reduction in travel of trigger extension 1405 as it is gripped by the user. Thus, a user does not need to reach uncomfortably far from a handle portion to a trigger extension to fully advance a carrier assembly and the tube set coupled to the carrier assembly.

Upon reaching the first predetermined position, tube set 305 is disposed substantially adjacent to outer surface 620a of blood vessel wall 620 adjacent to opening 610 such that the blood vessel wall adjacent to opening 610 is disposed substantially between expanded distal region 210b of locator assembly 200 and tube set 305. Support member 340 decouples from carrier member 310 and pusher member 320 in the manner described above when tube set 305 is in the first predetermined position. The cover member 330 and pusher member 320 are advanced. After advancement the cover member 330 is decoupled from the carrier member 310 and pusher member 320. Thereby, cover member 330 and support member 340 may be inhibited from further axial movement and remain substantially stationary as carrier member 310 and pusher member 320 each remain coupled and axially slidable.

Figure 17G:
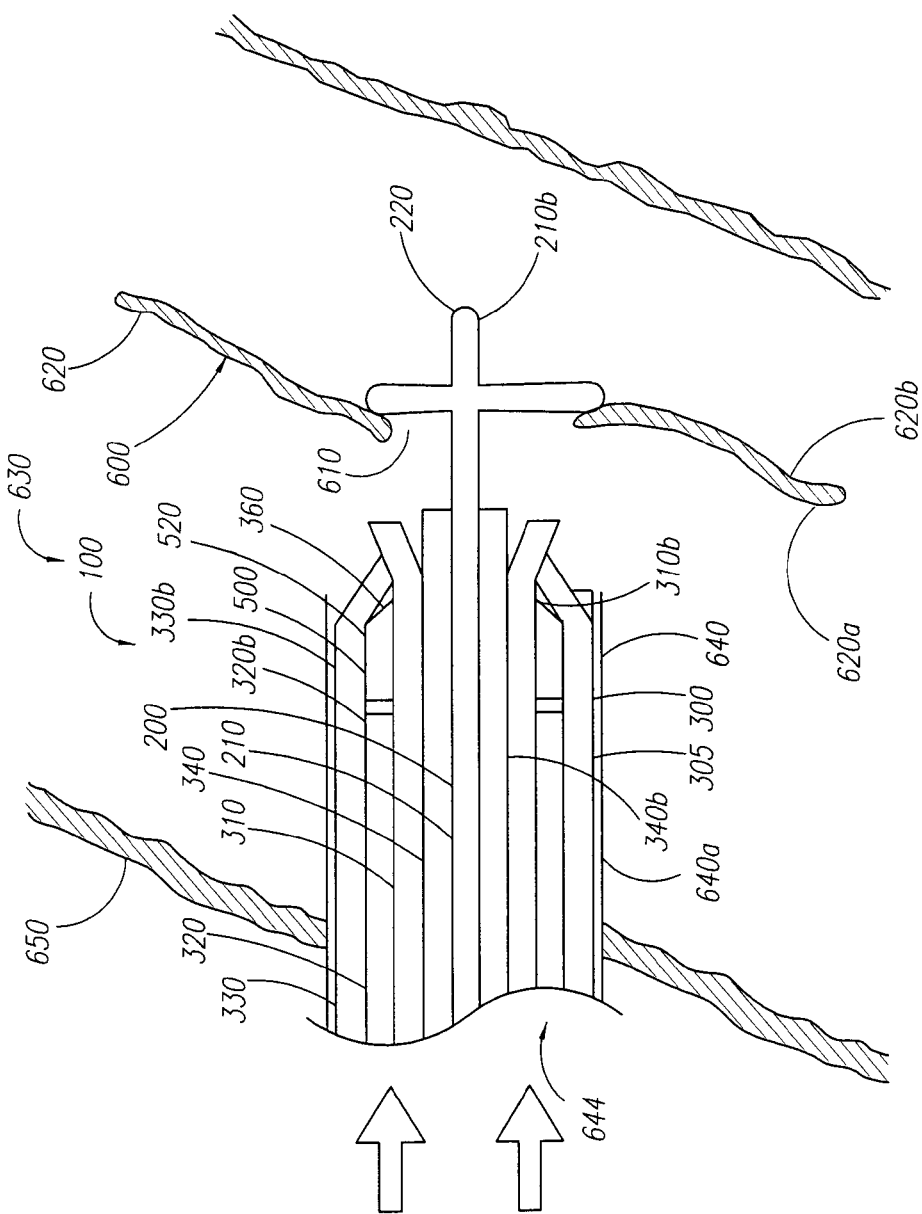

As shown in FIG. 17G, cover member 330 and support member 340 remain substantially stationary while carrier member 310 and pusher member 320 continue distally and approach the second predetermined position. As carrier member 310 and pusher member 320 distally advance toward the second predetermined position, annular cavity 370 moves distally relative to substantially-stationary cover member 330 such that distal end region 330b of cover member 330 no longer encloses annular cavity 370. Thereby, closure element 500 is not completely enclosed by annular cavity 370 formed by distal end regions 310b, 320b, and 330b of carrier member 310, pusher member 320, and cover member 330.

Although not completely enclosed by annular cavity 370, substantially tubular closure element 500 is advantageously retained on outer periphery 312b of carrier member 310 by distal end region 330b of cover member 330 as illustrated in FIG. 17G. For example, by retaining substantially tubular closure element 500 between distal end region 330b of cover member 330 and distal end region 310b carrier member 310, apparatus 100 may be configured to provide better tissue penetration. The timing between the deployment of substantially tubular closure element 500 by tube set 305 and the retraction and transition to the unexpanded state by locator assembly 200 likewise is facilitated because substantially tubular closure element 500 is retained between distal end region 330b and distal end region 310b. Further, carrier member 310 and cover member 330 operate to maintain substantially tubular closure element 500 in the tubular configuration.

Figure 17H:
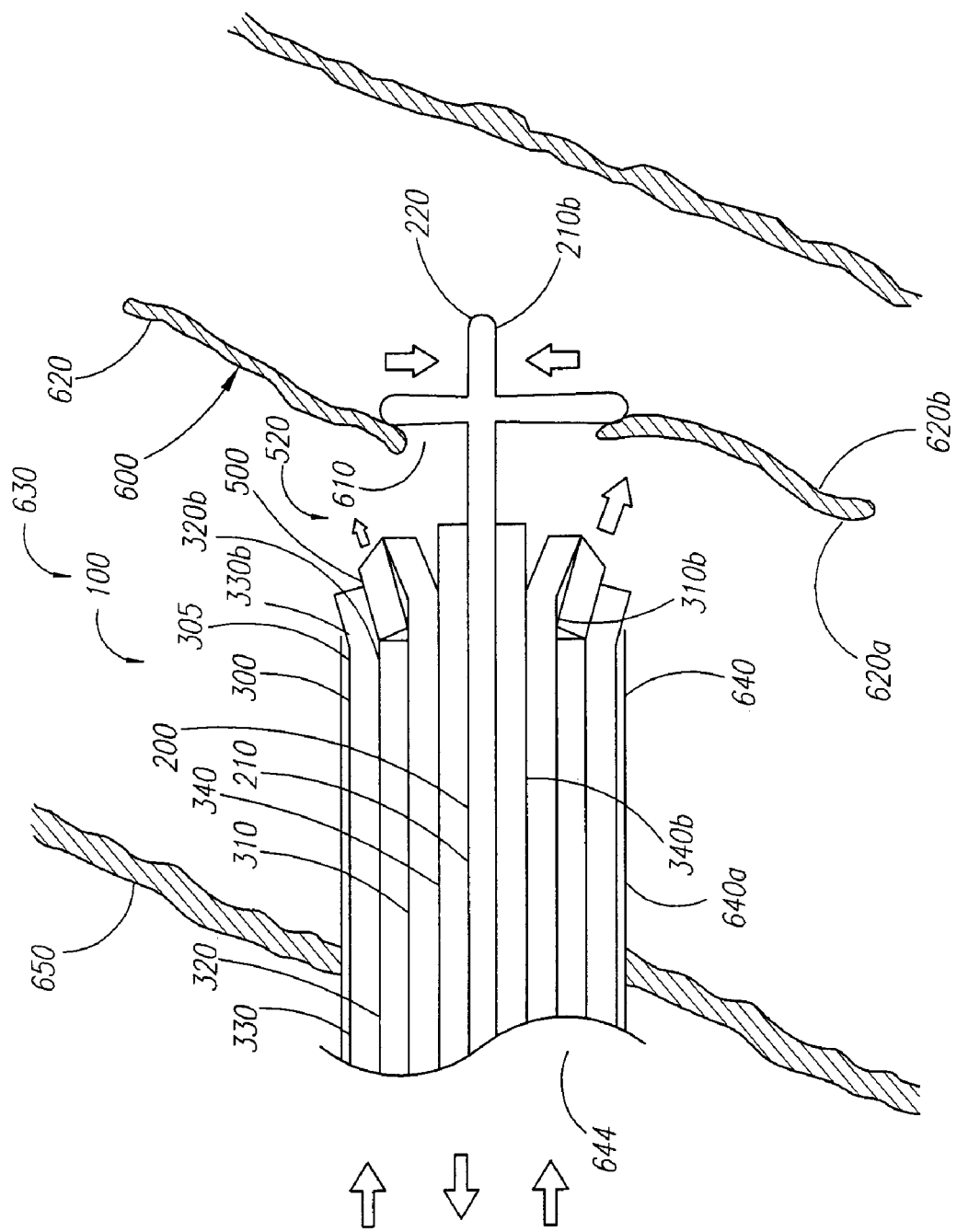

When tube set 305 is in the second predetermined position, carrier member 310 decouples from pusher member 320 in the manner described in detail above. Therefore, carrier member 310, cover member 330, and support member 340 may be inhibited from further axial movement and remain substantially stationary, whereas, pusher member 320 remains axially slidable. As pusher member 320 continues distally, distal end region 320b of pusher member 320 contacts substantially tubular closure element 500 and displaces substantially tubular closure element 500 from space 360 as shown in FIG. 17H. Since space 360 is substantially radially exposed, pusher member 320 directs substantially tubular closure element 500 over the distally-increasing cross-section of distal end region 310b of substantially-stationary carrier member 310 such that the cross-section of substantially tubular closure element 500 begins to radially expand, preferably in a substantially uniform manner. As substantially tubular closure element 500 traverses the distally-increasing cross-section of distal end region 310b, the cross-section of substantially tubular closure element 500 radially expands beyond natural cross-section of closure element 500, as shown in FIGS. 16A-16G.

Figure 17I:
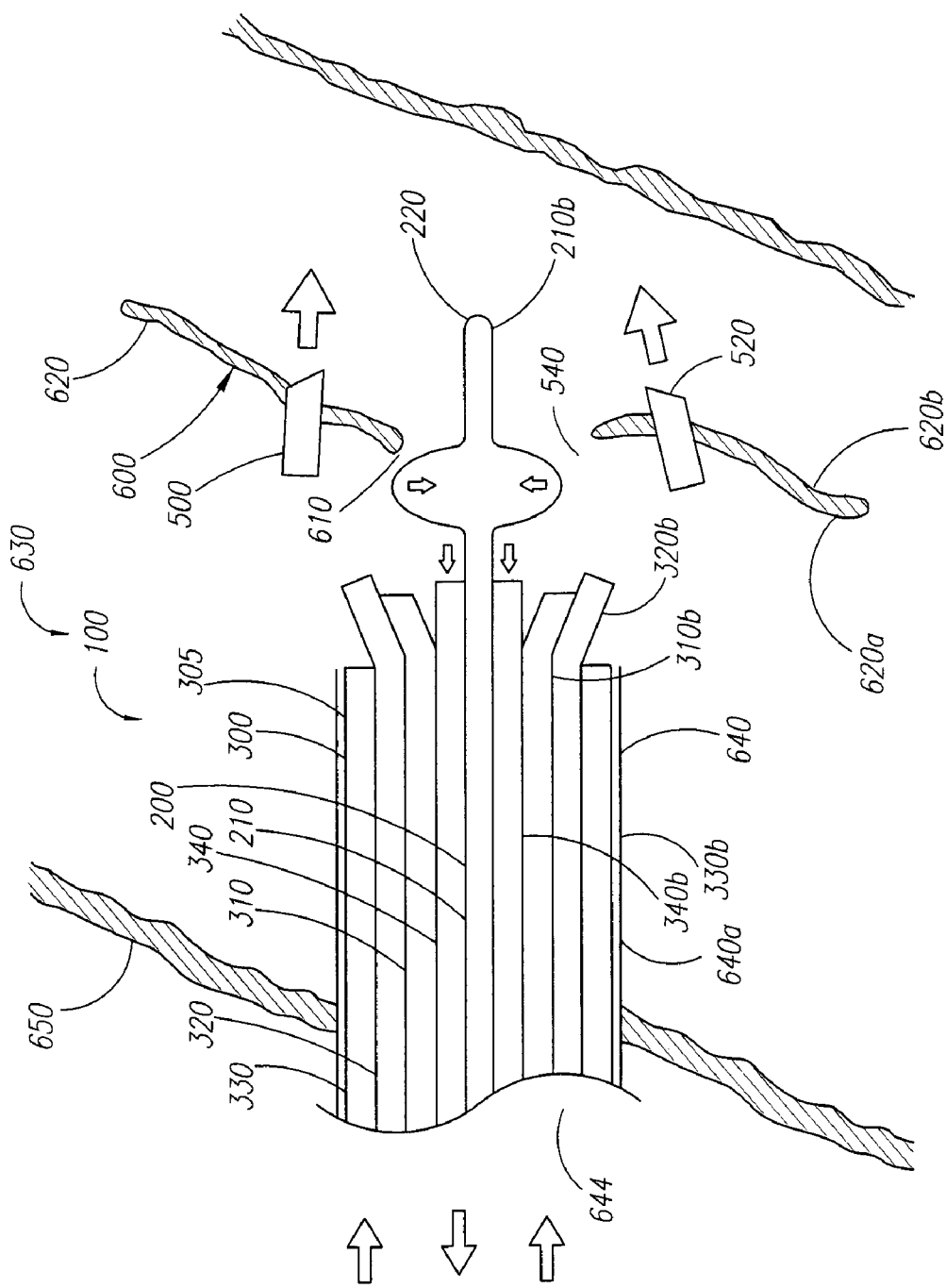

Upon being directed over the distally-increasing cross-section of the distal end region by pusher member 320, substantially tubular closure element 500 is distally deployed as illustrated in FIG. 17I. When substantially tubular closure element 500 is deployed, tines 520 can pierce and otherwise engage significant amount of blood vessel wall 620 and/or tissue 630 adjacent to opening 610. For example, tines 520 can engage significant amount of blood vessel wall 620 and/or tissue 630 because cross-section 530 of substantially tubular closure element 500 is expanded beyond natural cross-section 530 of closure element 500 during deployment.

As the closure element is being deployed from the space, locator assembly 200 may begins to retract proximally and locator release system 490 can be activated to transition from the expanded state to the unexpanded state as substantially tubular closure element 500 is deployed. Distal end region 210b of locator assembly 200 may retract proximally and transition from the expanded state to the unexpanded state substantially simultaneously with the deployment of substantially tubular closure element 500. As desired, distal end region 210b may be configured to draw blood vessel wall 620 and/or tissue 630 adjacent to opening 610 proximally and into the channel defined by substantially tubular closure element 500. Tines 520 of substantially tubular closure element 500 thereby can pierce and otherwise engage blood vessel wall 620 and/or tissue 630.

Figure 17J:
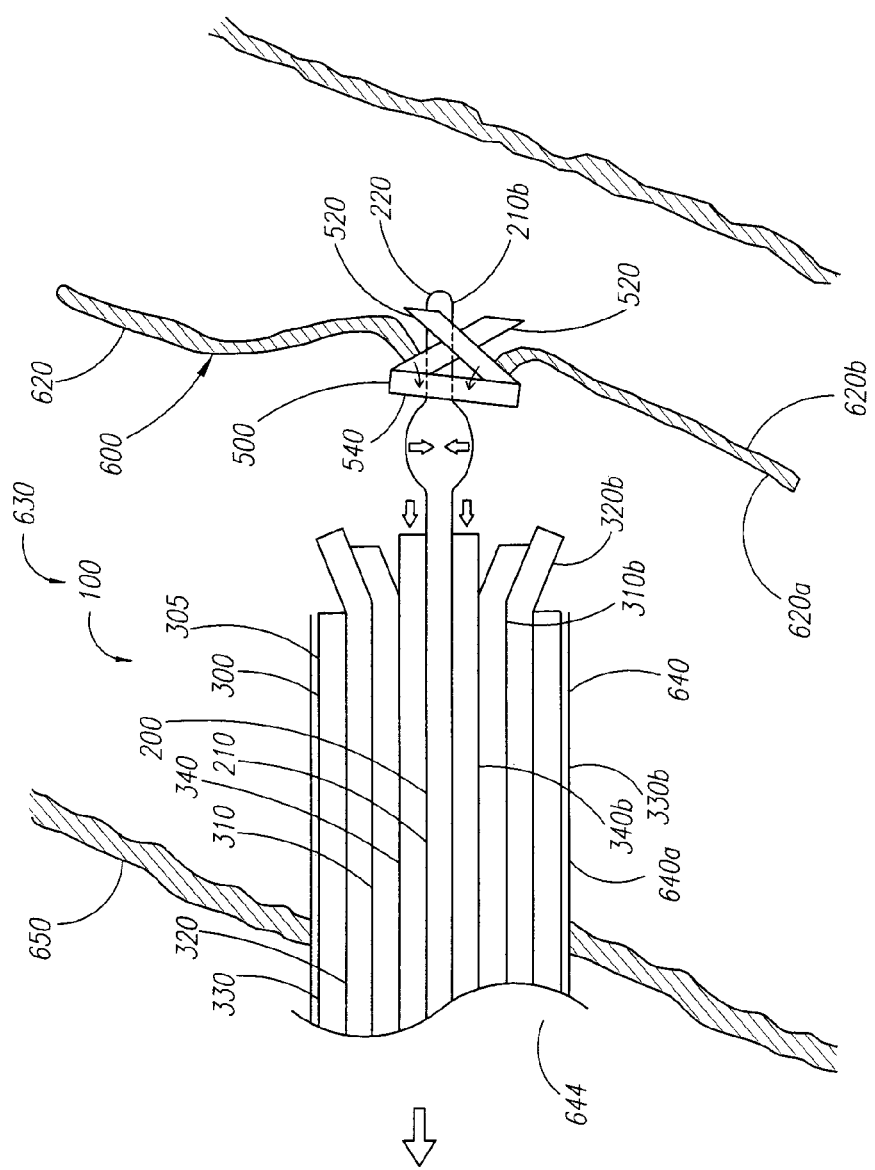
Figure 17K:
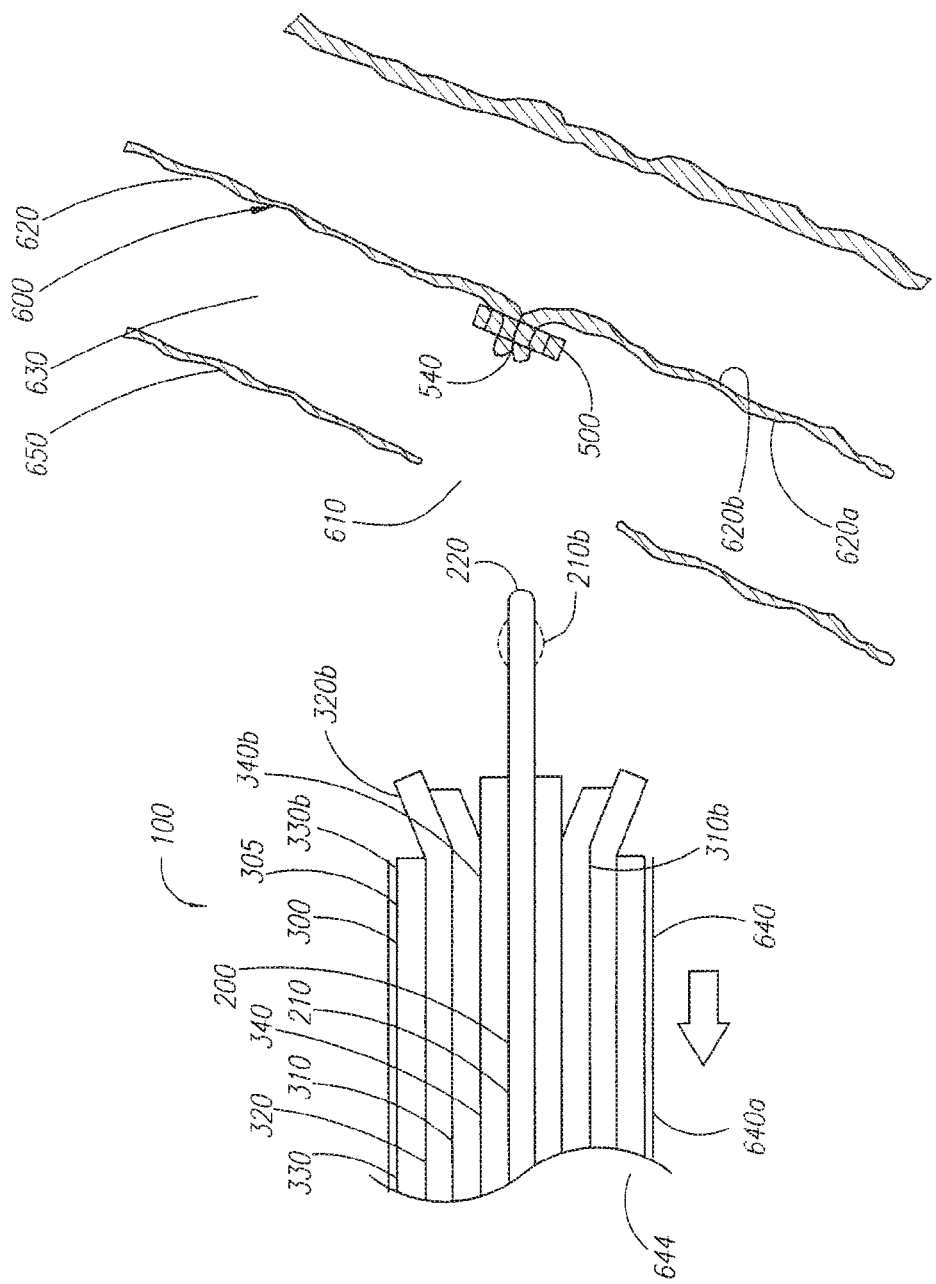

Turning to FIG. 17J, substantially tubular closure element 500, once deployed, begins to transition from the tubular configuration, returning to the natural, planar configuration with opposing tines 520 and a natural cross-section of closure element 500. Preferably, substantially tubular closure element 500 substantially uniformly transitions from the tubular configuration to the natural, planar configuration. Rotating axially inwardly to from opposing tines 520 of the closure element 500, tines 520 draw the tissue into the channel as substantially tubular closure 500 element forms closure element 500. Also, the tissue is drawn substantially closed and/or sealed as the cross-section of substantially tubular closure element 500 contracts to return to the natural cross-section.

It will be appreciated that the closure element may be constructed of other materials, that it may comprise alternative shapes, and that it may adopt alternative methods of operation such that the closure element achieves closure of openings in blood vessel walls or other body tissue. In an additional non-limiting example, the closure element is constructed of materials that use a magnetic force to couple a pair of securing elements in order to close an opening in the lumen wall or tissue. In this alternative embodiment, the closure element may be of a unitary or multi-component construction having a first securing element positionable at a first position adjacent the opening, and a second securing element positionable at a second position adjacent the opening. The first and second securing elements are provided having a magnetic force biasing the first and second securing elements together, thereby closing the opening, or they are provided having a magnetic force biasing both the first and second securing elements toward a third securing element positioned in a manner to cause closure of the opening. The magnetic closure element may be provided without tines, provided the magnetic force coupling the closure elements is sufficient to close the opening. Alternatively, the closure element may be provided with a combination of the magnetic securing elements and tines to provide a combination of coupling forces. Those skilled in the art will recognize that other and further materials, methods, and combinations may be utilized to construct the closure element to achieve the objectives described and implied herein.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

What is claimed is:

1. An apparatus for delivering a closure element to an opening formed in a wall of a body lumen, the apparatus comprising:
   a housing having proximal and distal ends;
   a locator assembly at least partially received within said housing, said locator assembly having a distal end region extendable into an opening formed in a wall of a body lumen;
   a carrier assembly coupled with said locator assembly and at least partially received within said housing, said carrier assembly being adapted to retain a closure element;
   a triggering system coupled with and extending from said carrier assembly and at least partially disposed within said housing, said trigging system being configured to advance said carrier assembly toward said distal end region; and
   a throw reducing mechanism slideably disposed with respect to said housing, wherein said throw reducing mechanism is coupled with said triggering system such that said triggering system is adapted to move relative to said housing as said throw reducing mechanism slides relative to said housing.

2. The apparatus of claim 1, wherein said throw reducing mechanism is a sleeve at least partially enclosing an outer surface of said housing.

3. The apparatus of claim 2, wherein said sleeve is selectively removable from said outer surface of said housing.

4. The apparatus of claim 2, wherein said triggering system comprises a trigger extension extending from said housing, and wherein said sleeve is coupled with said trigger extension.

5. The apparatus of claim 4, wherein said sleeve defines a slot, and wherein said trigger extension is received within said slot.

6. The apparatus of claim 5, wherein said slot has a proximal end and a distal end, and wherein said proximal end of said slot is adapted to engage said trigger extension as said sleeve moves distally relative to said housing, thereby selectively moving trigger extension distally relative to said housing.

7. The apparatus of claim 4, wherein said sleeve comprises a finger extension adapted to facilitate distal movement of said sleeve relative to said housing, and wherein said sleeve is adapted to cause said trigger extension to remain a fixed distance from said finger extension as said sleeve moves distally.

8. The apparatus of claim 4, wherein said sleeve is adapted to move to a distal-most position on said housing, and wherein at said distal-most position of said sleeve, said trigger extension is adapted to move distally relative to said sleeve and said housing.

9. The apparatus of claim 8, wherein said sleeve comprises a finger extension, and wherein said trigger extension is adapted to move to a nested position within said finger extension.

10. The apparatus of claim 2, wherein said housing defines a window adapted to allow a user to determine an operating state of the apparatus, and wherein said sleeve comprises a slot cooperating with said window, such that as said sleeve moves relative to said housing, said window remains visible to said user.

11. The apparatus of claim 2, wherein said sleeve is configured to selectively control said distal end region of said locator assembly between an unexpanded state and an expanded state.

12. The apparatus of claim 11, wherein distal movement of said sleeve relative to said housing causes said distal end region of said locator assembly to transition between said unexpanded state and said expanded state.

13. The apparatus of claim 11, wherein locator assembly comprises a plunger adapted to selectively control said distal end region between said unexpanded state and said expanded state, and wherein said sleeve is coupled with said plunger, such that as said sleeve moves distally relative to said housing, said sleeve causes said plunger to control said distal end region of said locator assembly between said unexpanded state and said expanded state.

14. The apparatus of claim 13, wherein said sleeve substantially encloses said plunger.

15. The apparatus of claim 2, wherein said sleeve is adapted to selectively move relative to said housing to a distal-most position.

16. The apparatus of claim 2, wherein said housing further comprises one or more handles, and wherein said sleeve is adapted to move distally along said housing until said sleeve engages said one or more handles.

17. The apparatus of claim 16, wherein said sleeve is adapted to interlock with said one or more handles when said sleeve engages said one or more handles.

18. The apparatus of claim 16, wherein said one or more handles are selectively removable from said housing.

* * * * *